United States Patent [19]
Eda et al.

[11] Patent Number: 6,114,143
[45] Date of Patent: *Sep. 5, 2000

[54] ANTI-HIV MONOCLONAL ANTIBODY

[75] Inventors: Yasuyuki Eda; Hiroaki Maeda; Keiichi Makizumi; Kouichi Shiosaki, all of Kumamoto; Kiyoshi Osatomi, Nagasaki; Kazuhiko Kimachi, Kumamoto; Hirofumi Higuchi, Kumamoto; Sachio Tokiyoshi, Kumamoto, all of Japan

[73] Assignee: Juridical Foundation The Chemo-Sero-Therapeutic Research Institute, Kumamoto, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/513,968
[22] PCT Filed: Mar. 9, 1994
[86] PCT No.: PCT/JP94/00371
  § 371 Date: Sep. 11, 1995
  § 102(e) Date: Sep. 11, 1995
[87] PCT Pub. No.: WO94/20632
  PCT Pub. Date: Sep. 15, 1994

[30] Foreign Application Priority Data

Mar. 11, 1993 [JP] Japan ................................ 5-078913

[51] Int. Cl.⁷ .......................... C12N 15/09; C12P 21/04; C12P 11/00; A61K 39/395
[52] U.S. Cl. .................. 435/69.3; 435/69.1; 435/69.6; 424/130.1; 424/137.1; 424/139.1; 424/141.1; 424/147.1; 424/160.1
[58] Field of Search .................. 435/69.6, 69.1, 435/69.3; 424/130.1, 137.1, 139.1, 141.1, 147.1, 160.1

[56] References Cited

FOREIGN PATENT DOCUMENTS

| | | |
|---|---|---|
| 0339504 | 11/1989 | European Pat. Off. . |
| 8809181 | 12/1988 | WIPO . |
| 9003984 | 4/1990 | WIPO . |
| 9015078 | 12/1990 | WIPO . |
| 9304090 | 3/1993 | WIPO . |

OTHER PUBLICATIONS

Matsushita, et al. : Characterization of a mouse/human . . . : AIDS Res. and Hum. Retro.: v. 8, No. 6: pp. 1107–1115, 1992.

Ohno, et al. : A broadly neutalizing monoclonal . . . : Proc. Natl. Acad. Sci. : V. 88: pp. 10726–10729, 1991.

Scott, et al. : Human monoclonal antibody that recognizes . . . : Proc. Natl. Acad. Sci. : V. 8: pp. 8597–8601, 1990.

*Primary Examiner*—Jeffrey Stucker
*Assistant Examiner*—Brett Nelson
*Attorney, Agent, or Firm*—Browdy and Neimark

[57] ABSTRACT

A monoclonal antibody useful for clinical application which recognizes the conserved region of V3-PND region of glycoprotein antigen having a molecular weight of about $1.2 \times 10^5$ daltons (gp120) on a coating membrane of human immunodeficiency virus (HIV) and which has an ability to neutralize a broad range of various HIV variants, or a fragment thereof, and the chimeric and humanized antibodies derived therefrom are provided. By using as an immunogen a plurality of peptides having PND-Tip region containing the highly conserved GPGR sequence within PND of HIV gp120, a monoclonal antibody having a neutralizing activity to many HIV variants can be prepared. By transplanting the gene fragment coding for the variable region of said monoclonal antibody or complementarity determining region (CDR) of said region to a human antibody gene, a chimeric antibody or a reshaped antibody having an anti-HIV neutralizing activity which are effective for clinical application can be obtained.

18 Claims, 26 Drawing Sheets

FIG. 3

| Isolated HIV strains | Amino acid sequence of PND | Neutralizing activity against cell-free virus[1] | | | Inhibitory activity against cell-to-cell infection[2] | | |
|---|---|---|---|---|---|---|---|
| | | C25 | u5.5 | a64 | C25 | u5.5 | a64 |
| MN | CTRPNYNKRKRIHIGPGRAFYTTKNIIGTIRQAHC | 1.0 | 0.5 | >500 | 8.0 | 16.0 | >500 |
| KM01 | ----SN-T--S------------GD---D----- | 2.0 | 1.0 | >500 | 16.0 | 8.0 | >500 |
| NI04 | ----GN-T--G--M----TL-A-GE---D----- | 1.0 | 1.0 | >500 | 8.0 | 4.0 | >500 |
| NI55-01 | ----N-T--S--------A-GD---D----- | 1.0 | 0.5 | >500 | 4.0 | 4.0 | >500 |
| NI54-2 | ----N-T--G-RV------I-A-EK---D----- | 0.5 | >500 | 1.0 | 4.0 | >500 | 8.0 |
| NI61-1 | ----N-T--G-R-------V-A-GK---N----- | 2.0 | >500 | 2.0 | 16.0 | >500 | 16.0 |
| DBA3 | ----N-T--G-R-------V-A-EK---D----- | 2.0 | >500 | 2.0 | 16.0 | >500 | 16.0 |
| NI63-2 | ----N-T-RG-R-------A-DK---D----- | 0.5 | >500 | 0.5 | 8.0 | >500 | 8.0 |
| NI53 | ----N-TK-A-RV----TL-A-RR---D----- | 15.6 | >500 | 1.0 | 32.0 | >500 | 16.0 |
| NI23 | ----N-T--S-P----------GE---N----- | 0.5 | >500 | >500 | 8.0 | >500 | >500 |
| NI85-16 | ----N-T--S-N----------GD---D----- | 0.5 | >500 | >500 | 4.0 | >500 | >500 |
| YHI-01 | ----NYTG--VS-------R--GA---D--K--- | 0.5 | >500 | >500 | 4.0 | >500 | >500 |
| TM2 | ----NKA-G-LSV---S-----RQ-T-D----- | 2.0 | >500 | >500 | 8.0 | >500 | >500 |
| PAS | ----N-T--S-RZ-----L-A-GG---D----- | 3.9 | >500 | >500 | 16.0 | >500 | >500 |

Z = IGHI

1. Minimum effective concentration of antibody which inhibits infection by cell-free viruses by 100% (ug/ml)

2. Minimum effective concentration of antibody which inhibits cell-to-cell infection by infected cells by more than 80% (ug/ml)

FIG. 18

| Isolated HIV strains | Sequence of PND | | u5.5 | α64 | C25 |
|---|---|---|---|---|---|
| HIV-MN | CTRPNYNKRKRIHI | GPGRAFYTTKNIIGTIRQAHC | + | − | + |
| NI09-4 | -------------- | --------------------- | + | − | + |
| KM-01 | ----SN-T--S--- | ---------GD---D------ | + | − | + |
| NI29 | -----N-T--S--- | -----W---GE---N------ | + | − | |
| NI60-3 | -----N-T--G--M | ---G-----GE---D------ | + | − | − |
| TM2 | -----NKA-G-LSV | ----S----RQ-T-D------ | − | − | + |
| NI23 | -----N-T--S-P- | ---------GE---N------ | − | − | + |
| NI85-16 | -----N-T--S-N- | ---------GD---D------ | − | − | + |
| NI42 | -----N-T--S-P- | ---------GD---D--K--- | − | − | + |
| NI26 | -----N-T--S-P- | ---------GD---D------ | − | − | + |
| PAS | -----N-T--S-R-Z | -----L-A-GG---D------ | − | − | + |
| TM04 | -----N-T--G-R- | -----V-A-EK---D------ | − | + | + |
| NI85-9 | -----N-T--G-R- | -----V--AEK---D------ | − | + | |
| DBA3 | -----N-T--G-R- | -----V-A-EK---D------ | − | + | + |
| NI61-1 | -----N-T--G-R- | -----V-A-GK---N------ | − | + | + |
| NI61-2 | -----N-T--G-R- | -----V-A-GK---D------ | − | + | + |
| NI54-2 | -----N-T--G-RV | -----I-A-EK---D------ | − | + | + |
| NI36-2 | -----N-TK-S-RMX-W | ---V-A-GK-M-D------ | − | − | − |
| NI63-2 | -----N-T-RG-R- | -------A-DK---D------ | − | + | + |
| NI53 | -----N-TK-A-RV | ----TL-A-RR---D------ | − | + | + |
| SF2 | -----N-T--S-Y- | ------H--GR---D--K--- | − | − | + |
| NI11 | ----SMKT--G--L | -WK-TM-A-GE-K-D------ | − | − | − |
| NI55-01 | -----N-T--S--- | -------A-GD---D------ | + | − | + |
| NI55-04 | -------------- | A------------N------ | − | − | − |
| KMO-01 | -I---N-T--S--- | -------A-GE---N------ | + | − | + |
| KMO-02 | -----N-T--S-N- | -------A-GE---D--K--- | − | − | + |
| TI-01 | -----N-T--S-N- | ---------GQ---N------ | − | − | + |
| TI-07 | -----N-T--S--- | ---------GQ---------- | + | − | + |
| YHI-01 | -----NYTG--VS- | ------R--GA---D--K--- | − | − | + |
| HHA-01 | ----SN-T--S--- | ---------GD---D------ | + | − | + |
| HTU-01 | -----N-T--S--- | ---S-----GE---D------ | + | − | − |
| Binding rate (%) | | | 33% (10/30) | 26% (8/30) | 83% (25/30) |

FIG. 19

```
                                                        (MHL4ver.4)
                                                   AAGGTTGCCGCCACC
| Leader                                                    | FRI   60
ATGGAATGGAGCTGGGTCTTTATCTTTCTCCTGTCAGTAACTGCAGGTGTCCACTCCCAG
MetGluTrpSerTrpValPheIlePheLeuLeuSerValThrAlaGlyValHisSerGln FR1                                         120
GTCCAGCTGCAGCAGTCTGGAGCTGAGCTGGTAAGGCCTGGGACTTCAGTGAAGATGTTC
ValGlnLeuGlnGlnSerGlyAlaGluLeuValArgProGlyThrSerValLysMetPhe FR1              |   CDR1     |      FR2           180
TGCAAGGCTGCTGGATACACCTTCACTAACTCCTGGATAGGTTGGTTTAGGCAGAGGCCT
CysLysAlaAlaGlyTyrThrPheThrAsnSerTrpIleGlyTrpPheArgGlnArgPro

|             CDR2               240
GGACATGGCCTTGAGTGGATTGGAGATATTTACCCTGGAGGTGGTTATACTAACTACAAT
GlyHisGlyLeuGluTrpIleGlyAspIleTyrProGlyGlyGlyTyrThrAsnTyrAsn

|              FR3                         300
GAGATCTTCAAGGGCAAGGCCACACTGACTGCAGACACATCCTCCAGCACAGCCTATATG
GluIlePheLysGlyLysAlaThrLeuThrAlaAspThrSerSerSerThrAlaTyrMet

FR3                               | CDR3  360
CAGCTCAGCAGCCTGACATCTGAGGACTCTGCCATCTATTACTGTTCAAGGGGGATACCG
GlnLeuSerSerLeuThrSerGluAspSerAlaIleTyrTyrCysSerArgGlyIlePro

|              FR4                  | Cγ 2a  420
GGATATGCTATGGACTACTGGGGTCAAGGAACCTCAGTCACCGTCTCCTCAGCCAAAACA
GluTyrAlaMetAspTyrTrpGlyGlnGlyThrSerValThrValSerSerAlaLysThr
                                JH4
                        (MHCver.1)
ACAGCCCCATCGGTCTATGCACTCCCGGGATCC
ThrAlaProSerValTyrProLeuProGlySer : Primer
```

FIG. 20

```
                                              ACTAGTCGAC
| Leader (MKL7ver.2)
ATGGGCATCAAGATGGAGTCACAGATTCTGGTCCTCATGTCCCTGCTGTTCTGGGTATCT   60
MetGlyIleLysMetGluSerGlnIleLeuValLeuMetSerLeuLeuPheTrpValSer

|                     FR1
GGTACCTGTGGGGACATTGTGATGACACAGTCTCCATCCTCCCTGACTGTGACAGCAGGA  120
GlyThrCysGlyAspIleValMetThrGlnSerProSerSerLeuThrValThrAlaGly

|                CDR1
GAGAAGGTCACTATGAGCTGCAAGTCCAGTCAGAGTCTGTTAAACAGTGGAGATCAAAAG  180
GluLysValThrMetSerCysLysSerSerGlnSerLeuLeuAsnSerGlyAspGlnLys

|           FR2                          | CDR2
AACTACTTGACCTGGTACCAGCAGAAACCAGGGCAGCCTCCTAAACTGTTGATCTATTGG  240
AsnTyrLeuThrTrpTyrGlnGlnLysProGlyGlnProProLysLeuLeuIleTyrTrp

CDR2   |                    FR3
GCATCCACTGGGGAATCTGGGGTCCCTGATCGCTTCACAGGCAGTGGATCTGAAACAGAT  300
AlaSerThrGlyGluSerGlyValProAspArgPheThrGlySerGlySerGluThrAsp

FR3                         | CDR3
TTCACTCTCACCATCAGCAGTGTGCAGGCTGAAGACCTGGCAGTTTATTACTGTCAGAAT  360
PheThrLeuThrIleSerSerValGlnAlaGluAspLeuAlaValTyrTyrCysGlnAsn

|               FR4         |   C κ
GATTATAGTTATCCGTGGACGTTCGGTGGAGGCACCAAACTGGAAATCAAACGGGCTGAT  420
AspTyrSerTyrProTrpThrPheGlyGlyGlyThrLysLeuGluIleLysArgAlaAsp
                                Jk1
              (MKCver.1)
GCTGCACCAACTGTATCCATCTTCCCACCATCCACCCGGGATC
AlaAlaProThrValSerIlePhePro : Primer
```

FIG. 21

```
                                                              HindIII
                                                              AAGCTTGCCGCC

|    Leader
         M  D  W  T  W  R  V  F  C  L  L  A  V  A  P  G  A  H  S
      ACCATGGACTGGACCTGGCGCGTGTTTTGCCTGCTCGCCGTGGCTCCTGGGGCCCACAGC

|    FR1
         Q  V  Q  L  V  Q  S  G  A  E  V  K  K  P  G  A  S  V  K  V
   1  CAGGTGCAACTAGTGCAGTCCGGCGCCGAAGTGAAGAAACCCGGTGCTTCCGTGAAGGTG

NheI                  |    CDR1          |    FR2
         S  C  K  A  S  G  Y  T  F  T  E  Y  T  M  H  W  V  R  Q  A
  61  AGCTGTAAAGCTAGCGGTTATACCTTCACTGAATACACCATGCATTGGGTTAGACAGGCC
         5'-========================A=C=C=TGG==AGG====T===========
              Primer #1 —→                  N  S  W  I  G     F

|    CDR2
         P  G  Q  G  L  E  W  I  G  G  I  N  P  N  N  G  D  T  S  Y
 121  CCAGGCCAAGGGCTCGAGTGGATTGGCGGTATTAACCCTAACAATGGCGATACAAGCTAT
         ==-3'         =============A====T=====GGAGG====T======A====
                      3'- ctcacctaaccgctataaatgggacctccaccgatatgtttgata
                       ←—Primer #2     D  Y     G  G     Y        N

|    FR3
         T  Q  K  F  K  G  K  A  T  M  T  V  D  T  S  T  N  T  A  Y
 181  ACCCAGAAGTTTAAGGGCAAGGCTACCATGACCGTAGACACCTCTACAAACACCGCCTAC
         =A=G===TC========
      ttgctctagaaattccc-5'
           I  BGlII
                                                                 |
         M  E  L  S  S  L  R  S  E  D  T  A  V  Y  Y  C  A  T  P  Y
 241  ATGGAACTGTCCAGCCTGCGCTCCGAGGACACTGCAGTATACTACTGCGCCACACCCTAC CDR3                          |    FR4
         Y  A  Y  A  G  D  S  W  G  Q  G  T  L  V  T  V  S
 301  TACGCCTACGCTATTGACTCCTGGGGACAGGGTACCCTTGTCACCGTCAGT
                                          KpnI

|    BamHI EcoRI

S
 361  TCAGGTGAGTGGATCCGAATTC
```

FIG. 22

```
                                                    HindIII
                                                    AAGCTTGCCGCC

|      Leader
       M  D  W  T  W  R  V  F  C  L  L  A  V  A  P  G  A  H  S
       ACCATGGACTGGACCTGGCGCGTGTTTTGCCTGCTCGCCGTGGTCCCTGGGGCCCACAGC

|        FR1
       Q  V  Q  L  V  Q  S  G  A  E  V  K  K  P  G  A  S  V  K  V
  1    CAGGTGCAACTAGTGCAGTCCGGCGCCGAAGTGAAGAAACCCGGTGCTTCCGTGAAGGTG

|    CDR1      |      FR2
       S  C  K  A  S  G  Y  T  F  T  T  Y  P  I  E  W  M  K  Q  N
  61   AGCTGTAAAGCTAGCGGTTATACCTTCACCACCTATCCAATAGAGTGGATGAAACAGAAC
                 NheI

|      CDR2
       P  G  Q  G  L  E  W  I  G  N  F  H  P  Y  S  D  D  T  N  Y
 121   CCAGGCCAAGGGCTCGAGTGGATAGGCAATTTCCACCCTTACAGTGACGATACAAATTAT
                                                              5'-==C===
                                                              Primer #3 →

|       FR3
       K  E  K  F  K  G  K  A  K  L  T  V  D  T  S  T  N  T  A  Y
 181   AACGAGAAATTTAAGGGCAAGGCTAAGCTGACCGTAGACACCTCTACAAACACCGCCTAC
       ======TC================CAA======C=============-3'
          BglII                    T  M       A
             I

|
       M  E  L  S  S  L  R  S  E  D  T  A  V  Y  Y  C  A  I  H  Y
 241   ATGGAACTGTCCAGCCTGCGCTCCGAGGACACTGCAGTCTACTACTGCGCCATACACTAC
                                                 ============T=A=GGGGGATA
                                                 3'-cagatgatgacgagttccccctat
                                                 ←Primer #4    S  R  G  I CDR3                                  |      FR4
       G  S  A  Y  A  M  D  Y  W  G  Q  G  T  L  V  T  V  S
 301   GGTAGTGCCTACGCTATGGACTATTGGGGACAGGGTACCCTTGTCACCGTCAGT
       CCG---=GA=================================
       ggc---cctatgcgatacctgataacccctgtcccatgggaaca-5'
        P        G                               KpnI

|      BamHI EcoRI
          S
 361   TCAGGTGAGTGGATCC
```

FIG. 23

```
                                        HindIII      | Leader
                                                     M  G  W  S  C  I
                                        AAGCTTCGCCACCATGGGATGGAGCTGTATCA
                                                     | Intron
      I  L  F  L  V  A  T  A  T
      TCCTCTTCTTGGTAGCAACAGCTACAGGTAAGGGGCTCACAGTAGCAGGCTTGAGGTCTG

| Leader
                                                     G  V  H  S
      GACATATATATGGGTGACAATGACATCCACTTTGCCTTTCTCTCCACAGGTGTCCACTCC

| FR1
      D  I  Q  M  T  Q  S  P  S  S  L  S  A  S  V  G  D  R  V  T
  1   GACATCCAGATGACCCAGAGCCCAAGCAGCCTGAGCGCCAGCGTGGGTGACAGAGTGACC
                                                        ==========
                                                  Primer #5←3'-GTCTCACTGG

| CDR1                                      | FR2    KpnI
      I  T  C  K  A  S  Q  S  V  D  Y  D  G  D  S  Y  M  N        W  Y
 61   ATCACCTGTAAGGCCAGCCAAAGTGTTGATTATGATGGTGATAGTTATATGAAC------TGGTAC
      ==G=G=======T===========C=GTTAA=CAG===A===CAAA=G=ACT==TTGACC======
      M  S        S              L  L  N  S        Q  K  N  Y  L  T
      TACTCGACATTCAGGTCGGTTTCAGACAATTTGTCACCTCTAGTTTTCTTGATGAACTGGACCATG
                                                           Primer #6←3'-CATG

| CDR2
      Q  Q  K  P  G  K  A  P  K  L  L  I  Y  A  A  S  N  L  E  S
121   CAGCAGAAGCCAGGTAAGGCTCCAAAGCTGCTGATCTACGCTGCATCCAATCTAGAATCT
      ====
      GTCG -5'←- Primer #5
Primer #7→5'- ==================================TGG=======C=GGG======
              GTCGTCTTCGGTCCATTCCGAGGTTTCGACGACTAGATGACCCGTAGGTGACCCCTTAGA
                                                           W         T  G
      | FR3                                    KpnI
      G  V  P  S  R  F  S  G  S  G  S  G  T  D  F  T  F  T  I  S
181   GGTGTGCCAAGCAGATTCAGCGGTAGCGGTAGCGGTACCGACTTCACCTTCACCATCAGC
      ==============================================-3'→Primer #7
      CCACACGGTTCGTCTAAGTCGCCATCGCCATCGC-5'←Primer #6
                     Primer #8→5'-================================
                                                   | CDR3
      S  L  Q  P  E  D  I  A  T  Y  Y  C  Q  Q  S  N  E  D  P  W
241   AGCCTCCAGCCAGAGGACATCGCCACCTACTACTGCCAGCAAAGTAATGAGGACCCATGG
      ====================================T===A=TGA=T==AGTT=======
                                                   N  D  Y  S  Y
          | FR4                           |
      T  F  G  Q  G  T  K  V  E  I  K
301   ACGTTCGGCCAAGGGACCAAGGTGGAAATCAAACGTGAGTAGAATTTAAACTTTGCTTCC
      ============-3'→Primer #8

BamHI
361   TCAGTTGGATCC
```

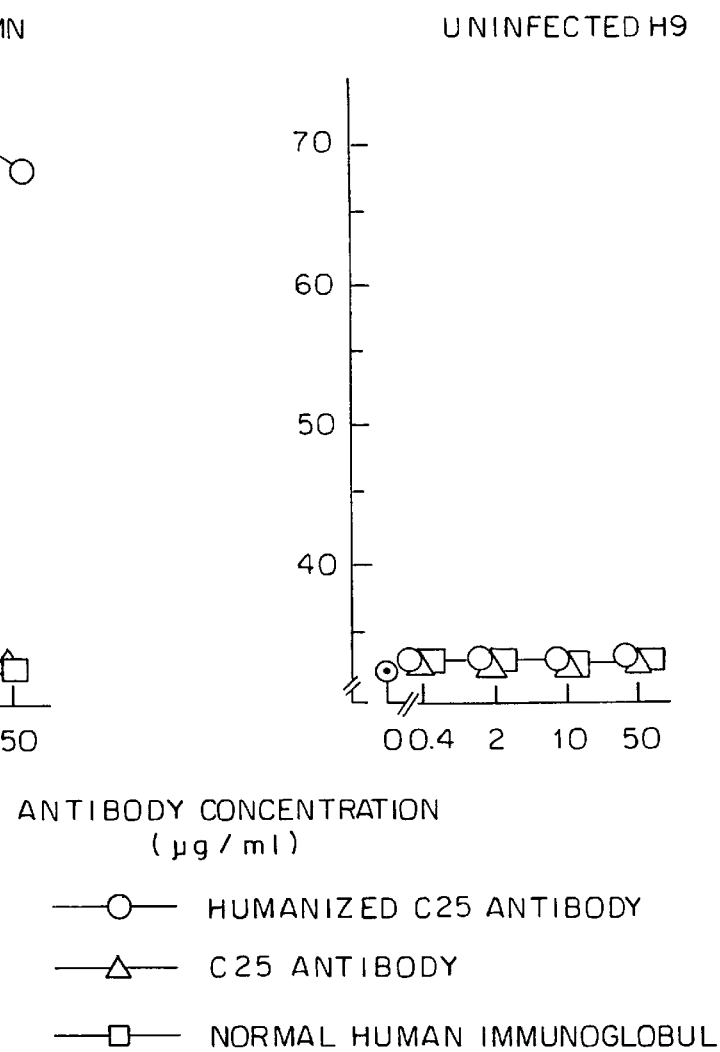

SEQUENCE LISTING (1) GENERAL INFORMATION:

(iii) NUMBER OF SEQUENCES: 86

(2) INFORMATION FOR SEQ ID NO:1:

(i) SEQUENCE CHARACTERISTICS:
      (A) LENGTH: 35 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Cys Thr Arg Pro Asn Tyr Asn Lys Arg Lys Arg Ile His Ile Gly Pro
1          5                10               15

Gly Arg Ala Phe Tyr Thr Thr Lys Asn Ile Ile Gly Thr Ile Arg Gln
        20               25              30

Ala His Cys
    35

(2) INFORMATION FOR SEQ ID NO:2:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Cys Thr Arg Pro Ser Asn Asn Thr Arg Lys Ser Ile His Ile Gly Pro
1               5                   10                  15

Gly Arg Ala Phe Tyr Thr Thr Gly Asp Ile Ile Gly Asp Ile Arg Gln
            20                  25                  30

Ala His Cys
    35

(2) INFORMATION FOR SEQ ID NO:3:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Cys Thr Arg Pro Gly Asn Asn Thr Arg Lys Gly Ile His Met Gly Pro
1               5                   10                  15

Gly Arg Thr Leu Tyr Ala Thr Gly Glu Ile Ile Gly Asp Ile Arg Gln
            20                  25                  30

Ala His Cys
    35

(2) INFORMATION FOR SEQ ID NO:4:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Cys Thr Arg Pro Asn Asn Asn Thr Arg Lys Ser Ile His Ile Gly Pro
1               5                   10                  15

Gly Arg Ala Phe Tyr Ala Thr Gly Asp Ile Ile Gly Asp Ile Arg Gln
            20                  25                  30

Ala His Cys
    35

(2) INFORMATION FOR SEQ ID NO:5:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Cys Thr Arg Pro Asn Asn Asn Thr Arg Lys Gly Ile Arg Val Gly Pro
1               5                   10                  15

Gly Arg Ala Ile Tyr Ala Thr Glu Lys Ile Ile Gly Asp Ile Arg Gln
            20                  25                  30

Ala His Cys
        35

(2) INFORMATION FOR SEQ ID NO:6:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Cys Thr Arg Pro Asn Asn Asn Thr Arg Lys Gly Ile Arg Ile Gly Pro
1               5                   10                  15

Gly Arg Ala Val Tyr Ala Thr Gly Lys Ile Ile Gly Asn Ile Arg Gln
            20                  25                  30

Ala His Cys
        35

(2) INFORMATION FOR SEQ ID NO:7:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Cys Thr Arg Pro Asn Asn Asn Thr Arg Lys Gly Ile Arg Ile Gly Pro
1               5                   10                  15

Gly Arg Ala Val Tyr Ala Thr Glu Lys Ile Ile Gly Asp Ile Arg Gln
            20                  25                  30

Ala His Cys
        35

(2) INFORMATION FOR SEQ ID NO:8:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Cys Thr Arg Pro Asn Asn Asn Thr Arg Arg Gly Ile Arg Ile Gly Pro
1               5                   10                  15

Gly Arg Ala Phe Tyr Ala Thr Asp Lys Ile Ile Gly Asp Ile Arg Gln
            20                  25                  30

Ala His Cys
        35

(2) INFORMATION FOR SEQ ID NO:9:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Cys Thr Arg Pro Asn Asn Asn Thr Lys Lys Ala Ile Arg Val Gly Pro
1               5                  10                  15

Gly Arg Thr Leu Tyr Ala Thr Arg Arg Ile Ile Gly Asp Ile Arg Gln
            20                  25                  30

Ala His Cys
        35
```

(2) INFORMATION FOR SEQ ID NO:10:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Cys Thr Arg Pro Asn Asn Asn Thr Arg Lys Ser Ile Pro Ile Gly Pro
1               5                  10                  15

Gly Arg Ala Phe Tyr Thr Thr Gly Glu Ile Ile Gly Asn Ile Arg Gln
            20                  25                  30

Ala His Cys
        35
```

(2) INFORMATION FOR SEQ ID NO:11:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Cys Thr Arg Pro Asn Asn Asn Thr Arg Lys Ser Ile Asn Ile Gly Pro
1               5                  10                  15

Gly Arg Ala Phe Tyr Thr Thr Gly Asp Ile Ile Gly Asp Ile Arg Gln
            20                  25                  30

Ala His Cys
        35
```

(2) INFORMATION FOR SEQ ID NO:12:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

-continued

Cys Thr Arg Pro Asn Asn Tyr Thr Gly Lys Arg Val Ser Ile Gly Pro
1               5                   10                  15

Gly Arg Ala Phe Arg Thr Thr Gly Ala Ile Ile Gly Asp Ile Arg Lys
            20                  25                  30

Ala His Cys
        35

(2) INFORMATION FOR SEQ ID NO:13:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Cys Thr Arg Pro Asn Asn Lys Ala Arg Gly Arg Leu Ser Val Gly Pro
1               5                   10                  15

Gly Arg Ser Phe Tyr Thr Thr Arg Gln Ile Thr Gly Asp Ile Arg Gln
            20                  25                  30

Ala His Cys
        35

(2) INFORMATION FOR SEQ ID NO:14:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Cys Thr Arg Pro Asn Asn Asn Thr Arg Lys Ser Ile Arg Ile Gly His
1               5                   10                  15

Ile Gly Pro Gly Arg Ala Leu Tyr Ala Thr Gly Gly Ile Ile Gly Asp
            20                  25                  30

Ile Arg Gln Ala His Cys
        35

(2) INFORMATION FOR SEQ ID NO:15:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Cys Thr Arg Pro Asn Tyr Asn Lys Arg Lys Arg Ile His Ile Gly Pro
1               5                   10                  15

Gly Arg Ala Phe Tyr Thr Thr Lys Asn Ile Ile Gly Thr Ile Arg Gln
            20                  25                  30

Ala His Cys
        35

(2) INFORMATION FOR SEQ ID NO:16:

(i) SEQUENCE CHARACTERISTICS:

(A) LENGTH: 35 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:16:

Cys Thr Arg Pro Asn Asn Asn Thr Arg Lys Ser Ile His Ile Gly Pro
1               5                  10                  15

Gly Arg Ala Trp Tyr Thr Thr Gly Glu Ile Ile Gly Asn Ile Arg Gln
            20                  25                  30

Ala His Cys
        35

(2) INFORMATION FOR SEQ ID NO:17:

(i) SEQUENCE CHARACTERISTICS:
            (A) LENGTH: 35 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:17:

Cys Thr Arg Pro Asn Asn Asn Thr Arg Lys Gly Ile His Met Gly Pro
1               5                  10                  15

Gly Gly Ala Phe Tyr Thr Thr Gly Glu Ile Ile Gly Asp Ile Arg Gln
            20                  25                  30

Ala His Cys
        35

(2) INFORMATION FOR SEQ ID NO:18:

(i) SEQUENCE CHARACTERISTICS:
            (A) LENGTH: 35 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:18:

Cys Thr Arg Pro Asn Asn Asn Thr Arg Lys Ser Ile Pro Ile Gly Pro
1               5                  10                  15

Gly Arg Ala Phe Tyr Thr Thr Gly Asp Ile Ile Gly Asp Ile Arg Lys
            20                  25                  30

Ala His Cys
        35

(2) INFORMATION FOR SEQ ID NO:19:

(i) SEQUENCE CHARACTERISTICS:
            (A) LENGTH: 35 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:19:

Cys Thr Arg Pro Asn Asn Asn Thr Arg Lys Ser Ile Pro Ile Gly Pro
1               5                  10                  15

Gly Arg Ala Phe Tyr Thr Thr Gly Asp Ile Ile Gly Asp Ile Arg Gln

```
                    20                  25                  30

Ala His Cys
        35

(2) INFORMATION FOR SEQ ID NO:20:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Cys Thr Arg Pro Asn Asn Asn Thr Arg Lys Gly Ile Arg Ile Gly Pro
1               5                  10                  15

Gly Arg Ala Val Tyr Ala Thr Glu Lys Ile Ile Gly Asp Ile Arg Gln
                20                  25                  30

Ala His Cys
        35

(2) INFORMATION FOR SEQ ID NO:21:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Cys Thr Arg Pro Asn Asn Asn Thr Arg Lys Gly Ile Arg Ile Gly Pro
1               5                  10                  15

Gly Arg Ala Val Tyr Thr Ala Glu Lys Ile Ile Gly Asp Ile Arg Gln
                20                  25                  30

Ala His Cys
        35

(2) INFORMATION FOR SEQ ID NO:22:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Cys Thr Arg Pro Asn Asn Asn Thr Arg Lys Gly Ile Arg Ile Gly Pro
1               5                  10                  15

Gly Arg Ala Val Tyr Ala Thr Gly Lys Ile Ile Gly Asp Ile Arg Gln
                20                  25                  30

Ala His Cys
        35

(2) INFORMATION FOR SEQ ID NO:23:

(i) SEQUENCE CHARACTERISTICS:
        (A) LENGTH: 36 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO:23:

```
Cys Thr Arg Pro Asn Asn Asn Thr Lys Lys Ser Ile Arg Met Xaa Gly
1               5                   10                  15
Trp Gly Arg Ala Val Tyr Ala Thr Gly Lys Ile Met Gly Asp Ile Arg
                20                  25                  30
Gln Ala His Cys
            35
```

(2) INFORMATION FOR SEQ ID NO:24:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Cys Thr Arg Pro Asn Asn Asn Thr Arg Lys Ser Ile Tyr Ile Gly Pro
1               5                   10                  15
Gly Arg Ala Phe His Thr Thr Gly Arg Ile Ile Gly Asp Ile Arg Lys
                20                  25                  30
Ala His Cys
        35
```

(2) INFORMATION FOR SEQ ID NO:25:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Cys Thr Arg Pro Ser Met Lys Thr Arg Lys Gly Ile His Leu Gly Trp
1               5                   10                  15
Lys Arg Thr Met Tyr Ala Thr Gly Glu Ile Lys Gly Asp Ile Arg Gln
                20                  25                  30
Ala His Cys
        35
```

(2) INFORMATION FOR SEQ ID NO:26:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Cys Thr Arg Pro Asn Tyr Asn Lys Arg Lys Arg Ile His Ile Ala Pro
1               5                   10                  15
Gly Arg Ala Phe Tyr Thr Thr Lys Asn Ile Ile Gly Asn Ile Arg Gln
                20                  25                  30
Ala His Cys
        35
```

(2) INFORMATION FOR SEQ ID NO:27:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

Cys Ile Arg Pro Asn Asn Asn Thr Arg Lys Ser Ile His Ile Gly Pro
1               5                  10                  15

Gly Arg Ala Phe Tyr Ala Thr Gly Glu Ile Ile Gly Asn Ile Arg Gln
            20                  25                  30

Ala His Cys
        35

(2) INFORMATION FOR SEQ ID NO:28:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Cys Thr Arg Pro Asn Asn Asn Thr Arg Lys Ser Ile Asn Ile Gly Pro
1               5                  10                  15

Gly Arg Ala Phe Tyr Ala Thr Gly Glu Ile Ile Gly Asp Ile Arg Lys
            20                  25                  30

Ala His Cys
        35

(2) INFORMATION FOR SEQ ID NO:29:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Cys Thr Arg Pro Asn Asn Asn Thr Arg Lys Ser Ile Asn Ile Gly Pro
1               5                  10                  15

Gly Arg Ala Phe Tyr Thr Thr Gly Gln Ile Ile Gly Asn Ile Arg Gln
            20                  25                  30

Ala His Cys
        35

(2) INFORMATION FOR SEQ ID NO:30:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
Cys Thr Arg Pro Asn Asn Asn Thr Arg Lys Ser Ile His Ile Gly Pro
1               5                   10                  15

Gly Arg Ala Phe Tyr Thr Thr Gly Gln Ile Ile Gly Thr Ile Arg Gln
            20                  25                  30

Ala His Cys
        35

(2) INFORMATION FOR SEQ ID NO:31:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

Cys Thr Arg Pro Ser Asn Asn Thr Arg Lys Ser Ile His Ile Gly Pro
1               5                   10                  15

Gly Arg Ala Phe Tyr Thr Thr Gly Asp Ile Ile Gly Asp Ile Arg Gln
            20                  25                  30

Ala His Cys
        35

(2) INFORMATION FOR SEQ ID NO:32:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

Cys Thr Arg Pro Asn Asn Asn Thr Arg Lys Ser Ile His Ile Gly Pro
1               5                   10                  15

Gly Ser Ala Phe Tyr Thr Thr Gly Glu Ile Ile Gly Asp Ile Arg Gln
            20                  25                  30

Ala His Cys
        35

(2) INFORMATION FOR SEQ ID NO:33:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..453

(xi) SEQUENCE DESCRIPTION: SEQ ID NO:33:

ATG GAA TGG AGC TGG GTC TTT ATC TTT CTC CTG TCA GTA ACT GCA GGT        48
Met Glu Trp Ser Trp Val Phe Ile Phe Leu Leu Ser Val Thr Ala Gly
1               5                   10                  15

GTC CAC TCC CAG GTC CAG CTG CAG CAG TCT GGA GCT GAG CTG GTA AGG        96
Val His Ser Gln Val Gln Leu Gln Gln Ser Gly Ala Glu Leu Val Arg
            20                  25                  30
```

```
CCT GGG ACT TCA GTG AAG ATG TTC TGC AAG GCT GCT GGA TAC ACC TTC       144
Pro Gly Thr Ser Val Lys Met Phe Cys Lys Ala Ala Gly Tyr Thr Phe
        35                  40                  45

ACT AAC TCC TGG ATA GGT TGG TTT AGG CAG AGG CCT GGA CAT GGC CTT       192
Thr Asn Ser Trp Ile Gly Trp Phe Arg Gln Arg Pro Gly His Gly Leu
 50                  55                  60

GAG TGG ATT GGA GAT ATT TAC CCT GGA GGT GGT TAT ACT AAC TAC AAT       240
Glu Trp Ile Gly Asp Ile Tyr Pro Gly Gly Gly Tyr Thr Asn Tyr Asn
 65                  70                  75                  80

GAG ATC TTC AAG GGC AAG GCC ACA CTG ACT GCA GAC ACA TCC TCC AGC       288
Glu Ile Phe Lys Gly Lys Ala Thr Leu Thr Ala Asp Thr Ser Ser Ser
                 85                  90                  95

ACA GCC TAT ATG CAG CTC AGC AGC CTG ACA TCT GAG GAC TCT GCC ATC       336
Thr Ala Tyr Met Gln Leu Ser Ser Leu Thr Ser Glu Asp Ser Ala Ile
            100                 105                 110

TAT TAC TGT TCA AGG GGG ATA CCG GGA TAT GCT ATG GAC TAC TGG GGT       384
Tyr Tyr Cys Ser Arg Gly Ile Pro Gly Tyr Ala Met Asp Tyr Trp Gly
            115                 120                 125

CAA GGA ACC TCA GTC ACC GTC TCC TCA GCC AAA ACA ACA GCC CCA TCG       432
Gln Gly Thr Ser Val Thr Val Ser Ser Ala Lys Thr Thr Ala Pro Ser
130                 135                 140

GTC TAT GCA CTC CCG GGA TCC                                           453
Val Tyr Ala Leu Pro Gly Ser
145                 150
```

(2) INFORMATION FOR SEQ ID NO:34:

(i) SEQUENCE CHARACTERISTICS:
        (A) LENGTH: 151 amino acids
        (B) TYPE: amino acid
        (D) TOPOLOGY: linear (ii) MOLECULE TYPE: protein (xi) SEQUENCE DESCRIPTION: SEQ ID NO:34:

```
Met Glu Trp Ser Trp Val Phe Ile Phe Leu Leu Ser Val Thr Ala Gly
 1               5                  10                  15

Val His Ser Gln Val Gln Leu Gln Gln Ser Gly Ala Glu Leu Val Arg
            20                  25                  30

Pro Gly Thr Ser Val Lys Met Phe Cys Lys Ala Ala Gly Tyr Thr Phe
        35                  40                  45

Thr Asn Ser Trp Ile Gly Trp Phe Arg Gln Arg Pro Gly His Gly Leu
 50                  55                  60

Glu Trp Ile Gly Asp Ile Tyr Pro Gly Gly Gly Tyr Thr Asn Tyr Asn
 65                  70                  75                  80

Glu Ile Phe Lys Gly Lys Ala Thr Leu Thr Ala Asp Thr Ser Ser Ser
                 85                  90                  95

Thr Ala Tyr Met Gln Leu Ser Ser Leu Thr Ser Glu Asp Ser Ala Ile
            100                 105                 110

Tyr Tyr Cys Ser Arg Gly Ile Pro Gly Tyr Ala Met Asp Tyr Trp Gly
            115                 120                 125

Gln Gly Thr Ser Val Thr Val Ser Ser Ala Lys Thr Thr Ala Pro Ser
130                 135                 140

Val Tyr Ala Leu Pro Gly Ser
145                 150
```

(2) INFORMATION FOR SEQ ID NO:35:

(i) SEQUENCE CHARACTERISTICS:
        (A) LENGTH: 463 base pairs (B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..463

(xi) SEQUENCE DESCRIPTION: SEQ ID NO:35:

| | | | | | | | | | | | | | | | | |
|---|---|---|---|---|---|---|---|---|---|---|---|---|---|---|---|---|
| ATG | GGC | ATC | AAG | ATG | GAG | TCA | CAG | ATT | CTG | GTC | CTC | ATG | TCC | CTG | CTG | 48 |
| Met | Gly | Ile | Lys | Met | Glu | Ser | Gln | Ile | Leu | Val | Leu | Met | Ser | Leu | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| TTC | TGG | GTA | TCT | GGT | ACC | TGT | GGG | GAC | ATT | GTG | ATG | ACA | CAG | TCT | CCA | 96 |
| Phe | Trp | Val | Ser | Gly | Thr | Cys | Gly | Asp | Ile | Val | Met | Thr | Gln | Ser | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| TCC | TCC | CTG | ACT | GTG | ACA | GCA | GGA | GAG | AAG | GTC | ACT | ATG | AGC | TGC | AAG | 144 |
| Ser | Ser | Leu | Thr | Val | Thr | Ala | Gly | Glu | Lys | Val | Thr | Met | Ser | Cys | Lys | |
| | | 35 | | | | | 40 | | | | | 45 | | | | |

| | | | | | | | | | | | | | | | | |
|---|---|---|---|---|---|---|---|---|---|---|---|---|---|---|---|---|
| TCC | AGT | CAG | AGT | CTG | TTA | AAC | AGT | GGA | GAT | CAA | AAG | AAC | TAC | TTG | ACC | 192 |
| Ser | Ser | Gln | Ser | Leu | Leu | Asn | Ser | Gly | Asp | Gln | Lys | Asn | Tyr | Leu | Thr | |
| 50 | | | | | 55 | | | | | 60 | | | | | | |

| | | | | | | | | | | | | | | | | |
|---|---|---|---|---|---|---|---|---|---|---|---|---|---|---|---|---|
| TGG | TAC | CAG | CAG | AAA | CCA | GGG | CAG | CCT | CCT | AAA | CTG | TTG | ATC | TAT | TGG | 240 |
| Trp | Tyr | Gln | Gln | Lys | Pro | Gly | Gln | Pro | Pro | Lys | Leu | Leu | Ile | Tyr | Trp | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| GCA | TCC | ACT | GGG | GAA | TCT | GGG | GTC | CCT | GAT | CGC | TTC | ACA | GGC | AGT | GGA | 288 |
| Ala | Ser | Thr | Gly | Glu | Ser | Gly | Val | Pro | Asp | Arg | Phe | Thr | Gly | Ser | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| TCT | GAA | ACA | GAT | TTC | ACT | CTC | ACC | ATC | AGC | AGT | GTG | CAG | GCT | GAA | GAC | 336 |
| Ser | Glu | Thr | Asp | Phe | Thr | Leu | Thr | Ile | Ser | Ser | Val | Gln | Ala | Glu | Asp | |
| | | | 100 | | | | | 105 | | | | | 110 | | | |

| | | | | | | | | | | | | | | | | |
|---|---|---|---|---|---|---|---|---|---|---|---|---|---|---|---|---|
| CTG | GCA | GTT | TAT | TAC | TGT | CAG | AAT | GAT | TAT | AGT | TAT | CCG | TGG | ACG | TTC | 384 |
| Leu | Ala | Val | Tyr | Tyr | Cys | Gln | Asn | Asp | Tyr | Ser | Tyr | Pro | Trp | Thr | Phe | |
| | | 115 | | | | | 120 | | | | | 125 | | | | |

| | | | | | | | | | | | | | | | | |
|---|---|---|---|---|---|---|---|---|---|---|---|---|---|---|---|---|
| GGT | GGA | GGC | ACC | AAA | CTG | GAA | ATC | AAA | CGG | GCT | GAT | GCT | GCA | CCA | ACT | 432 |
| Gly | Gly | Gly | Thr | Lys | Leu | Glu | Ile | Lys | Arg | Ala | Asp | Ala | Ala | Pro | Thr | |
| | | 130 | | | | | 135 | | | | | 140 | | | | |

| | | | | | | | | | |
|---|---|---|---|---|---|---|---|---|---|
| GTA | TCC | ATC | TTC | CCA | CCA | TCC | ACC | CGG | GAT C | 463 |
| Val | Ser | Ile | Phe | Pro | Pro | Ser | Thr | Arg | Asp | |
| 145 | | | | | 150 | | | | | |

(2) INFORMATION FOR SEQ ID NO:36:

(i) SEQUENCE CHARACTERISTICS:
(A) LENGTH: 154 amino acids
(B) TYPE: amino acid
(D) TOPOLOGY: linear (ii) MOLECULE TYPE: protein (xi) SEQUENCE DESCRIPTION: SEQ ID NO:36:

| | | | | | | | | | | | | | | | |
|---|---|---|---|---|---|---|---|---|---|---|---|---|---|---|---|
| Met | Gly | Ile | Lys | Met | Glu | Ser | Gln | Ile | Leu | Val | Leu | Met | Ser | Leu | Leu |
| 1 | | | | 5 | | | | | 10 | | | | | 15 | |

| | | | | | | | | | | | | | | | |
|---|---|---|---|---|---|---|---|---|---|---|---|---|---|---|---|
| Phe | Trp | Val | Ser | Gly | Thr | Cys | Gly | Asp | Ile | Val | Met | Thr | Gln | Ser | Pro |
| | | | 20 | | | | | 25 | | | | | 30 | | |

| | | | | | | | | | | | | | | | |
|---|---|---|---|---|---|---|---|---|---|---|---|---|---|---|---|
| Ser | Ser | Leu | Thr | Val | Thr | Ala | Gly | Glu | Lys | Val | Thr | Met | Ser | Cys | Lys |
| | | 35 | | | | | 40 | | | | | 45 | | | |

| | | | | | | | | | | | | | | | |
|---|---|---|---|---|---|---|---|---|---|---|---|---|---|---|---|
| Ser | Ser | Gln | Ser | Leu | Leu | Asn | Ser | Gly | Asp | Gln | Lys | Asn | Tyr | Leu | Thr |
| 50 | | | | | 55 | | | | | 60 | | | | | |

| | | | | | | | | | | | | | | | |
|---|---|---|---|---|---|---|---|---|---|---|---|---|---|---|---|
| Trp | Tyr | Gln | Gln | Lys | Pro | Gly | Gln | Pro | Pro | Lys | Leu | Leu | Ile | Tyr | Trp |
| 65 | | | | | 70 | | | | | 75 | | | | | 80 |

```
Ala Ser Thr Gly Glu Ser Gly Val Pro Asp Arg Phe Thr Gly Ser Gly
             85                  90                  95

Ser Glu Thr Asp Phe Thr Leu Thr Ile Ser Ser Val Gln Ala Glu Asp
        100                 105                 110

Leu Ala Val Tyr Tyr Cys Gln Asn Asp Tyr Ser Tyr Pro Trp Thr Phe
            115                 120                 125

Gly Gly Gly Thr Lys Leu Glu Ile Lys Arg Ala Asp Ala Ala Pro Thr
130                 135                 140

Val Ser Ile Phe Pro Pro Ser Thr Arg Asp
145                 150

(2) INFORMATION FOR SEQ ID NO:37:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 16..426

(xi) SEQUENCE DESCRIPTION: SEQ ID NO:37:

AAGCTTGCCG CCACC ATG GAC TGG ACC TGG CGC GTG TTT TGC CTG CTC GCC            51
                 Met Asp Trp Thr Trp Arg Val Phe Cys Leu Leu Ala
                  1               5                  10

GTG GCT CCT GGG GCC CAC AGC CAG GTG CAA CTA GTG CAG TCC GGC GCC             99
Val Ala Pro Gly Ala His Ser Gln Val Gln Leu Val Gln Ser Gly Ala
        15                  20                  25

GAA GTG AAG AAA CCC GGT GCT TCC GTG AAG GTG AGC TGT AAA GCT AGC            147
Glu Val Lys Lys Pro Gly Ala Ser Val Lys Val Ser Cys Lys Ala Ser
 30                  35                  40

GGT TAT ACC TTC ACT GAA TAC ACC ATG CAT TGG GTT AGA CAG GCC CCA            195
Gly Tyr Thr Phe Thr Glu Tyr Thr Met His Trp Val Arg Gln Ala Pro
 45                  50                  55                  60

GGC CAA GGG CTC GAG TGG ATT GGC GGT ATT AAC CCT AAC AAT GGC GAT            243
Gly Gln Gly Leu Glu Trp Ile Gly Gly Ile Asn Pro Asn Asn Gly Asp
            65                  70                  75

ACA AGC TAT ACC CAG AAG TTT AAG GGC AAG GCT ACC ATG ACC GTA GAC            291
Thr Ser Tyr Thr Gln Lys Phe Lys Gly Lys Ala Thr Met Thr Val Asp
                 80                  85                  90

ACC TCT ACA AAC ACC GCC TAC ATG GAA CTG TCC AGC CTG CGC TCC GAG            339
Thr Ser Thr Asn Thr Ala Tyr Met Glu Leu Ser Ser Leu Arg Ser Glu
        95                 100                 105

GAC ACT GCA GTA TAC TAC TGC GCC ACA CCC TAC TAC GCC TAC GCT ATT            387
Asp Thr Ala Val Tyr Tyr Cys Ala Thr Pro Tyr Tyr Ala Tyr Ala Ile
110                 115                 120

GAC TCC TGG GGA CAG GGT ACC CTT GTC ACC GTC AGT TCA GGTGAGTGGA             436
Asp Ser Trp Gly Gln Gly Thr Leu Val Thr Val Ser Ser
125                 130                 135

TCCGAATTC                                                                  445

(2) INFORMATION FOR SEQ ID NO:38:

(i) SEQUENCE CHARACTERISTICS:
        (A) LENGTH: 137 amino acids
        (B) TYPE: amino acid
        (D) TOPOLOGY: linear (ii) MOLECULE TYPE: protein
```

(xi) SEQUENCE DESCRIPTION: SEQ ID NO:38:

Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Glu Tyr Thr Met His Trp Val Arg Gln Ala Pro Gly Gln Gly Leu
    50                  55                  60

Glu Trp Ile Gly Gly Ile Asn Pro Asn Asn Gly Asp Thr Ser Tyr Thr
65                  70                  75                  80

Gln Lys Phe Lys Gly Lys Ala Thr Met Thr Val Asp Thr Ser Thr Asn
                85                  90                  95

Thr Ala Tyr Met Glu Leu Ser Ser Leu Arg Ser Glu Asp Thr Ala Val
            100                 105                 110

Tyr Tyr Cys Ala Thr Pro Tyr Tyr Ala Tyr Ala Ile Asp Ser Trp Gly
        115                 120                 125

Gln Gly Thr Leu Val Thr Val Ser Ser
    130                 135

(2) INFORMATION FOR SEQ ID NO:39:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..56

(xi) SEQUENCE DESCRIPTION: SEQ ID NO:39:

AAA GCT AGC GGT TAT ACC TTC ACT AAC TCC TGG ATA GGT TGG TTT AGA      48
Lys Ala Ser Gly Tyr Thr Phe Thr Asn Ser Trp Ile Gly Trp Phe Arg
1               5                   10                  15

CAG GCC  CC                                                           56
Gln Ala (2) INFORMATION FOR SEQ ID NO:40:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:40:

Lys Ala Ser Gly Tyr Thr Phe Thr Asn Ser Trp Ile Gly Trp Phe Arg
1               5                   10                  15

Gln Ala (2) INFORMATION FOR SEQ ID NO:41:

(i) SEQUENCE CHARACTERISTICS:
        (A) LENGTH: 62 base pairs
        (B) TYPE: nucleic acid
        (C) STRANDEDNESS: single
        (D) TOPOLOGY: linear

```
      (ii) MOLECULE TYPE: cDNA (ix) FEATURE:
           (A) NAME/KEY: CDS
           (B) LOCATION: 1..62

(xi) SEQUENCE DESCRIPTION: SEQ ID NO:41:

GAG TGG ATT GGC GAT ATT TAC CCT GGA GGT GGC TAT ACA AAC TAT AAC         48
Glu Trp Ile Gly Asp Ile Tyr Pro Gly Gly Gly Tyr Thr Asn Tyr Asn
 1               5                  10                  15

GAG ATC TTT AAG  GG                                                     62
Glu Ile Phe Lys (2) INFORMATION FOR SEQ ID NO:42:

(i) SEQUENCE CHARACTERISTICS:
          (A) LENGTH: 20 amino acids
          (B) TYPE: amino acid
          (D) TOPOLOGY: linear (ii) MOLECULE TYPE: protein (xi) SEQUENCE DESCRIPTION: SEQ ID NO:42:

Glu Trp Ile Gly Asp Ile Tyr Pro Gly Gly Gly Tyr Thr Asn Tyr Asn
 1               5                  10                  15

Glu Ile Phe Lys
            20

(2) INFORMATION FOR SEQ ID NO:43:

(i) SEQUENCE CHARACTERISTICS:
          (A) LENGTH: 442 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: CDS
          (B) LOCATION: 16..429

(xi) SEQUENCE DESCRIPTION: SEQ ID NO:43:

AAGCTTGCCG CCACC ATG GAC TGG ACC TGG CGC GTG TTT TGC CTG CTC GCC        51
                Met Asp Trp Thr Trp Arg Val Phe Cys Leu Leu Ala
                 1               5                      10

GTG GCT CCT GGG GCC CAC AGC CAG GTG CAA CTA GTG CAG TCC GGC GCC         99
Val Ala Pro Gly Ala His Ser Gln Val Gln Leu Val Gln Ser Gly Ala
                15                  20                  25

GAA GTG AAG AAA CCC GGT GCT TCC GTG AAG GTG AGC TGT AAA GCT AGC        147
Glu Val Lys Lys Pro Gly Ala Ser Val Lys Val Ser Cys Lys Ala Ser
         30                  35                  40

GGT TAT ACC TTC ACC ACC TAT CCA ATA GAG TGG ATG AAA CAG AAC CCA        195
Gly Tyr Thr Phe Thr Thr Tyr Pro Ile Glu Trp Met Lys Gln Asn Pro
 45                  50                  55                  60

GGC CAA GGG CTC GAG TGG ATA GGC AAT TTC CAC CCT TAC AGT GAC GAT        243
Gly Gln Gly Leu Glu Trp Ile Gly Asn Phe His Pro Tyr Ser Asp Asp
                 65                  70                  75

ACA AAT TAT AAC GAG AAA TTT AAG GGC AAG GCT AAG CTG ACC GTA GAC        291
Thr Asn Tyr Asn Glu Lys Phe Lys Gly Lys Ala Lys Leu Thr Val Asp
                 80                  85                  90

ACC TCT ACA AAC ACC GCC TAC ATG GAA CTG TCC AGC CTG CGC TCC GAG        339
Thr Ser Thr Asn Thr Ala Tyr Met Glu Leu Ser Ser Leu Arg Ser Glu
             95                  100                 105
```

```
GAC ACT GCA GTC TAC TAC TGC GCC ATA CAC TAC GGT AGT GCC TAC GCT      387
Asp Thr Ala Val Tyr Tyr Cys Ala Ile His Tyr Gly Ser Ala Tyr Ala
    110                 115                 120

ATG GAC TAT TGG GGA CAG GGT ACC CTT GTC ACC GTC AGT TCA              429
Met Asp Tyr Trp Gly Gln Gly Thr Leu Val Thr Val Ser Ser
125                 130                 135

GGTGAGTGGA TCC                                                        442
```

(2) INFORMATION FOR SEQ ID NO:44:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO:44:

```
Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Thr Tyr Pro Ile Glu Trp Met Lys Gln Asn Pro Gly Gln Gly Leu
    50                  55                  60

Glu Trp Ile Gly Asn Phe His Pro Tyr Ser Asp Asp Thr Asn Tyr Asn
65                  70                  75                  80

Glu Lys Phe Lys Gly Lys Ala Lys Leu Thr Val Asp Thr Ser Thr Asn
                85                  90                  95

Thr Ala Tyr Met Glu Leu Ser Ser Leu Arg Ser Glu Asp Thr Ala Val
            100                 105                 110

Tyr Tyr Cys Ala Ile His Tyr Gly Ser Ala Tyr Ala Met Asp Tyr Trp
        115                 120                 125

Gly Gln Gly Thr Leu Val Thr Val Ser Ser
130                 135
```

(2) INFORMATION FOR SEQ ID NO:45:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..53

(xi) SEQUENCE DESCRIPTION: SEQ ID NO:45:

```
AAC TAT AAC GAG ATC TTT AAG GGC AAG GCT ACA ATG ACC GCA GAC ACC      48
Asn Tyr Asn Glu Ile Phe Lys Gly Lys Ala Thr Met Thr Ala Asp Thr
1               5                   10                  15

TCT AC                                                                53
Ser
```

(2) INFORMATION FOR SEQ ID NO:46:

(i) SEQUENCE CHARACTERISTICS:
        (A) LENGTH: 17 amino acids
        (B) TYPE: amino acid (D) TOPOLOGY: linear (ii) MOLECULE TYPE: protein (xi) SEQUENCE DESCRIPTION: SEQ ID NO:46:

Asn Tyr Asn Glu Ile Phe Lys Gly Lys Ala Thr Met Thr Ala Asp Thr
1               5                  10                  15

Ser (2) INFORMATION FOR SEQ ID NO:47:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..65

(xi) SEQUENCE DESCRIPTION: SEQ ID NO:47:

GTC TAC TAC TGC TCA AGG GGG ATA CCG GGA TAC GCT ATG GAC TAT TGG        48
Val Tyr Tyr Cys Ser Arg Gly Ile Pro Gly Tyr Ala Met Asp Tyr Trp
1               5                  10                  15

GGA CAG GGT ACC CTT  GT                                               65
Gly Gln Gly Thr Leu
            20

(2) INFORMATION FOR SEQ ID NO:48:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:48:

Val Tyr Tyr Cys Ser Arg Gly Ile Pro Gly Tyr Ala Met Asp Tyr Trp
1               5                  10                  15

Gly Gln Gly Thr Leu
            20

(2) INFORMATION FOR SEQ ID NO:49:

(i) SEQUENCE CHARACTERISTICS:
        (A) LENGTH: 524 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 14..58

(ix) FEATURE:
        (A) NAME/KEY: CDS
        (B) LOCATION: 141..485

(xi) SEQUENCE DESCRIPTION: SEQ ID NO:49:

AAGCTTCGCC ACC ATG GGA TGG AGC TGT ATC ATC CTC TTC TTG GTA GCA        49
           Met Gly Trp Ser Cys Ile Ile Leu Phe Leu Val Ala
           1               5                  10

```
ACA GCT ACA GGTAAGGGGC TCACAGTAGC AGGCTTGAGG TCTGGACATA          98
Thr Ala Thr
        15

TATATGGGTG ACAATGACAT CCACTTTGCC TTTCTCTCCA CA GGT GTC CAC TCC  152
                                              Gly Val His Ser
                                               1

GAC ATC CAG ATG ACC CAG AGC CCA AGC AGC CTG AGC GCC AGC GTG GGT 200
Asp Ile Gln Met Thr Gln Ser Pro Ser Ser Leu Ser Ala Ser Val Gly
 5              10              15              20

GAC AGA GTG ACC ATC ACC TGT AAG GCC AGC CAA AGT GTT GAT TAT GAT 248
Asp Arg Val Thr Ile Thr Cys Lys Ala Ser Gln Ser Val Asp Tyr Asp
            25              30              35

GGT GAT AGT TAT ATG AAC TGG TAC CAG CAG AAG CCA GGT AAG GCT CCA 296
Gly Asp Ser Tyr Met Asn Trp Tyr Gln Gln Lys Pro Gly Lys Ala Pro
        40              45              50

AAG CTG CTG ATC TAC GCT GCA TCC AAT CTA GAA TCT GGT GTG CCA AGC 344
Lys Leu Leu Ile Tyr Ala Ala Ser Asn Leu Glu Ser Gly Val Pro Ser
    55              60              65

AGA TTC AGC GGT AGC GGT AGC GGT ACC GAC TTC ACC TTC ACC ATC AGC 392
Arg Phe Ser Gly Ser Gly Ser Gly Thr Asp Phe Thr Phe Thr Ile Ser
70              75              80

AGC CTC CAG CCA GAG GAC ATC GCC ACC TAC TAC TGC CAG CAA AGT AAT 440
Ser Leu Gln Pro Glu Asp Ile Ala Thr Tyr Tyr Cys Gln Gln Ser Asn
85              90              95              100

GAG GAC CCA TGG ACG TTC GGC CAA GGG ACC AAG GTG GAA ATC AAA     485
Glu Asp Pro Trp Thr Phe Gly Gln Gly Thr Lys Val Glu Ile Lys
            105             110             115

CGTGAGTAGA ATTTAAACTT TGCTTCCTCA GTTGGATCC                      524

(2) INFORMATION FOR SEQ ID NO:50:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:50:

Met Gly Trp Ser Cys Ile Ile Leu Phe Leu Val Ala Thr Ala Thr
 1               5                  10                  15

(2) INFORMATION FOR SEQ ID NO:51:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO:51:

Gly Val His Ser Asp Ile Gln Met Thr Gln Ser Pro Ser Ser Leu Ser
 1               5                  10                  15

Ala Ser Val Gly Asp Arg Val Thr Ile Thr Cys Lys Ala Ser Gln Ser
                20                  25                  30

Val Asp Tyr Asp Gly Asp Ser Tyr Met Asn Trp Tyr Gln Gln Lys Pro
            35                  40                  45

Gly Lys Ala Pro Lys Leu Leu Ile Tyr Ala Ala Ser Asn Leu Glu Ser
        50                  55                  60

Gly Val Pro Ser Arg Phe Ser Gly Ser Gly Ser Gly Thr Asp Phe Thr
65                  70                  75                  80
```

```
Phe Thr Ile Ser Ser Leu Gln Pro Glu Asp Ile Ala Thr Tyr Tyr Cys
                85                  90                  95

Gln Gln Ser Asn Glu Asp Pro Trp Thr Phe Gly Gln Gly Thr Lys Val
            100                 105                 110

Glu Ile Lys
        115
```

(2) INFORMATION FOR SEQ ID NO:52:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..79

(xi) SEQUENCE DESCRIPTION: SEQ ID NO:52:

```
C AGA GTG ACC ATG AGC TGT AAG TCC AGC CAA AGT CTG TTA AAC AGT           46
  Arg Val Thr Met Ser Cys Lys Ser Ser Gln Ser Leu Leu Asn Ser
  1               5                  10                  15

GGA GAT CAA AAG AAC TAC TTG ACC TGG TAC CAG C                           80
Gly Asp Gln Lys Asn Tyr Leu Thr Trp Tyr Gln
            20                  25
```

(2) INFORMATION FOR SEQ ID NO:53:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:53:

```
Arg Val Thr Met Ser Cys Lys Ser Ser Gln Ser Leu Leu Asn Ser Gly
1               5                  10                  15

Asp Gln Lys Asn Tyr Leu Thr Trp Tyr Gln
            20                  25
```

(2) INFORMATION FOR SEQ ID NO:54:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..96

(xi) SEQUENCE DESCRIPTION: SEQ ID NO:54:

```
CAG CAG AAG CCA GGT AAG GCT CCA AAG CTG CTG ATC TAC TGG GCA TCC         48
Gln Gln Lys Pro Gly Lys Ala Pro Lys Leu Leu Ile Tyr Trp Ala Ser
1               5                  10                  15

ACT GGG GAA TCT GGT GTG CCA AGC AGA TTC AGC GGT AGC GGT AGC GGT         96
Thr Gly Glu Ser Gly Val Pro Ser Arg Phe Ser Gly Ser Gly Ser Gly
            20                  25                  30

AC                                                                       98
```

(2) INFORMATION FOR SEQ ID NO:55:

(i) SEQUENCE CHARACTERISTICS:
        (A) LENGTH: 32 amino acids
        (B) TYPE: amino acid
        (D) TOPOLOGY: linear (ii) MOLECULE TYPE: protein (xi) SEQUENCE DESCRIPTION: SEQ ID NO:55:

```
Gln Gln Lys Pro Gly Lys Ala Pro Lys Leu Leu Ile Tyr Trp Ala Ser
 1               5                  10                  15

Thr Gly Glu Ser Gly Val Pro Ser Arg Phe Ser Gly Ser Gly Ser Gly
                20                  25                  30
```

(2) INFORMATION FOR SEQ ID NO:56:

(i) SEQUENCE CHARACTERISTICS:
        (A) LENGTH: 103 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..103

(xi) SEQUENCE DESCRIPTION: SEQ ID NO:56:

```
T AGC GGT ACC GAC TTC ACC TTC ACC ATC AGC AGC CTC CAG CCA GAG        46
  Ser Gly Thr Asp Phe Thr Phe Thr Ile Ser Ser Leu Gln Pro Glu
  1               5                  10                  15

GAC ATC GCC ACC TAC TAC TGT CAG AAT GAT TAT AGT TAC CCA TGG ACG      94
Asp Ile Ala Thr Tyr Tyr Cys Gln Asn Asp Tyr Ser Tyr Pro Trp Thr
                20                  25                  30

TTC GGC CAA                                                         103
Phe Gly Gln
```

(2) INFORMATION FOR SEQ ID NO:57:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION: SEQ ID NO:57:

```
Ser Gly Thr Asp Phe Thr Phe Thr Ile Ser Ser Leu Gln Pro Glu Asp
 1               5                  10                  15

Ile Ala Thr Tyr Tyr Cys Gln Asn Asp Tyr Ser Tyr Pro Trp Thr Phe
                20                  25                  30

Gly Gln
```

(2) INFORMATION FOR SEQ ID NO:58:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:

(A) NAME/KEY: Peptide
            (B) LOCATION: 1
            (D) OTHER INFORMATION: /note= "Xaa at 1 = Ala, Ile, Leu,
                Met, Asn, Pro, Gln, Ser, Thr, Val or Tyr; Xaa at 4 = Gly or Ala;
                Xaa at 6 = Ala, Cys, Asp, Glu, Gly,His, Ile, Lys, Leu, Met, Asn,
                Gln, Arg, Ser, Thr, Val, Trp or Tyr."

(xi) SEQUENCE DESCRIPTION: SEQ ID NO:58:

Xaa Gly Pro Xaa Arg Xaa
1               5

(2) INFORMATION FOR SEQ ID NO:59:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa = Ala, Ile, Leu, Met,
            Asn, Pro, Gln, Ser, Thr, Val, Tyr"

(xi) SEQUENCE DESCRIPTION: SEQ ID NO:59:

Xaa Gly Pro Gly Arg Ala
1               5

(2) INFORMATION FOR SEQ ID NO:60:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Xaa = Ala, Cys, Asp, Glu,
            Gly, His, Ile, Lys, Leu, Met, Asn, Gln, Arg, Ser, Thr, Val, Trp,
            Tyr"

(xi) SEQUENCE DESCRIPTION: SEQ ID NO:60:

Ile Gly Pro Gly Arg Xaa
1               5

(2) INFORMATION FOR SEQ ID NO:61:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:61:

Val Gly Pro Gly Arg Thr
1               5

(2) INFORMATION FOR SEQ ID NO:62:

(i) SEQUENCE CHARACTERISTICS:
        (A) LENGTH: 6 amino acids
        (B) TYPE: amino acid (C) STRANDEDNESS: single
          (D) TOPOLOGY: linear (ii) MOLECULE TYPE: peptide (xi) SEQUENCE DESCRIPTION: SEQ ID NO:62:

Val Gly Pro Gly Arg Ser
1               5

(2) INFORMATION FOR SEQ ID NO:63:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:63:

Ile Gly Pro Ala Arg Ala
1               5

(2) INFORMATION FOR SEQ ID NO:64:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:64:

Asn Asn Thr Arg Lys Gly Ile Arg Ile Gly Pro Gly Arg Ala Val Tyr
1               5                   10                  15

Ala Thr Gly Lys
            20

(2) INFORMATION FOR SEQ ID NO:65:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:65:

Asn Asn Thr Arg Lys Arg Val Thr Met Gly Pro Gly Arg Val Tyr Tyr
1               5                   10                  15

Thr Thr Gly Glu
            20

(2) INFORMATION FOR SEQ ID NO:66:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:66:

Asn Asn Thr Arg Lys Ser Ile Thr Lys Gly Pro Gly Arg Val Ile Tyr
1               5                   10                  15

Ala Thr Gly Gln
        20

(2) INFORMATION FOR SEQ ID NO:67:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:67:

Asn Asn Thr Arg Lys Arg Ile Thr Thr Gly Pro Gly Arg Val Tyr Tyr
1               5                   10                  15

Thr Thr Gly Glu
        20

(2) INFORMATION FOR SEQ ID NO:68:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:68:

Gly Pro Gly Arg Gly Pro Gly Arg Gly Pro Gly Arg Gly Pro Gly Arg
1               5                   10                  15

Gly Pro Gly Arg
        20

(2) INFORMATION FOR SEQ ID NO:69:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:69:

GCCGGATCCA CACATGGAAT TAGGCCAGTA                                30

(2) INFORMATION FOR SEQ ID NO:70:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:70:

GCTCTGCAGT CAAATTTCTG GGTCCCCTCC TGA                            33

(2) INFORMATION FOR SEQ ID NO:71:

(i) SEQUENCE CHARACTERISTICS:
        (A) LENGTH: 23 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:71:

Asn Asn Thr Arg Lys Ser Ile Pro Ile Gly Pro Gly Arg Ala Phe Tyr
1               5                  10                  15

Thr Thr Gly Glu Ile Ile Gly
            20

(2) INFORMATION FOR SEQ ID NO:72:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:72:

Asn Asn Thr Arg Lys Ser Ile Pro Ile Gly Pro Gly Arg Ala Phe Tyr
1               5                  10                  15

Thr Thr Gly Glu Val Ile Gly
            20

(2) INFORMATION FOR SEQ ID NO:73:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:73:

Asn Asn Thr Arg Lys Gly Ile Pro Ile Gly Pro Gly Arg Ala Phe Tyr
1               5                  10                  15

Thr Thr Gly Glu Ile Ile Gly
            20

(2) INFORMATION FOR SEQ ID NO:74:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:74:

Asn Asn Thr Arg Lys Ser Ile His Ile Gly Pro Gly Arg Ala Phe Tyr
1               5                  10                  15

Thr Thr Gly Glu Ile Ile Gly
            20

(2) INFORMATION FOR SEQ ID NO:75:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:75:

Asn Asn Thr Arg Lys Ser Ile His Ile Gly Pro Gly Arg Ala Phe Tyr
1               5                   10                  15

Thr Thr Gly Glu Ile Met Gly
            20

(2) INFORMATION FOR SEQ ID NO:76:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:76:

Asn Asn Thr Arg Lys Gly Ile Tyr Ile Gly Pro Gly Arg Ala Val Tyr
1               5                   10                  15

Thr Thr Glu Arg Ile Ile Gly
            20

(2) INFORMATION FOR SEQ ID NO:77:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

Asn Asn Thr Arg Lys Gly Ile Tyr Ile Gly Pro Gly Arg Ala Val Tyr
1               5                   10                  15

Thr Thr Gly Arg Ile Ile Gly
            20

(2) INFORMATION FOR SEQ ID NO:78:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:78:

Asp Ile Thr Pro Gly Gly Gly Thr Arg Asn Thr Asn Gln Ile Phe Lys
1               5                   10                  15

Gly (2) INFORMATION FOR SEQ ID NO:79:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..354

(xi) SEQUENCE DESCRIPTION: SEQ ID NO:79:

| CAG | GTG | CAA | CTA | GTG | CAG | TCC | GGC | GCC | GAA | GTG | AAG | AAA | CCC | GGT | GCT | 48 |
|---|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala | |
| 1 | | | | 5 | | | | | 10 | | | | | 15 | | |

| TCC | GTG | AAG | GTG | AGC | TGT | AAA | GCT | AGC | GGT | TAT | ACC | TTC | ACT | AAC | TCC | 96 |
|---|---|---|---|---|---|---|---|---|---|---|---|---|---|---|---|---|
| Ser | Val | Lys | Val | Ser | Cys | Lys | Ala | Ser | Gly | Tyr | Thr | Phe | Thr | Asn | Ser | |
| | | | 20 | | | | | 25 | | | | | 30 | | | |

| TGG | ATA | GGT | TGG | TTT | AGA | CAG | GCC | CCA | GGC | CAA | GGG | CTC | GAG | TGG | ATT | 144 |
|---|---|---|---|---|---|---|---|---|---|---|---|---|---|---|---|---|
| Trp | Ile | Gly | Trp | Phe | Arg | Gln | Ala | Pro | Gly | Gln | Gly | Leu | Glu | Trp | Ile | |
| | | 35 | | | | | 40 | | | | | 45 | | | | |

| GGC | GAT | ATT | TAC | CCT | GGA | GGT | GGC | TAT | ACA | AAC | TAT | AAC | GAG | ATC | TTT | 192 |
|---|---|---|---|---|---|---|---|---|---|---|---|---|---|---|---|---|
| Gly | Asp | Ile | Tyr | Pro | Gly | Gly | Gly | Tyr | Thr | Asn | Tyr | Asn | Glu | Ile | Phe | |
| 50 | | | | | 55 | | | | | 60 | | | | | | |

| AAG | GGC | AAG | GCT | ACA | ATG | ACC | GCA | GAC | ACC | TCT | ACA | AAC | ACC | GCC | TAC | 240 |
|---|---|---|---|---|---|---|---|---|---|---|---|---|---|---|---|---|
| Lys | Gly | Lys | Ala | Thr | Met | Thr | Ala | Asp | Thr | Ser | Thr | Asn | Thr | Ala | Tyr | |
| 65 | | | | | 70 | | | | | 75 | | | | | 80 | |

| ATG | GAA | CTG | TCC | AGC | CTG | CGC | TCC | GAG | GAC | ACT | GCA | GTC | TAC | TAC | TGC | 288 |
|---|---|---|---|---|---|---|---|---|---|---|---|---|---|---|---|---|
| Met | Glu | Leu | Ser | Ser | Leu | Arg | Ser | Glu | Asp | Thr | Ala | Val | Tyr | Tyr | Cys | |
| | | | | 85 | | | | | 90 | | | | | 95 | | |

| TCA | AGG | GGG | ATA | CCG | GGA | TAC | GCT | ATG | GAC | TAT | TGG | GGA | CAG | GGT | ACC | 336 |
|---|---|---|---|---|---|---|---|---|---|---|---|---|---|---|---|---|
| Ser | Arg | Gly | Ile | Pro | Gly | Tyr | Ala | Met | Asp | Tyr | Trp | Gly | Gln | Gly | Thr | |
| | | | 100 | | | | | 105 | | | | | 110 | | | |

| CTT | GTC | ACC | GTC | AGT | TCA | | | | | | | | | | | 354 |
|---|---|---|---|---|---|---|---|---|---|---|---|---|---|---|---|---|
| Leu | Val | Thr | Val | Ser | Ser | | | | | | | | | | | |
| | | 115 | | | | | | | | | | | | | | |

(2) INFORMATION FOR SEQ ID NO:80:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:80:

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Ser
            20                  25                  30

Trp Ile Gly Trp Phe Arg Gln Ala Pro Gly Gln Gly Leu Glu Trp Ile
        35                  40                  45

Gly Asp Ile Tyr Pro Gly Gly Gly Tyr Thr Asn Tyr Asn Glu Ile Phe
    50                  55                  60

Lys Gly Lys Ala Thr Met Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ser Arg Gly Ile Pro Gly Tyr Ala Met Asp Tyr Trp Gly Gln Gly Thr
            100                 105                 110

Leu Val Thr Val Ser Ser
        115

(2) INFORMATION FOR SEQ ID NO:81:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: CDS
    (B) LOCATION: 1..339

(xi) SEQUENCE DESCRIPTION: SEQ ID NO:81:

```
GAC ATC CAG ATG ACC CAG AGC CCA AGC AGC CTG AGC GCC AGC GTG GGT      48
Asp Ile Gln Met Thr Gln Ser Pro Ser Ser Leu Ser Ala Ser Val Gly
 1               5                  10                  15

GAC AGA GTG ACC ATG AGC TGT AAG TCC AGC CAA AGT CTG TTA AAC AGT      96
Asp Arg Val Thr Met Ser Cys Lys Ser Ser Gln Ser Leu Leu Asn Ser
                20                  25                  30

GGA GAT CAA AAG AAC TAC TTG ACC TGG TAC CAG CAG AAG CCA GGT AAG     144
Gly Asp Gln Lys Asn Tyr Leu Thr Trp Tyr Gln Gln Lys Pro Gly Lys
            35                  40                  45

GCT CCA AAG CTG CTG ATC TAC TGG GCA TCC ACT GGG GAA TCT GGT GTG     192
Ala Pro Lys Leu Leu Ile Tyr Trp Ala Ser Thr Gly Glu Ser Gly Val
 50                  55                  60

CCA AGC AGA TTC AGC GGT AGC GGT AGC GGT ACC GAC TTC ACC TTC ACC     240
Pro Ser Arg Phe Ser Gly Ser Gly Ser Gly Thr Asp Phe Thr Phe Thr
 65                  70                  75                  80

ATC AGC AGC CTC CAG CCA GAG GAC ATC GCC ACC TAC TAC TGT CAG AAT     288
Ile Ser Ser Leu Gln Pro Glu Asp Ile Ala Thr Tyr Tyr Cys Gln Asn
                85                  90                  95

GAT TAT AGT TAC CCA TGG ACG TTC GGC CAA GGG ACC AAG GTG GAA ATC     336
Asp Tyr Ser Tyr Pro Trp Thr Phe Gly Gln Gly Thr Lys Val Glu Ile
            100                 105                 110

AAA                                                                 339
Lys
```

(2) INFORMATION FOR SEQ ID NO:82:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:82:

```
Asp Ile Gln Met Thr Gln Ser Pro Ser Ser Leu Ser Ala Ser Val Gly
 1               5                  10                  15

Asp Arg Val Thr Met Ser Cys Lys Ser Ser Gln Ser Leu Leu Asn Ser
                20                  25                  30

Gly Asp Gln Lys Asn Tyr Leu Thr Trp Tyr Gln Gln Lys Pro Gly Lys
            35                  40                  45

Ala Pro Lys Leu Leu Ile Tyr Trp Ala Ser Thr Gly Glu Ser Gly Val
 50                  55                  60

Pro Ser Arg Phe Ser Gly Ser Gly Ser Gly Thr Asp Phe Thr Phe Thr
 65                  70                  75                  80

Ile Ser Ser Leu Gln Pro Glu Asp Ile Ala Thr Tyr Tyr Cys Gln Asn
                85                  90                  95

Asp Tyr Ser Tyr Pro Trp Thr Phe Gly Gln Gly Thr Lys Val Glu Ile
            100                 105                 110

Lys
```

(2) INFORMATION FOR SEQ ID NO:83:

(i) SEQUENCE CHARACTERISTICS:

(A) LENGTH: 62 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:83:

CCCTTAAAGA TCTCGTTATA GTTTGTATAG CCACCTCCAG GGTAAATATC GCCAATCCAC    60

TC    62

(2) INFORMATION FOR SEQ ID NO:84:

(i) SEQUENCE CHARACTERISTICS:
(A) LENGTH: 65 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:84:

ACAAGGGTAC CCTGTCCCCA ATAGTCCATA GCGTATCCCG GTATCCCCCT TGAGCAGTAG    60

TAGAC    65

(2) INFORMATION FOR SEQ ID NO:85:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:85:

GCTGGTACCA GGTCAAGTAG TTCTTTTGAT CTCCACTGTT TAACAGACTT TGGCTGGACT    60

TACAGCTCAT GGTCACTCTG    80

(2) INFORMATION FOR SEQ ID NO:86:

(i) SEQUENCE CHARACTERISTICS:
(A) LENGTH: 98 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:86:

CGCTACCGCT ACCGCTGAAT CTGCTTGGCA CACCAGATTC CCCAGTGGAT GCCCAGTAGA    60

TCAGCAGCTT TGGAGCCTTA CCTGGCTTCT GCTGGTAC    98

ANTI-HIV MONOCLONAL ANTIBODY

This application is a 371 of P.C.T. JP94/00371 filed Mar. 9, 1994.

TECHNICAL FIELD

The present invention relates to an immunological technique which provides a novel substance useful for prevention, treatment, diagnosis of viral infection, and for study of biochemistry and histology. More particularly, it relates to a monoclonal antibody having a broad neutralization spectrum against human immunodeficiency virus (HIV), a causative virus of acquired immunodeficiency syndrome (AIDS), a hybridoma secreting said antibody and a process for preparing the same.

The present invention further relates to a humanized recombinant monoclonal antibody for clinical application.

BACKGROUND ART

Human immunodeficiency virus (HIV) is a human retrovirus which causes a series of diseases such as acquired immunodeficiency syndrome (AIDS) and AIDS related complexes (ARC). Today, these diseases have become a serious problem in the world, but no vaccines or established therapies effective for these diseases have been provided.

As an anti-viral agent against HIV, reverse transcriptase inhibitors of nucleic acid analogues such as 3'-azido-2', 3'-dideoxythymidin (AZT) or 2',3'-dideoxyinosin (ddI) have been used, and thereby therapeutic efficacy such as inhibition of viral growth, increase in the number of CD4-positive cells and prolongation of life span has been observed. However, in most cases, therapeutic efficacy of these drugs to AIDS is partial or temporal, and in addition, these drugs exhibit toxicity or growth inhibition to hematopoietic cells, and thereby inhibit reconstruction of an immune system which has become deficient. From these points of view, development of more effective anti-HIV agents has been desired.

An antibody is an important protein which plays a role in an immune reaction in mammals including humans and has a function to neutralize and remove foreign substances invaded from outside or substances recognized as foreign substances by the living body. In this respect, an antibody is expected to be useful for treatment of infectious diseases.

Karpas et al. observed remission of clinical symptoms after administration of anti-HIV antibodies derived from healthy patients infected with HIV to AIDS patients (Proc. Natl. Acad. Sci. USA, 85, p.9234 (1989), Proc. Natl. Acad. Sci. USA, 87, p. 7613 (1990)). Jackson et al. also obtained similar results (Lancet, 2, p. 647 (1988)). These results show usefulness of an antibody therapy in AIDS.

Apart from such passive immunotherapy, an active immunization of patients with a component vaccine of HIV has also been attempted in order to enhance immune capacity (AIDS Res. Hum. Retroviruses, 8, P1051 (1992)). This treatment was found to be effective to patients who have not yet developed symptoms, but did not show significant effect in patients who developed AIDS with a decreased number of CD4-positive cells since they are deficient in active immune response. Accordingly, in case of those patients whose disease has progressed, one cannot but rely on passive immunotherapy, and hence, a neutralizing antibody has a great significance.

Epitopes recognized by an antibody neutralizing HIV are located in a glycoprotein antigen having a molecular weight of about $1.2 \times 10^5$ daltons (gp120) present on a coating membrane of HIV, a transmembrane glycoprotein antigen having a molecular weight of about $4.1 \times 10^4$ daltons (gp41) and a nuclear protein antigen having a molecular weight of about $1.7 \times 10^4$ daltons (p17). Among these epitopes, that located in the third variable region (V3) of gp120(amino acid number 303-338), which is also referred to as Principal Neutralization Determinant (PND), can induce a potent neutralizing antibody, and hence, is a major target in developing medicaments or vaccines.

Although a correct role of PND region in viral infection remains still unknown, it is assumed to help invasion of viruses after binding between gp120 and CD4. PND region also plays an important role in formation of multinuclear giant cells by CD4-positive cells. Accordingly, if an antibody which binds to this region and inhibits infection and growth of viruses is prepared, this can possibly be an effective anti-HIV agent.

However, since PND region shows a high variability in amino acid sequence as compared to other epitopes in gp120, most of monoclonal antibodies which recognize this region are viral strain-specific neutralizing antibody which recognizes only a specific HIV strain. If such strain-specific monoclonal antibody is used for treatment or prevention, its efficacy is restricted to those patients who are infected with HIV strain that can be neutralized with that antibody. Furthermore, in a individual HIV-infected patient, HIV is never present as a single HIV strain but usually as quasispecies of many HIV variants whose amino acid sequence show several % variation.

Therefore, possibility of a monoclonal antibody as a medicament is closely related to what extent of many HIV variants present in patients or within a single patient said antibody can bind to and neutralize, i.e. a range of neutralization spectrum of antibody. In order to obtain a clinically useful HIV medicament, a monoclonal antibody having as broad neutralization spectrum as possible is preferably established.

DISCLOSURE OF THE INVENTION

An object of the present invention is to provide an monoclonal antibody which recognizes the above PND region of HIV and has a broad neutralization spectrum and a hybridoma which is capable of producing said antibody, and further to provide a chimeric or humanized antibody which is prepared from said monoclonal antibody for administration to humans and a process for preparing the same. The present inventors have studied PND region of viruses obtained from many HIV-infected individuals, and as a result, have revealed that the so-called PND-Tip region, said region including Gly-Pro-Gly-Arg (residues 15–18 of SEQ ID NO: 1, hereinafter "GPGR") sequence present in the central area of PND region, is relatively conserved although some regions show high variability in amino acid sequence (AIDS Res. Human Retroviruses, 7 p.825 (1991)) . Therefore, if there can be prepared an antibody which recognizes this conserved region, it is expected to be a clinically effective monoclonal antibody capable of neutralizing many kinds of viral strains.

However, it is foreseeable that such antibody recognizing this region can only be prepared with a low efficiency. Boudet et al. (Int. Immunol., 4, p.283 (1992)) suggested, within in PND region, high immunogenicity is shown by a basic amino acid residing outside the above-mentioned but the immunogenicity of GPGR sequence is low. The fact that most antibodies recognizing PND region are strain-specific also suggests that antibody-producing cells which produce an antibody having a broad neutralization spectrum as mentioned above are scarce in HIV-infected patients or animals (mouse etc.) immunized with HIV antigens. Accordingly, it is required to increase the number of cells which produce said antibody in any way.

Under the circumstances, the present inventors have provided a novel method for immunization as will be discussed hereinbelow and thereby succeeded in positive derivation of anti-HIV antibodies which recognize PND-Tip region. That is, a test animal is firstly immunized with one strain of HIV which includes GPGR sequence. Then, the second and the following immunizations are conducted sequentially with another HIV strains which also contain GPGR sequence of PND region in common but have different amino acid sequences at the side of the N and C termini from those of the HIV strain used for the first immunization. An antigen for immunization includes a viral particle, an infected cell, a purified gp120, gp120 with a suitable treatment (e.g. with enzymatic treatment), or a peptide synthesized based on the amino acid sequence of PND region and a derivative thereof etc. Among these, a synthetic peptide comprising an amino acid sequence of PND region or a conjugate thereof with a serum albumin or keyhole limpet hemocyanin (KLH) etc. are preferable for inducing immunization which is limited within PND region. A mouse used for immunization includes BALB/c, C57BL/6, C3H/HeN, and F1 mouse therefrom. Immunization is conducted using 20 to 200 $\mu$g of an antigen per one mouse (4 to 8 weeks old, weighing 20 to 30 g) four to seven times with an interval of 1 to 2 weeks.

With such immunization procedure, as a result of a booster effect of the second and the following immunizations, antibody-producing cells which produce an antibody that recognizes an overlapping region of the antigens used for the first, the second and the following immunizations, i.e. PND-Tip region, should increase in a population of antibody-producing cells which are induced within the living body of the immunized animal. Spleen cells of this immunized mouse can be used as a material for cell fusion in order to efficiently produce the desired antibody-producing cells.

Without using a cell fusion technique, monoclonal antibody-producing cells may be produced by another method which comprises transforming B cells from HIV-infected patients with Epstein-Barr virus (EBV), and converting said antibody-producing cells into monoclonal antibody-producible one. However, this method is not suitable for the method of the present invention since the source of antibody-producing cells is peripheral blood in case of the method of the present invention, and hence, the materials are hardly available. In addition, this method is not an efficient method since most of neutralizing antibodies found in HIV-infected individuals are strain-specific antibodies whereas antibodies recognizing the above-mentioned PND-Tip region are quite rare. On the contrary, a hybridoma method is advantageous in that it employs an experimental animal such as mouse to allow for an immunogen being readily available and for devising the above-mentioned immunization procedure. Accordingly, for positively inducing the desired monoclonal antibody-producing cells (recognizing PND-Tip region); a hybridoma method can efficiently be used in the present invention.

BRIEF EXPLANATION OF DRAWINGS

FIG. 1 shows a reactivity between anti-serum obtained from mouse sequentially immunized with multiple PND peptides (SP-1, SP-17, SP-11, SP-12, SP-14, SP-30) and each of V3 peptides.

FIG. 2 shows a reactivity between anti-serum obtained from mouse sequentially immunized with a single PND peptide (SP-1) and each of V3 peptides.

FIG. 3 shows an activity of the monoclonal antibody C25 of the present invention and of the strain-specific neutralizing antibodies $\mu$5.5, $\alpha$64 to inhibit infection of various HIV variants (infection by cell-free viruses and cell-to-cell infection). The sequences in the column headed "Amino acid sequence of PND" are SEQ ID NOS: 1–14, respectively FIG. 4 shows a reactivity of C25 antibody with various PND peptides.

FIG. 5 shows a reactivity of $\mu$5.5 antibody with various PND peptides.

FIGS. 6A–C shows a reactivity of C25 antibody with the full decapeptide ("No") and each ten nonapeptides which are obtained by deleting each one amino acid from decapeptides Ile-His-Ile-Gly-Pro-Gly-Arg-Ala-Phe-Tyr (residues 12–21 of SEQ ID NO: 1, hereinafter "IHIGPGRAFY") derived from MN, Ile-Arg-Val-Gly-Pro-Gly-Arg-Ala-Ile-Tyr (residues 12–21 of SEQ ID NO: 5, hereinafter "IRVGPGRAIY") derived from NI54-2 and Ile-Arg-Val-Gly-Pro-Gly-Arg-Thr-Leu-Tyr (residues 12–21 of SEQ ID NO: 9, hereinafter "IRVGPGRTLY") derived from NI53 respectively.

FIG. 7 shows a reactivity of C25 antibody with overlapped peptide groups comprising 3 to 10 amino acids (a series of peptides having an amino acid sequence shifted one by one from the N terminus) which are prepared based on the MN-derived peptide. The peptide group specifically labelled as IGPGRA is residues 14–19 of SEQ ID NO: 1.

FIG. 8 shows a reactivity of C25 antibody with decapeptides which are obtained by substituting the 1st amino acid (I) in the MN-derived peptide IHIGPGRAFY with other amino acids.

FIG. 9 shows a reactivity of C25 antibody with decapeptides which are obtained by substituting the 2nd amino acid (H) in the MN-derived peptide IHIGPGRAFY with other amino acids.

FIG. 10 shows a reactivity of C25 antibody with decapeptides which are obtained by substituting the 3rd amino acid (I) in the MN-derived peptide IHIGPGRAFY with other amino acids.

FIG. 11 shows a reactivity of C25 antibody with decapeptides which are obtained by substituting the 4th amino acid (G) in the MN-derived peptide IHIGPGRAFY with other amino acids.

FIG. 12 shows a reactivity of C25 antibody with decapeptides which are obtained by substituting the 5th amino acid (P) in the MN-derived peptide IHIGPGRAFY with other amino acids.

FIG. 13 shows a reactivity of C25 antibody with decapeptides which are obtained by substituting the 6th amino acid (G) in the MN-derived peptide IHIGPGRAFY with other amino acids.

FIG. 14 shows a reactivity of C25 antibody with decapeptides which are obtained by substituting the 7th amino acid (R) in the MN-derived peptide IHIGPGRAFY with other amino acids.

FIG. 15 shows a reactivity of C25 antibody with decapeptides which are obtained by substituting the 8th amino acid (A) in the MN-derived peptide IHIGPGRAFY with other amino acids.

FIG. 16 shows a reactivity of C25 antibody with decapeptides which are obtained by substituting the 9th amino acid (F) in the MN-derived peptide IHIGPGRAFY with other amino acids.

FIG. 17 shows a reactivity of C25 antibody with decapeptides which are obtained by substituting the 10th amino acid (Y) in the MN-derived peptide IHIGPGRAFY with other amino acids.

FIG. 18 shows a reactivity between consensus PND peptides derived from HIV-infected individuals in Japan and C25 antibody in comparison with those of μ5.5 and α64. The PND sequences of the 31 lines of FIG. 18 are SEQ ID NOS: 1, 15, 2, 16, 17, 13, 10, 11, 18, 19, 14, 20, 21, 7, 6, 22, 5, 23, 8, 9, 24, 25, 4, 26, 27, 28, 29, 30, 12, 31 and 32, respectively.

FIG. 19 shows nucleic acid (SEQ ID NO: 33) and amino acid (SEQ ID NO: 34) sequences of H chain variable region of C25 antibody.

FIG. 20 shows nucleic acid (SEQ ID NO: 35) and amino acid (SEQ ID NO: 36) sequences of L chain variable region of C25 antibody.

FIG. 21 shows a nucleic acid sequence (SEQ ID NO: 37) at the 5' terminus of a gene of H chain variable region of humanized C25 antibody (RC25) and an amino acid sequence (SEQ ID NO: 38) at the N terminus thereof. The nucleotide sequences, SEQ ID NO: 39 and SEQ ID NO: 83, are shown for primers #1 and #2, respectively, along with the corresponding mutated amino acid sequences (SEQ ID NOS: 40 and 42) in the region of the primers. SEQ ID NO: 41 is the nucleotide sequence complementary to primer #2.

FIG. 22 shows a nucleic acid sequence (SEQ ID NO: 43) at the 3' terminus of a gene of H chain variable region of humanized C25 antibody (RC25) and an amino acid sequence (SEQ ID NO: 44) at the C terminus thereof. The nucleotide sequences, SEQ ID NO: 45 and SEQ ID NO: 84, are shown for primers #3 and #4, respectively, along with the corresponding mutated amino acid sequences (SEQ ID NOS: 46 and 48) in the region of the primers. SEQ ID NO: 47 is the nucleotide sequence complementary to primer #4.

FIG. 23 shows a nucleic acid (SEQ ID NO: 49) and amino acid sequences (SEQ ID NOS: 50 and 51) of L chain variable region of humanized C25 antibody (RC25). The nucleotide sequences, SEQ ID NOS: 54, 56, 85 and 86, are shown for overlapping primers #7, #8, #5, and #6, respectively, along with the corresponding mutated amino acid sequences (SEQ ID NOS: 53, 55 and 57) in the region of the overlapping primers. SEQ ID NO: 52 is the nucleotide sequence complementary to primer #5.

FIG. 24 shows antibody dependent complement-mediated cytotoxicity (ACC) of humanized C25 antibody (RC25) against HIV-infected cells in comparison with those of C25 antibody and normal human immunoglobulin.

Figure 25A:
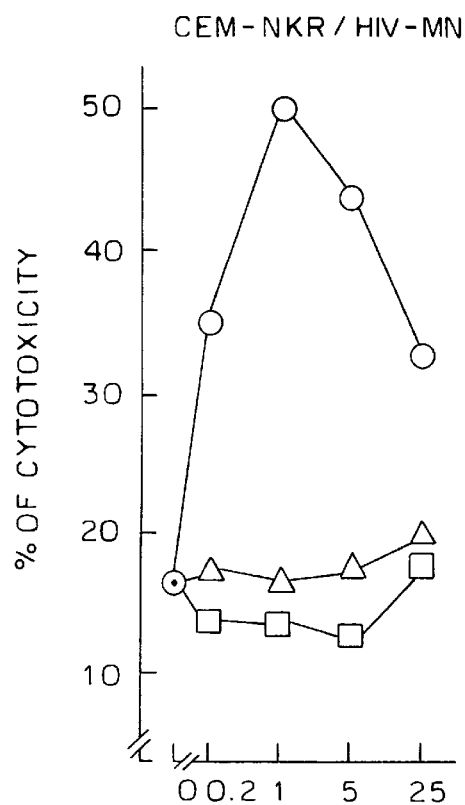
Figure 25B:
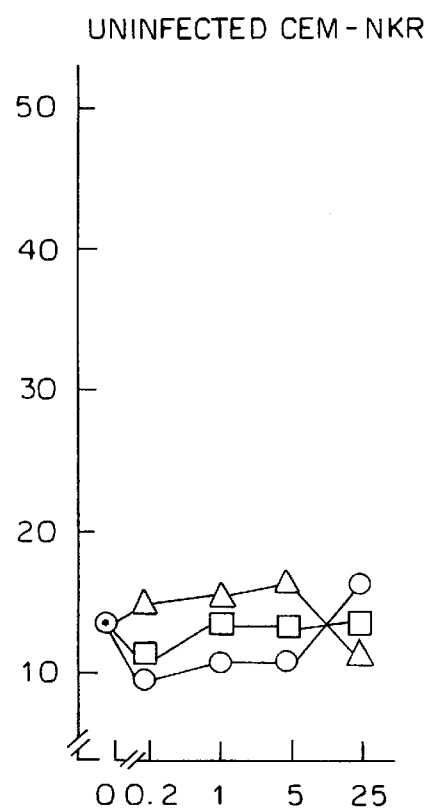

FIG. 25 shows antibody dependent cell-mediated cytotoxicity (ADCC) of humanized C25 antibody (RC25) against HIV-infected cells in comparison with those of C25 antibody and normal human immunoglobulin.

Figure 26:
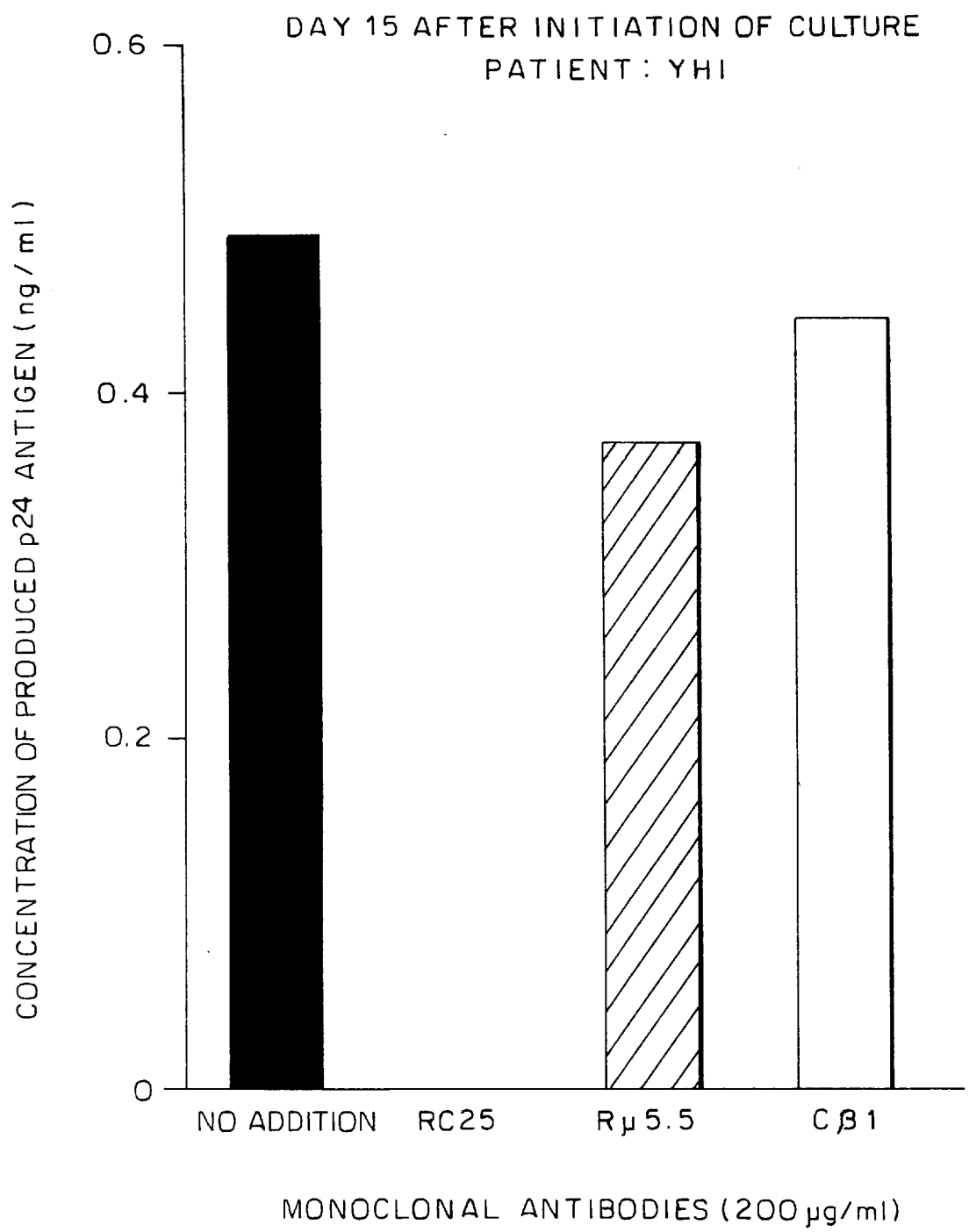

FIG. 26 shows a neutralizing activity of humanized C25 antibody (RC25) against virus derived from plasma obtained from HIV-infected patient (YHI).

Figure 27:
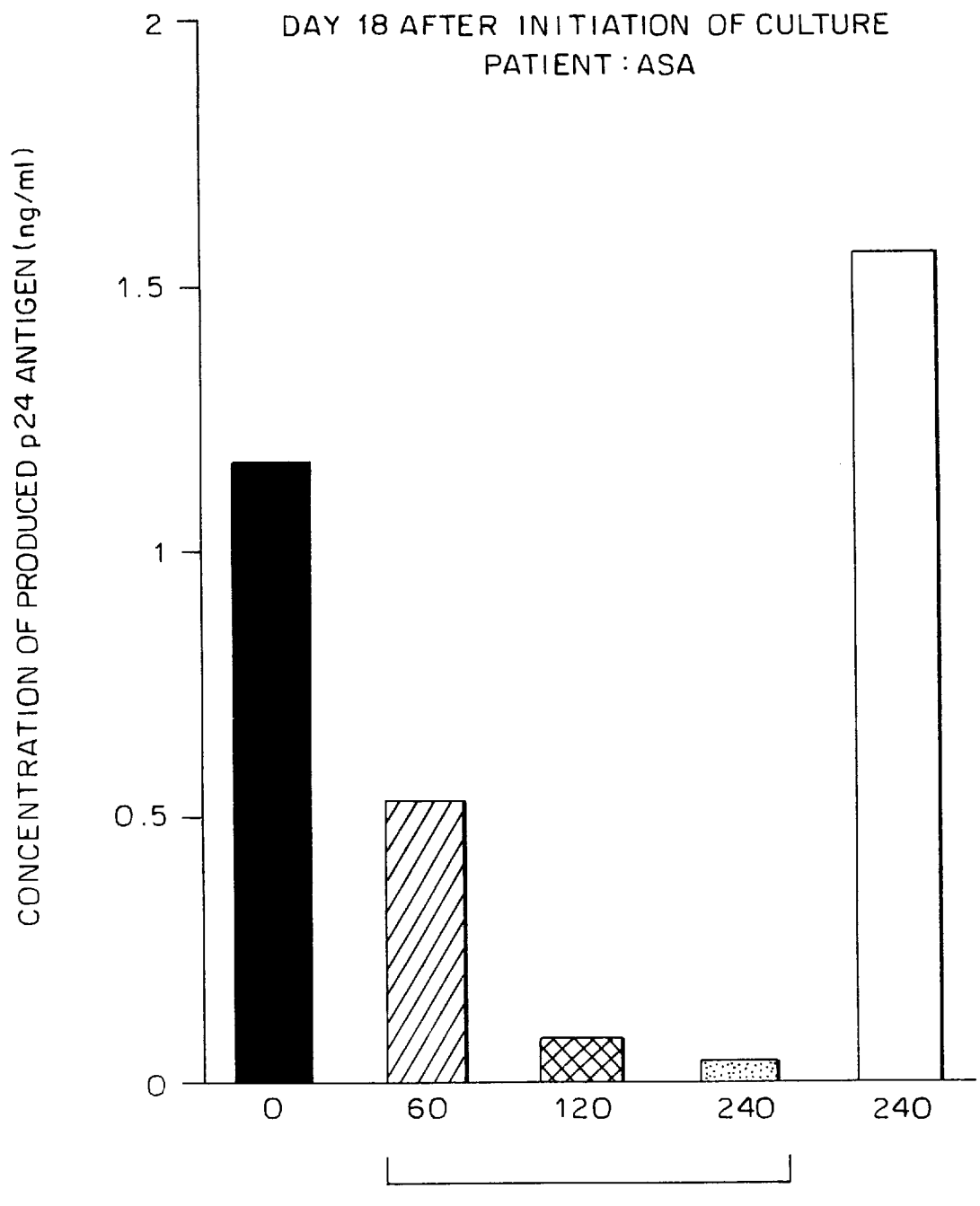

FIG. 27 shows a neutralizing activity of humanized C25 antibody (RC25) against virus derived from mononuclear cells in peripheral blood obtained from HIV-infected patient (ASA).

Figure 28:
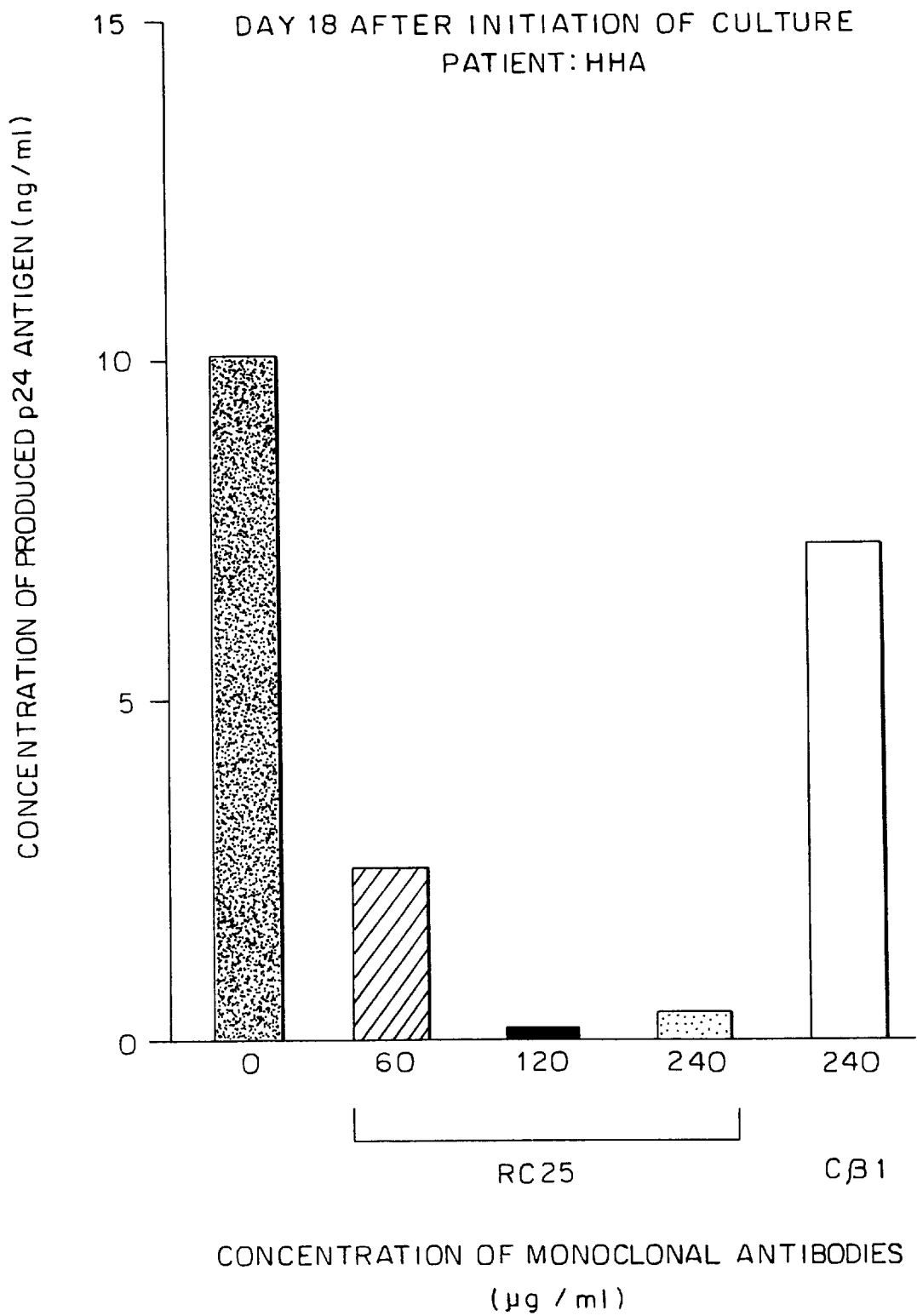

FIG. 28 shows a neutralizing activity of humanized C25 antibody (RC25) against virus derived from mononuclear cells in peripheral blood obtained from HIV-infected patient (HHA).

Figure 29:
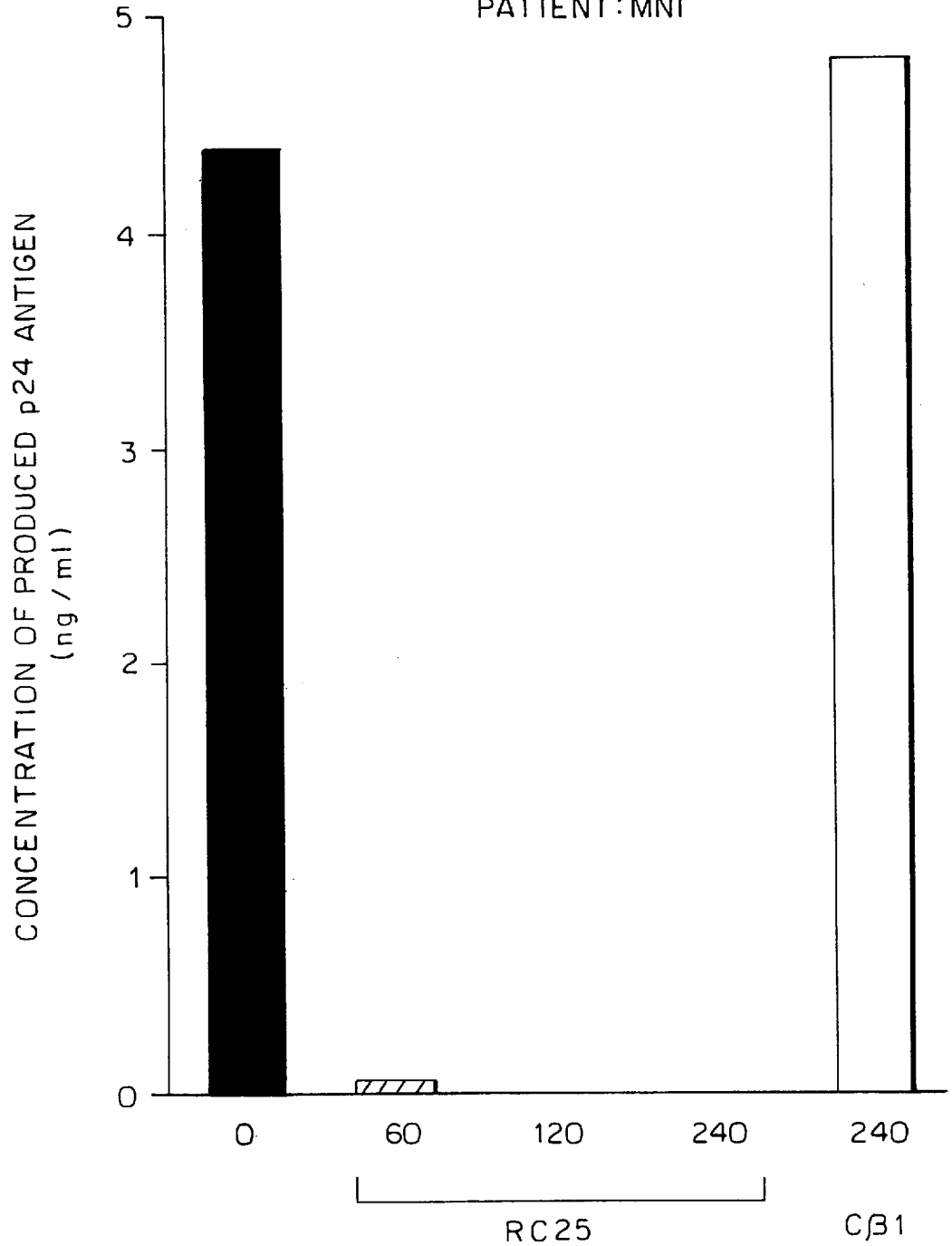

FIG. 29 shows a neutralizing activity of humanized C25 antibody (RC25) against virus derived from mononuclear cells in peripheral blood obtained from HIV-infected patient (MNI).

Figure 30:
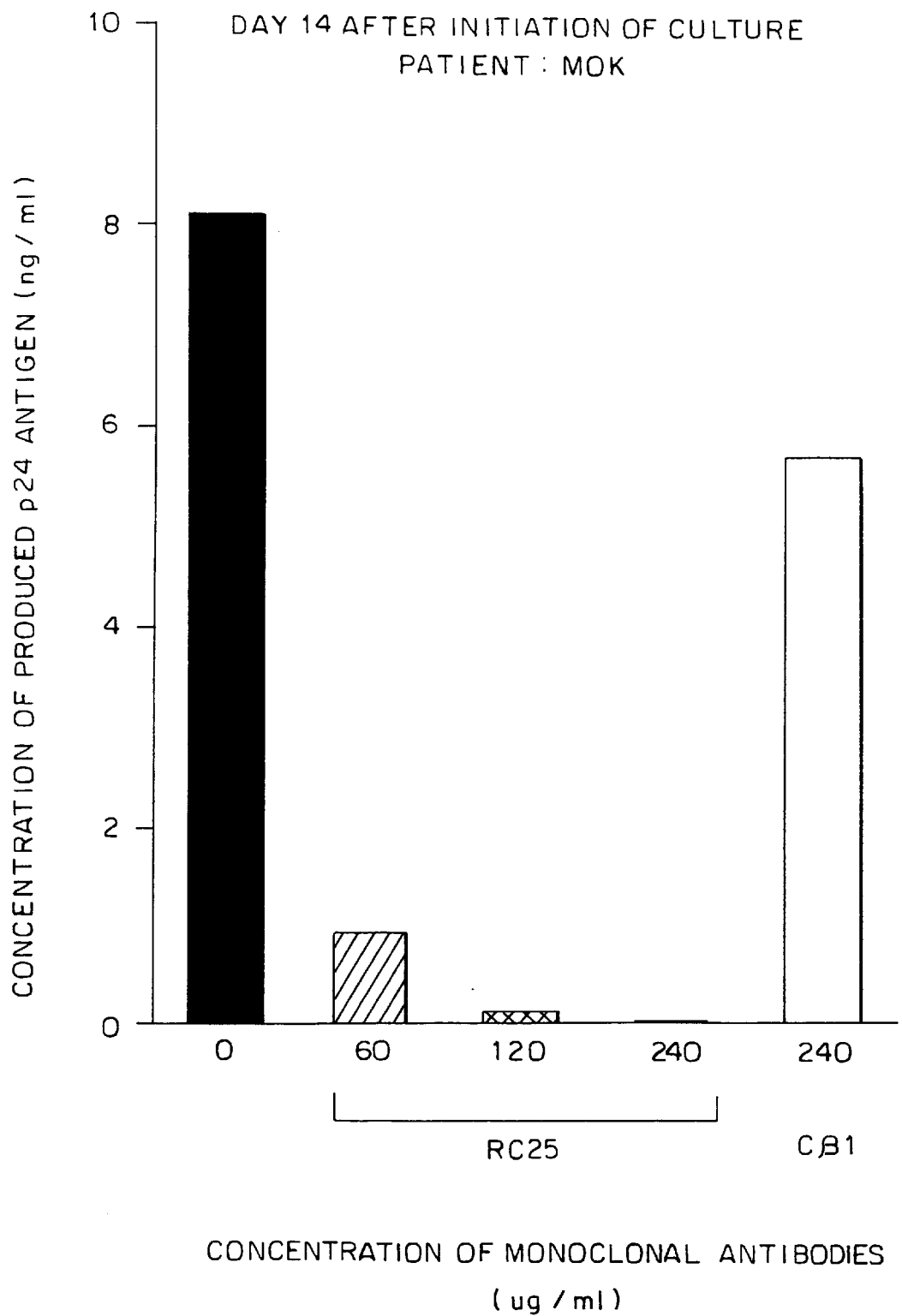

FIG. 30 shows a neutralizing activity of humanized C25 antibody (RC25) against virus derived from mononuclear cells in peripheral blood obtained from HIV-infected patient (MOK).

Figure 31:
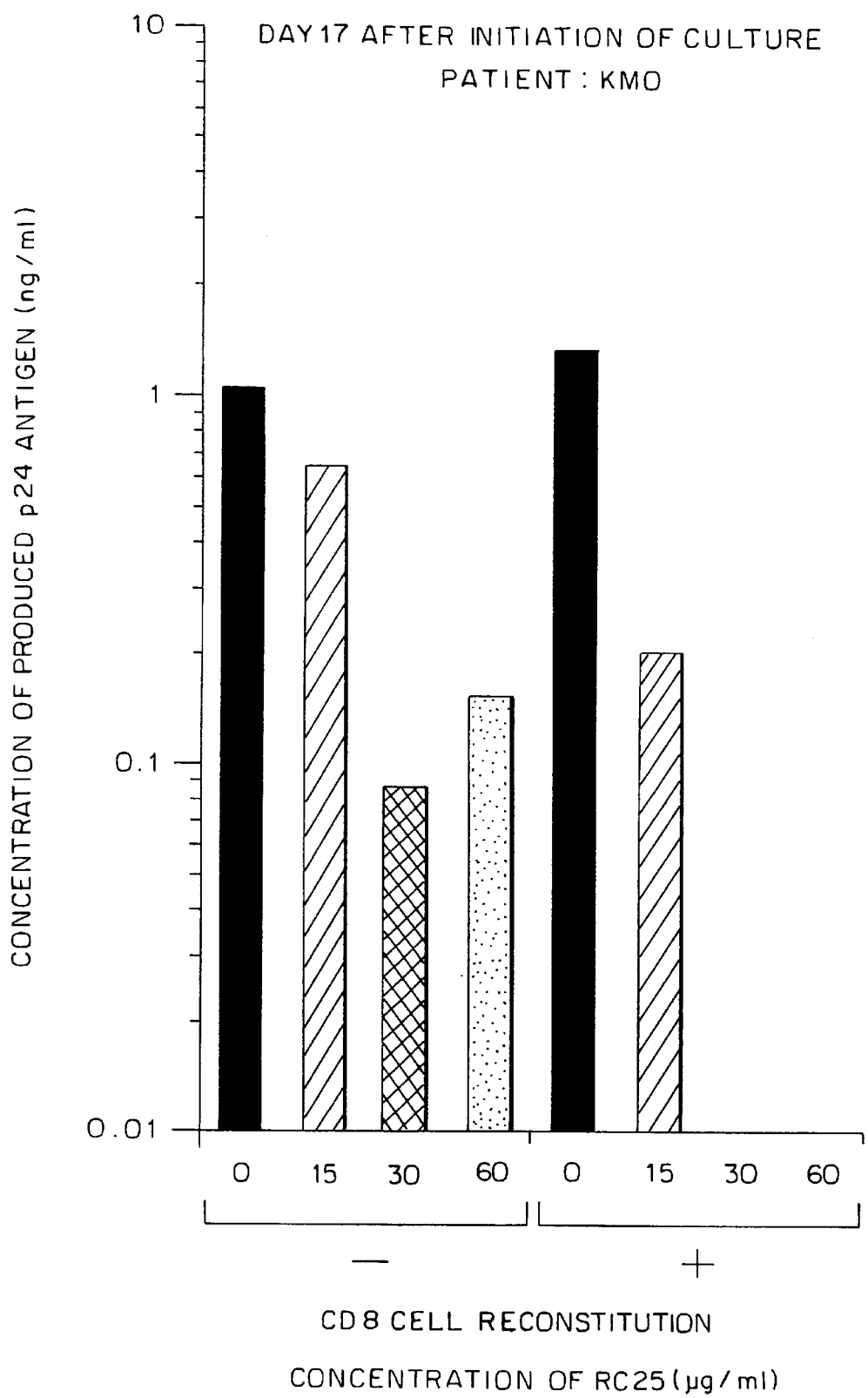

FIG. 31 shows decrease in an effective concentration of humanized C25 antibody (RC25) against virus derived from mononuclear cells in peripheral blood obtained from HIV-infected patient (KMO) after reconstitution of CD8.

BEST MODE FOR PRACTICING THE INVENTION

Figure 1:
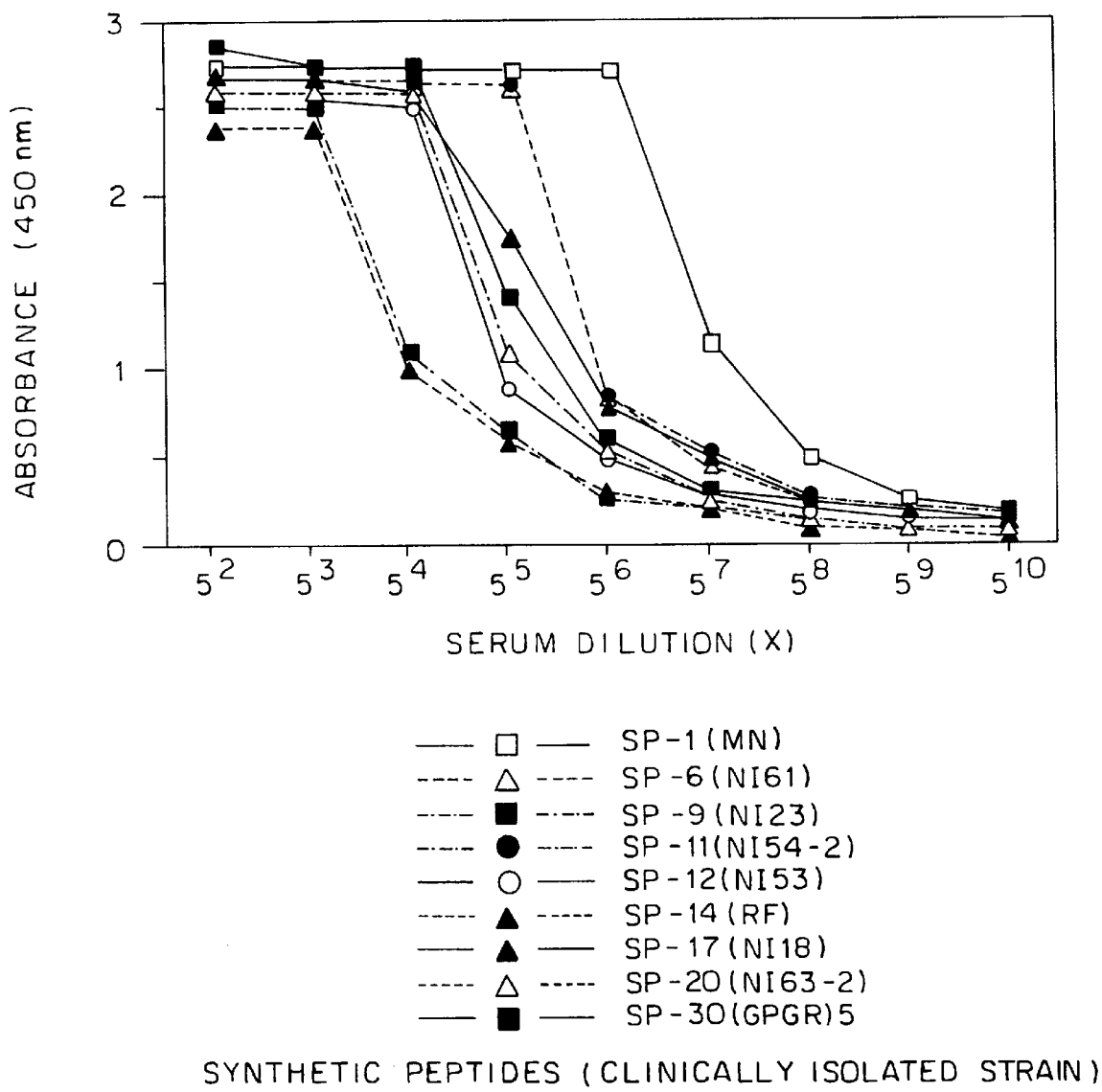

FIG. 1 shows a reactivity of a serum of mouse immunized in accordance with the above-mentioned procedure with various PND region peptides. That is, anti-serum obtained from mouse immunized sequentially with multiple PND peptides, each having GPGR sequence in common but a different remaining amino acid sequence, reacted all the PND peptides used for immunization. More surprisingly, said anti-serum reacted not only with the peptides used for immunization but also with other PND peptides comprising GPGR sequence in common. It also reacted strongly with the peptide (SP-30) comprising 5 repeats of the amino acid sequence GPGR which is common in the immunogenic PND peptides. It was further confirmed that this anti-serum could neutralize many HIV strains.

Figure 2:
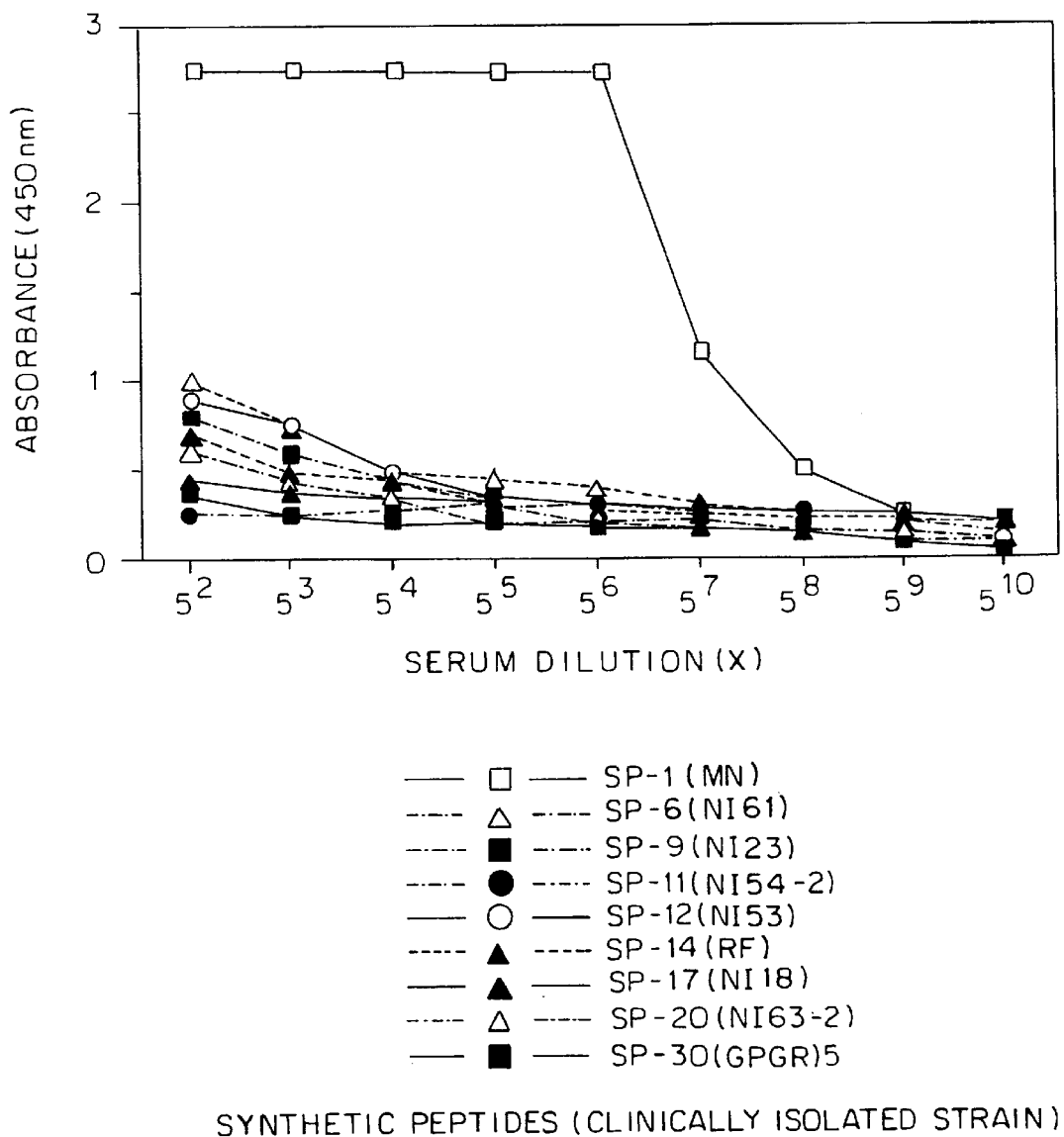
Figure 4:
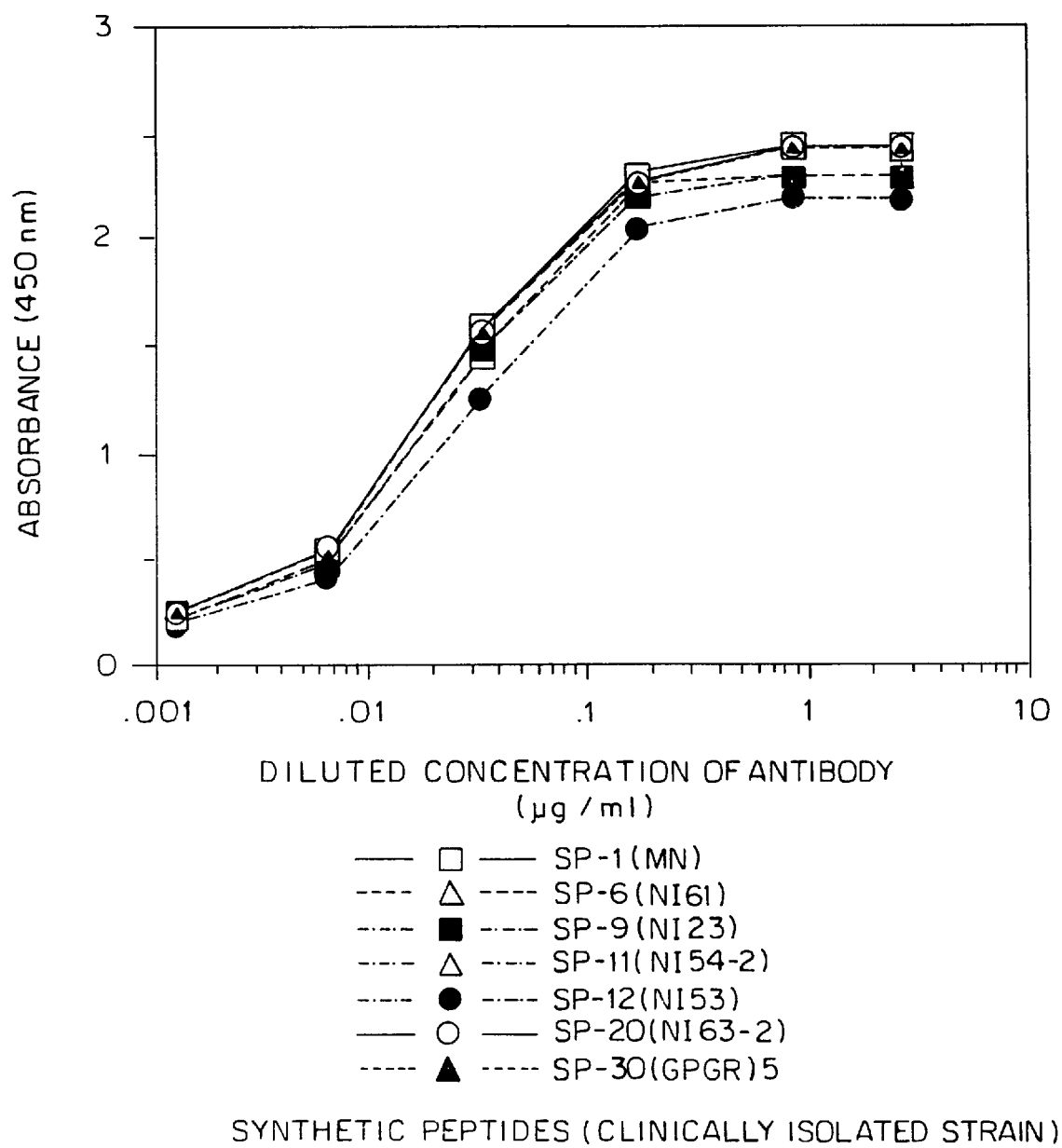
Figure 5:
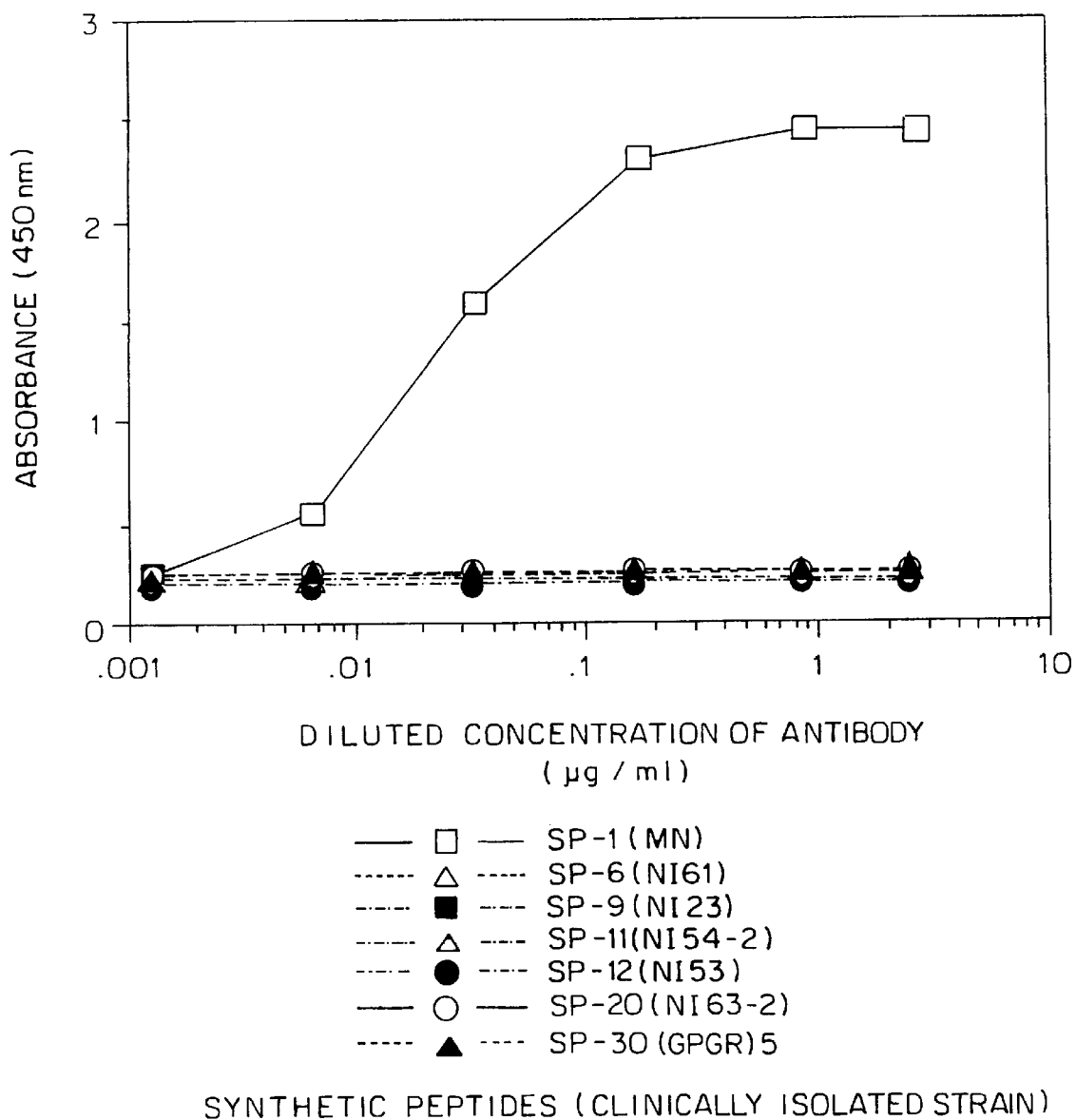

On the contrary, as shown in FIG. 2, anti-serum obtained from mouse immunized 5 to 6 times with a single peptide (SP-1) reacted with the immunogenic PND peptide but showed a low reactivity with other PND peptides. A reactivity with the synthetic GPGR peptide was also studied but it hardly reacted. That is, such mouse immunized with a single peptide showed merely a response of a strain-specific antibody even with hyperimmunization.

This reveals that such mouse immunized sequentially with several different PND peptides of HIV induced anti-PND-Tip antibody having a broad neutralizing spectrum against various HIV strains. Therefore, it was expected that cell fusion with spleen cells from this mouse could efficiently prepare cells which produce monoclonal antibody having a broad neutralization spectrum.

A hybridoma is prepared in accordance with the procedures by Kohler and Milstein (Nature 256, p.495 (1975)). A myeloma cell preferably includes MOPC-21NS/1 (Nature 256, p.495 (1975)), SP2/0-Ag14 (Nature 276, p.269 (1979)), p3X 63Ag8-U1 (Eur. J. Immunol. 6, p.511 (1976)), p3X63-Ag8 (Nature, 256, p.495 (1975)), p3X63-Ag8.653 (J. Immunol. 123, p.1548 (1979)), etc. Spleen cells and myeloma cells are mixed together at a ratio of 1:1 to 10:1. Fusion is conducted in a phosphate buffer (pH 7.2 to 7.4) containing NaCl (about 0.85%) and polyethylene glycol having a molecular weight of 1,000 to 6,000. Fusion is conducted by incubating the mixture of both cells at 35 to 37° C. for 1 to 5 minutes. Selection of fused cells (hybridomas) is made by selecting growing cells using a basal medium containing hypoxanthine (1.3 to 1.4 mg/dl), aminopterin (18 to 20 μl/dl), thymidine (375 to 4,000 μl/dl), streptomycin (50 to 100 μg/ml), penicillin (50 to 100 Units/ml), glutamine (3.5 to 4.0 g/l) and fetal calf serum (10 to 20%). The basal medium includes those which are generally used for culture of animal cells, such as RPMI1640 medium, Eagle MEM medium, etc. Cloning of fused cells is conducted at least twice by a limiting dilution method.

Another important aspect to be considered in preparing a monoclonal antibody is what kind of antibodies produced by a hybridoma should be selected. That is, cell fusion provides many hybridomas, but among these, hybridomas producing a desired antibody must be cloned. Selection is usually made by using a reactivity with HIV strains employed in laboratories such as HIV-MN or a neutralizing epitope, PND peptide, derived therefrom, as an index. However, such strains are those subcultured in vitro, and hence, do not always reflect HIV strains actually occurring within the living body of patients. Since an object of the present invention is to drive away HIV strains which are present within the body of patients and actually epidemic, selection of a hybridoma producing a neutralizing antibody for this purpose is preferably conducted by using HIV strains derived from infected patients. Therefore, a gene coding for an amino acid sequence of PND region is directly isolated from HIV-infected individuals and expressed in *E. coli*. Using the reactivity with this recombinant PND peptide as an index, selection of a desired hybridoma is conducted to select a hybridoma producing a monoclonal antibody which binds to HIV present within the body of patients. Furthermore, in order to establish an antibody having a broad neutralization spectrum, recombinant PND peptides are prepared from as many HIV-infected individuals as possible, and an antibody capable of reacting with most of these peptides is selected.

Employing the above-mentioned method, the present inventors have established a monoclonal antibody C25 which broadly neutralizes various HIV variants. C25 antibody strongly inhibited infection by cell-free viruses and cell-to-cell infection in vitro. C25 antibody reacted with most of peptides used as an immunogen and neutralized additional many HIV strains, suggesting that an epitope recognized by this antibody is a region conserved among strains, i.e. GPGR and surroundings thereof.

As a result of detailed analysis of epitopes using synthetic peptides, C25 antibody of the present invention was found to react with a series of peptides comprising the following amino acid sequence at around PND-Tip in PND region:

Xa1-Gly-Pro-Xa2-Arg-Xa3 (SEQ ID NO: 58)
  wherein Xa1 is Ala, Ile, Leu, Met, Asn, Pro, Gln, Ser, Thr, Val or Tyr
  Xa2 is Gly or Ala
  Xa3 is Ala, Cys, Asp, Glu, Gly, His, Ile, Lys, Leu, Met, Asn, Gln, Arg, Ser, Thr, Val, Trp or Tyr.

Furthermore, C25 antibody of the present invention was found to react with the peptides:

Xaa-Gly-Pro-Gly-Arg-Ala (SEQ ID NO: 59)
  wherein Xaa is Ala, Ile Leu, Met, Asn, Pro, Gln, Ser, Thr, Val, Tyr;

Ile-Gly-Pro-Gly-Arg-Xaa (SEQ ID NO: 60)
  wherein Xaa is Ala, Cys, Asp, Glu, Gly, His, Ile Lys, Leu, Met, Asn, Gln, Arg, Ser, Thr, Val, Trp, Tyr;

Val-Gly-Pro-Gly-Arg-Thr (SEQ ID NO: 61);
Val-Gly-Pro-Gly-Arg-Ser (SEQ ID NO: 62); or
Ile-Gly-Pro-Ala-Arg-Ala (SEQ ID NO: 63).

That is, C25 antibody of the present invention recognized an epitope formed by six amino acids comprising GPGR as a core and each one amino acid adjacent thereto at the N and C termini.

Based on the above observation, it was confirmed that C25 antibody has a broad neutralization spectrum since it recognized a highly conserved amino acid sequence within PND region of HIV and inhibited many HIV infections.

Then, the present inventors have examined usefulness of C25 antibody in actual clinical usage by studying a neutralization spectrum of C25 antibody against HIVs derived from actual HIV-infected individuals.

Clinical usefulness means, first of all, what range of actually epidemic HIV variants C25 antibody can bind to and neutralize. In this respect, PND region of HIV variants present within the living body of each infected individual is first studied to determine an amino acid sequence of HIV having the highest frequency as a consensus sequence, and a reactivity between PND peptides having said sequence and C25 antibody was studied. As a result, C25 antibody reacted with about 80% of the consensus peptides of HIV variants derived from each patient. Viewing that the strain-specific neutralizing monoclonal antibody $\mu$5.5 previously established by the present inventors showed a binding rate of 30%, C25 antibody was found to have a quite broad neutralization spectrum.

Second aspect of clinical usefulness is to what range of variants it is effective among quasispecies of HIV variants occurring in a single patient. When an amino acid sequence of viral variants occurring in a respective HIV-infected individual is determined, they do not have a completely identical amino acid sequence, but quasispecies of viral variants having a little bit diverse amino acid sequence infect a patient. Accordingly, for driving away all the infected viruses from the living body by administering an antibody as a medicament, the antibody must react with most of HIV variants occurring in a patient. In this respect, a reactivity between C25 antibody and PND region peptides isolated from a single patient was determined. When the strain-specific antibody $\mu$5.5 was used, there remained in the living body several HIV variants which did not reacted with the antibody. On the contrary, C25 antibody could react all or most of HIV variants occurring in an infected individual.

As mentioned above, it was revealed that C25 antibody of the present invention is a monoclonal antibody which recognizes a highly conserved PND-Tip region of PND region and shows a strong neutralizing activity, and hence, can sufficiently cope with the diversity of HIV. In fact, C25 antibody reacted with a majority of HIV variants occurring in the living body of infected individuals, and hence, has much clinical usefulness, suggesting clinical applicability of said antibody.

A representative hybridoma producing the monoclonal antibody C25 of the present invention has been deposited at National Institute of Bioscience and Human-Technology, Agency of Industrial Science and Technology 1-3, Higashi 1-chome, Tsukuba-shi, Ibaraki-ken, 305, Japan, with the accession number of FERM BP-4561 in accordance with the Budapest Treaty on Feb. 10, 1994.

Although C25 antibody of the present invention has a broad neutralization spectrum and is suggested to be clinically useful as mentioned above, since it is a mouse-derived antibody, its administration to humans is actually impossible in view of safety (induction of antigenicity) or effectiveness (shortening of a half-life). Therefore, it is necessary to modify C25 antibody to a molecule having an amino acid sequence of a human antibody without altering an antigen-binding capacity by using a genetic engineering technique.

In order to prepare a so-called chimeric or humanized antibody wherein the antigen-binding site of C25 antibody is linked to a human antibody constant region, a variable (V) region gene of C25 antibody was firstly cloned and a base sequence and an amino acid sequence coded thereby were determined.

A V region gene can be isolated by a usual gene manipulation technique. For example, it can be isolated by cloning a V region gene from a chromosomal DNA of a cell in accordance with the conventional method (for example, see T. Maniatis, "Molecular Cloning" Cold Spring Harbor Lab.

(1982)) or by synthesizing cDNA from mRNA materials of a cell in accordance with the conventional method (for example, D. M. Glover ed. "DNA cloning Vol. I" IRL press (1985)) and cloning a V region gene. In either procedures, as a probe for cloning a V region gene, DNA probes synthesized with reference to the nucleic acid base sequence of a mouse immunoglobulin gene which has already been reported (for example, Sakano et al., Nature, 286, p.676 (1980); E. E. Max et al., J.Biol.Chem., 256, p5116, (1981)) can be utilized. A cloning using PCR (polymerase chain reaction) can also be conducted (R. Orlandi et al., Proc. Natl. Acad. Sci. USA, 86, 3833 (1989); W. D. Huse et al., Science, 246, 1275 (1989)).

Using the above procedures, a variable region gene of C25 antibody was isolated and the base and amino acid sequences were analyzed, and as a result, it was found that the variable region of C25 antibody has a quite novel sequence different from those of antibodies which hitherto have been reported. CDR1 to CDR3 regions in FIGS. 19 and 20 are regions which actually bind to an antigen, and a sequence thereof is assumed to be closely related to a broad neutralization spectrum of C25 antibody.

In this respect, there were prepared a chimeric antibody gene by linking a gene fragment coding for an amino acid sequence of the regions to the upstream of a gene fragment of a human antibody constant region, or a humanized C25 antibody gene by transplanting the above-mentioned CDR regions alone at CDRs of a human antibody variable region. These genes were expressed and expression products were analyzed for their properties, and as a result, it was found that the chimeric and humanized C25 antibodies had a neutralization spectrum equivalent to that of mouse C25 antibody. Among other things, the fact that the humanized C25 antibody, wherein CDR regions alone were transplanted, reacted with PND means that, among V region of an antibody, CDRs are just the most important amino acid for binding. In addition, said antibody reacted only with an anti-human IgG but not with anti-mouse IgG, revealing that said antibody shows an antigenicity as a human antibody. Accordingly, it was suggested that, when administered to humans, the chimeric and humanized C25 antibodies do not provoke a severe antigenicity.

Another advantage of the chimeric and humanized antibodies is that they have an effector activity due to a constant region of a human antibody such as an antibody dependent complement-mediated cytotoxicity (ACC) and an antibody dependent cell-mediated cytotoxicity (ADCC). As mentioned hereinabove, C25 antibody inhibits infection by cell-free HIV viruses or cell-to-cell infection. However, in addition to this, whether it can destroy infected cells is another important factor for a medicament. Generally, an antibody alone cannot kill and destroy infected cells but can destroy infected cells via complement or effector cells having FcR. It is a constant region where an antibody binds to the complement or FcR (Mol.Immunol, 22, p161 (1985)).

In this respect, ACC and ADCC activities of the chimeric and humanized C25 antibodies of the present invention based on the antibody constant region were examined. As a result, the chimeric and humanized C25 antibodies significantly destroyed cells with continuous HIV infection in the presence of complement or effector cells. This suggests that the chimeric or humanized C25 antibody of the present invention can not only inhibit infection by free viral particles or a viral antigen on the surface of infected cells but also destroy infected cells.

As mentioned hereinabove, HIV variants actually occurred in HIV-infected patients do not have a completely identical amino acid sequence but they are quasispecies of many variants having different amino acid sequence. Accordingly, for driving away infected viruses from the living body by administering an antibody for treating purpose, the antibody should neutralize most of the quasispecies of variants. In this respect, said humanized C25 antibody was tested for a neutralizing activity against viruses derived from plasma and peripheral blood mononuclear cells from patients and as a result, apparently showed a neutralizing activity against many viruses derived from the patient. This revealed that said humanized C25 antibody is clinically useful against actual patients.

As mentioned above, the present inventors have prepared the monoclonal antibody C25 which is capable of neutralizing broadly many kinds of HIV strains from infected individuals. Furthermore, humanization of said antibody could decrease an antigenicity in humans and confer an effector activity such as destruction of infected cells. Thus, the present invention provides an antibody useful for prevention, treatment and diagnosis of HIV infection.

EXAMPLE 1

Preparation of Monoclonal Antibody 1-1) Preparation of Antigen (synthetic PND peptide)

Synthetic PND peptides corresponding to the amino acid Nos. 303–322 of gp120 as shown in Table 1 were used as an antigen for immunization and an antigen for assay.

TABLE 1

| Synthetic PND peptides | Isolated HIV strains | Amino acid sequence | SEQ ID NO: |
|---|---|---|---|
| SP-1  | MN     | YNKRKRIHIGPGRAFYTTKN-C | residues 6-25 of SEQ ID NO:1 |
| SP-6  | NI16-1 | NNTRKGIRIGPGRAVYATGK-C | SEQ ID NO:64 |
| SP-9  | NI23   | NNTRKSIPIGPGRAFYTTGE-C | residues 6-25 of SEQ ID NO:10 |
| SP-10 | NI63-1 | NNTRKRVTMGPGRVYYTTGE-C | SEQ ID NO:65 |
| SP-11 | NI54-2 | NNTRKGIRVGPGRAIYATEK-C | residues 6-25 of SEQ ID NO:5 |
| SP-12 | NI53   | NNTKKAIRVGPGRTLYATRR-C | residues 6-25 of SEQ ID NO:9 |
| SP-14 | RF     | NNTRKSITKGPGRVIYATGO-C | SEQ ID NO:66 |
| SP-17 | NI18   | NNTRKRITTGPGRVYYTTGE-C | SEQ ID NO:67 |
| SP-20 | NI63-2 | NNTRRGIRIGPGRAFYATDK-C | residues 6-25 of SEQ ID NO:8 |
| SP-30 | —      | GPGRGPGRGPGRGPGRGPGR-C | SEQ ID NO:68 |

For chemical synthesis of the above peptides, ABI430A peptide synthesizer (Applied Biosystem) was used. As a result, a crude product was obtained. The peptide was removed from the resin by the TFMSA method and then purified by a reverse high performance liquid chromatography (HPLC). Purification by a reverse HPLC was repeated three times and the obtained fractions were collected.

Then, each of the obtained synthetic peptides was lyophilized and bound with KLH to prepare a peptide-KLH conjugate. First, each of the above peptide (10 mg) was dissolved in 10 mM PBS (pH 7.0; 2 ml) and thereto was added a solution of dimethylformamide (MBS type crosslinking agent) (40 mg/100 μl) and the mixture was stirred at room temperature for 30 minutes. The reaction solution was then washed three times with dichloromethane (2 ml) and the obtained aqueous layer was separated (Solution A). Separately, KLH (20 mg) was dissolved in 0.2 M Tris-HCl (pH 8.6, 8M urea) (5 ml) and thereto was added dithiothreitol (DTT) and the mixture was stirred at room temperature for 1 hour. To the reaction solution was added 10% trichloroacetic acid (3 ml). The precipitate was filtered by suction, washed with distilled water (2 ml), and then dissolved in 20 mM NaPB (pH 7.0 6M urea) (5 ml) (Solution B). Solutions A and B were mixed together and the mixture was stirred at room temperature for 3 hours. The reaction product was dialyzed and then lyophilized.

As mentioned above, PND peptide and PND peptide-KLH conjugate were prepared and used as an antigen for immunization and an antigen for assay.

1-2) Immunization of Mouse

By way of example, immunization with the synthetic peptides prepared as mentioned above is shown hereinbelow but an order of the peptides for immunization can be varied.

BALB/c and C3H/HeN mice of 4 to 8 weeks old were used. Immunization was conducted by five intraperitoneal inoculations and a following one intravenous inoculation. That is, there were made intraperitoneal (i.p.) administration of SP-1-KLH in the presence of Freund's complete adjuvant on Day 0; i.p. administration of SP-17-KHL in the presence of Freund's incomplete adjuvant on Day 7; i.p. administration of SP-11-KHL in the presence of Freund's incomplete adjuvant on Day 14; i.p. administration of SP-12-KHL in the presence of Freund's incomplete adjuvant on Day 21; i.p. administration of SP-14-KHL in the presence of Freund's incomplete adjuvant on Day 28; and intravenous administration of SP-30-KLH in the absence of adjuvant on Day 35.

1-3) Measurement of Antibody Titer in Anti-serum of Immunized Mice

This was conducted by EIA method. The synthetic peptide antigen (2 μg/ml) prepared as mentioned above was added to a 96-well microtiter plate at 100 μl/well and the plate was incubated at 4° C. overnight to immobilize the antigen. Thereto was further added 1% BSA (bovine serum albumin) solution (150 μl) and the plate was incubated in the same way for masking. To the thus prepared antigen-immobilized plate were added hybridomas obtained by a cell fusion method or a culture supernatant of hybridomas after cloning. After incubating the plate at 4° C. for 1.5 hours, it is washed three times with 0.1% Tween20/PBS and then a solution of peroxidase-labelled anti-mouse immunoglobulin antibody (manufactured by Kappel; 5,000 times dilution) was added thereto at 100 μl/well. After incubating the plate at 4° C. for 1 hour, it was washed five times with 0.1% Tween20/PBS. Then, a solution of TMBZ substrate was added to develop a color reaction by the conventional procedure and an absorbance at a wave length 450 nm was measured.

As is clear from FIG. 1, the anti-serum obtained after final immunization reacted all the peptides SP-1, SP-17, SP-11, SP-12, SP-14 and SP-30. Surprisingly, the anti-serum reacted not only with the peptides used for immunization but also with PND peptides SP-6, SP-9 and SP-20, derived from other HIV strains. In contrast, when a mouse is immunized with a single peptide SP-1 five to six times, the obtained anti-serum was highly reactive with the immunogenic peptide (SP-1) but showed a lower reactivity with other peptides (FIG. 2). As to the reactivity with SP-30, the anti-serum of the mouse immunized with a single peptide hardly reacted with this peptide (FIG. 2) whereas the anti-serum of the mouse immunized with different PND peptides showed strong reactivity (FIG. 1). A neutralization test was also conducted for anti-sera, and as a result, it was found that the anti-serum of the mouse immunized with SP-1 alone could neutralize only HIV-MN strain whereas the anti-serum of the mouse immunized with many kinds of PND peptides could neutralize many HIV strains. This revealed that the immunized mouse induced an anti-GPGR antibody having a broad neutralization spectrum against various HIV strains. The anti-serum was also confirmed to neutralize various HIV strains. Therefore, a cell fusion was conducted using spleen cells of this mouse.

1-4) Cell Fusion and Culture of Hybridomas

Three days after the final immunization, spleen cells were collected from the mouse by the conventional procedure.

The spleen cells were mixed with myeloma cells p3X63Ag8-U1 at a ratio of cell number, 1:5, and the mixture was subjected to centrifugation (1,200 r.p.m. for 5 minutes) to remove supernatant. After loosening the precipitated cell lump sufficiently, a polyethylene glycol solution (polyethylene glycol-4000 (2 g), RPIM1640 (2 ml)) (1 ml) was added thereto while stirring. The mixture was incubated at 37° C. for 5 minutes, and then RPMI1640 was added slowly to the mixture to give a total volume of 50 ml. After centrifugation (900 r.p.m. for 5 minutes), the supernatant was removed and the cells were loosened mildly. Thereto was added a normal medium (RPMI-1640 medium supplemented with 10% fetal calf serum) (100 ml) and the cells were mildly suspended using a measuring pipet.

The suspension was poured into each well of a 24-well culture plate (at 1 ml/well), and culture was conducted in an incubator containing 5% carbonic acid gas at 37° C. for 24 hours. Then, 1 ml/well of an HAT medium (a normal medium supplemented with hypoxanthine (1.3 to 1.4 mg/dl), thymidine (345 to 4,000 μl/dl) and aminopterin (18 μl/dl)) was added to the plate and culture was further continued for 24 hours.

Thereafter, the culture supernatant (1 ml) was exchanged with the same volume of the HAT medium at an interval of 24 hours for 2 days and culture was conducted for 10 to 14 days in the same manner.

For each of wells where fused cells (about 300 cells) were observed to grow in the shape of colony, the culture supernatant (1 ml) was exchanged with the same volume of an HT medium (the above HAT medium devoid of aminopterin) and thereafter the same exchange was conducted at an interval of 24 hours for 2 days. After culture on the HT medium for 3 to 4 days, a portion of the culture supernatant was taken and a desired hybridoma was selected by the screening method as mentioned hereinbelow.

1-5) Screening of Hybridoma

Selection of a desired hybridoma was made by a combination of the following EIA method and the Western blotting method. The thus selected clone was measured for its neutralizing activity.

(1) EIA Method

To a 96-well microtest plate were added the synthetic PND peptide antigens prepared as mentioned above or PND peptides expressed in E. coli as described in Examples 2 (2-5) (protein concentration: 1 to 10 μg/ml) at 100 μl/well, and the plate was incubated at 4° C. overnight to immobilize the peptide. Thereto was further added 1% BSA (bovine serum albumin) solution (150 μl) and the plate was incubated in the same manner for masking. To the thus prepared antigen-immobilized plate were added the hybridomas or the culture supernatant of the hybridomas after cloning. After incubating the plate at 4° C. for 1.5 hours, the plate was washed three times with 0.1% Tween20/PBS and a solution of peroxidase-labelled anti-mouse immunoglobulin antibody (manufactured by Kappel; 5,000 times dilution) (100 μl/well) was added to the plate. After incubating the plate at 4° C. for 1 hour, the plate was washed five times with 0.1% Tween20/PBS. Then, a solution of TMBZ substrate was added to develop a color reaction by the conventional procedure and an absorbance at a wave length 450 nm was measured. Hybridomas which commonly react with a group of peptides whose GPGR sequence in PND region is conserved are selected and cloned. Hybridoma clones after cloning were also selected in the same manner.

(2) Western Blotting Method

This method was conducted in accordance with Towbin et al. (Proc.Natl.Acad.Sci.U.S.A., 76, p.4350 (1979)).

Figure 6A:
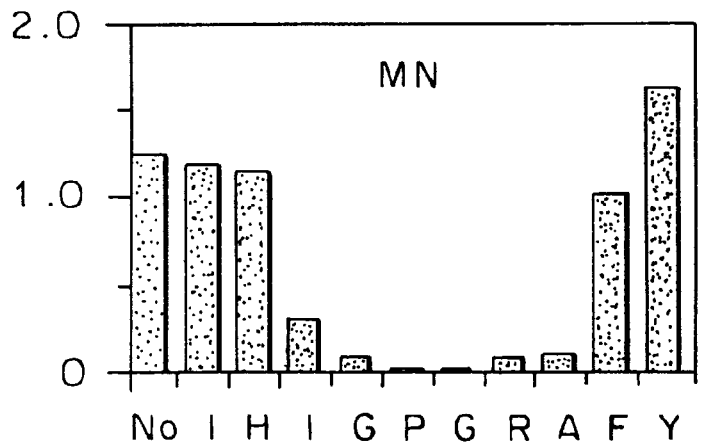
Figure 6B:
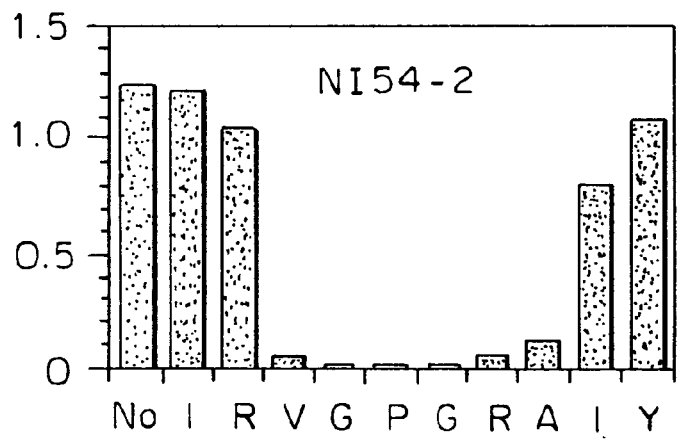
Figure 6C:
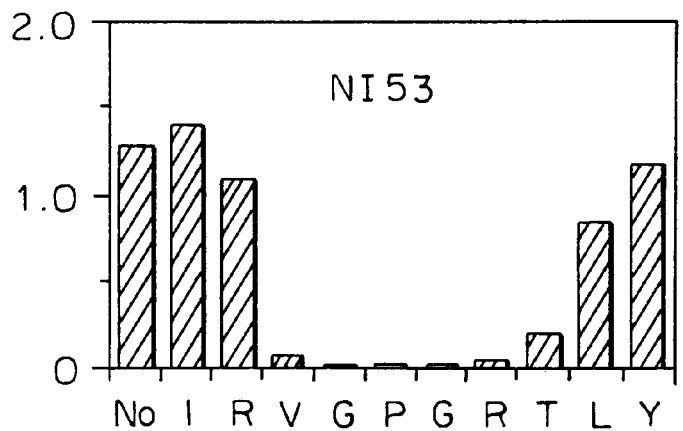

Viral particles of laboratory strains such as HIV-MN, HIV-LAV or HIV-RF or of clinically isolated strains such as NI61, NI23, NI54-2, NI53, NI18 or NI63, or PND peptides expressed in *E. coli* as described in Examples 2 (2-5), were prepared. The prepared viral particles or peptides were subjected to electrophoresis using 10% SDS-PAGE, the gel was transferred to a nitrocellulose membrane to transfer the viruses to said membrane, and the membrane was cut with 0.4 to 0.5 cm width. Each strip was immersed into the culture supernatant of the hybridomas and incubated overnight. Thereafter, the strips were washed three times with PBS and incubated in 1:750 dilution of a biotin-labelled anti-mouse IgG (manufactured by TAGO) for 2 hours. After washing the strips three times with PBS, they were immersed into an avidin coupled with horseradish peroxidase (manufactured by Sigma) (1:1000 dilution) and incubated for 1 hour. After washing the strips three times with PBS, a color reaction was developed with a coloring agent using 4-chloro-1-naphthol (manufactured by Bio-Rad) and the hybridomas were selected and cloned which commonly reacted with bands of the viral gp120 and the PND peptides expressed in *E. coli* whose GPGR sequence in PND region is conserved. Hybridoma clones after cloning were also selected in the same manner.

(3) Measurement of Neutralizing Activity

For measurement of a neutralizing activity, various laboratory viruses having respective PND amino acid sequence and various viruses isolated from patients and a culture supernatant of the viruses after cloning were used as a viral source ($10^{4.5}$ to $10^5$ $TCID_{50}$). Cloning of the viruses was made by a limiting dilution method, or a plaque method in CD4-HeLa cells.

First, the viral solution adjusted to 10 $TCID_{50}$/50 $\mu$l and a culture supernatant of the hybridoma clone or purified ascites (50 $\mu$l) (with various dilutions) were inoculated onto a 96-well flat bottom plate and the plate was incubated at 37° C. for 1 hour. Then, $10^4$ cells/100 $\mu$l/well of MT4 cells (suspended in RPMI1640 medium containing 10% FCS, L-glutamine 3.5 to 4.0 g/l, penicillin 50 U/ml and streptomycin 50 $\mu$l/ml) were added and cultured for 5 days.

A neutralizing activity was evaluated based on whether an antibody inhibits syncytium formation occurring upon infection or not. A neutralization titer was expressed as a minimum effective concentration of an antibody which inhibits the syncytium formation by 100%.

A hybridoma producing the monoclonal antibody C25 was obtained by the above-mentioned selection method.

1-6) Preparation of C25 Monoclonal Antibody

To pristan-treated SPF female mouse (BALB/c, C3H/HeN, and F1 mouse thereof) of 8 weeks old, $5\times10^6$ cells/mouse of the hybridoma C25 antibody strain obtained in the above 1-5 was administered intraperitoneally. After 10 to 21 days, ascitic cancer was induced. Ascites was taken out of mice and, after removing solid components by centrifugation at 3000 r.p.m. for 5 minutes, purified by affinity chromatography using Affigel Protein A MAPS-II kit (manufactured by Bio-Rad).

EXAMPLE 2

Analysis of Properties of C25 Monoclonal Antibody 2-1) Activity of C25 Antibody to Neutralize Virus A neutralizing activity of C25 antibody against HIV was analyzed using various HIV strains. FIG. 3 shows viral strains used and an amino acid sequence of PND region of the viruses. A neutralization test was conducted as shown in Example 1. As a control, monoclonal antibodies $\mu$5.5 which neutralizes HIV-MN strain in a strain-specific manner and $\alpha$64 which neutralizes NI53 strain in a strain-specific manner were used and compared with C25 antibody.

The left side of FIG. 3 shows a minimum effective concentration ($\mu$g/ml) of antibodies which inhibit infection of cell-free viruses by 100%. The neutralizing activity of C25 antibody is almost the same as those of $\mu$5.5 or $\alpha$64, and hence, is quite strong. As to specificity to HIV strains, C25 antibody neutralized much more HIV strains as compared to the strain-specific antibodies such as $\mu$5.5 or $\alpha$64, revealing a broad neutralization spectrum of C25 antibody.

The right side of FIG. 3 shows a minimum effective concentration of antibodies which inhibit a cell-to-cell infection of infected cells by more than 80%. An inhibitory activity of C25 antibody against cell-to-cell infection is also almost the same as those of $\mu$5.5 or $\alpha$64, and hence, is quite strong. C25 antibody inhibited cell-to-cell infection of much more HIV strains as compared to the strain-specific antibodies such as $\mu$5.5 or $\alpha$64, revealing a broad neutralization spectrum of C25 antibody.

2-2) Reactivity with Various Synthetic Peptides

The neutralization test revealed that C25 antibody had a broad neutralization spectrum. Then, how C25 antibody reacts with various PND peptides (comprising 20 amino acids) shown in Example 1 (1-1) was examined by EIA method.

As is clear from FIG. 4, C25 antibody reacted with SP-1, SP-6, SP-9, SP-11, SP-12, SP-20, and SP-30. This suggested that C25 antibody recognized PND-Tip region, a consensus sequence of the peptides. On the contrary, the strain-specific antibody $\mu$5.5 bound only with the antigen used for immunization, SP-1, but did not react with other peptides (FIG. 5).

2-3) Analysis of Epitope Recognized by C25 Antibody

Since it was suggested that the epitope recognized by C25 antibody is located in Tip sequence around GPGR in PND region, the recognized epitope was identified in accordance with following method.

(1) Binding Test with PND Peptides which is Devoid of a Specific Amino Acid

The above experiment 2-2 revealed that C25 antibody reacts with the peptides SP-1 (YNKRKRIHIGPGRAFYTTKN-C) (residues 6–25 of SEQ ID NO: 1) derived from HIV-MN strain, SP-12 (NNTKKAIRVGPGRTLYATRR-C) (residues 6–25 of SEQ ID NO: 9) derived from NI53, and SP-11 (NNTRKGIRVGPGRAIYATEK-C) (residues 6–25 of SEQ ID NO: 5) derived from NI54-2. By synthesizing peptides devoid of either one of amino acids of these peptides and examining the reactivity of the resulting peptides with C25 antibody, specific amino acids which contribute to the binding will be clarified. Accordingly, each ten nonapeptides which are devoid of either one of amino acids from the decapeptides, IHIGPGRAFY derived from MN strain and IRVGPGRTLY derived from NI53 strain, both decapeptides being known to bind to C25 antibody, were synthesized on a polyethylene rod and were tested for the reactivity with C25 antibody (FIG. 6).

In case of IHIGPGRAFY derived from HIV-MN strain, the peptides devoid of the 3rd to 8th amino acids, Ile, Gly, Pro, Gly, Arg and Ala hardly react with C25 antibody. In case of IRVGPGRTLY derived from NI53 strain, the peptides devoid of the 3rd to 8th amino acids, Val, Gly, Pro, Gly, Arg and Thr, do not react with C25 antibody. Furthermore, in case of IRVGPGRAIY derived from NI54-2 strain, the peptides devoid of the 3rd to 8th amino acids, Val, Gly, Pro, Gly, Arg and Ala, did not react with C25 antibody.

These results revealed that the sequence Ile-Gly-Pro-Gly-Arg-Ala (residues 14–19 of SEQ ID NO: 1) is indispensable for binding of C25 antibody with HIV-MN strain, the sequence Val-Gly-Pro-Gly-Arg-Thr (residues 14–19 of SEQ ID NO: 9) for binding with NI63 strain, and the sequence Val-Gly-Pro-Gly-Arg-Ala (residues 14–19 of SEQ ID NO: 5) for binding with NI54-2 strain, suggesting that six amino acids comprising a GPGR core and each one amino acid adjacent to both sides of said core is an epitope recognized by C25 antibody.

(2) Binding Test with Overlapped Hexapeptides

Figure 7:
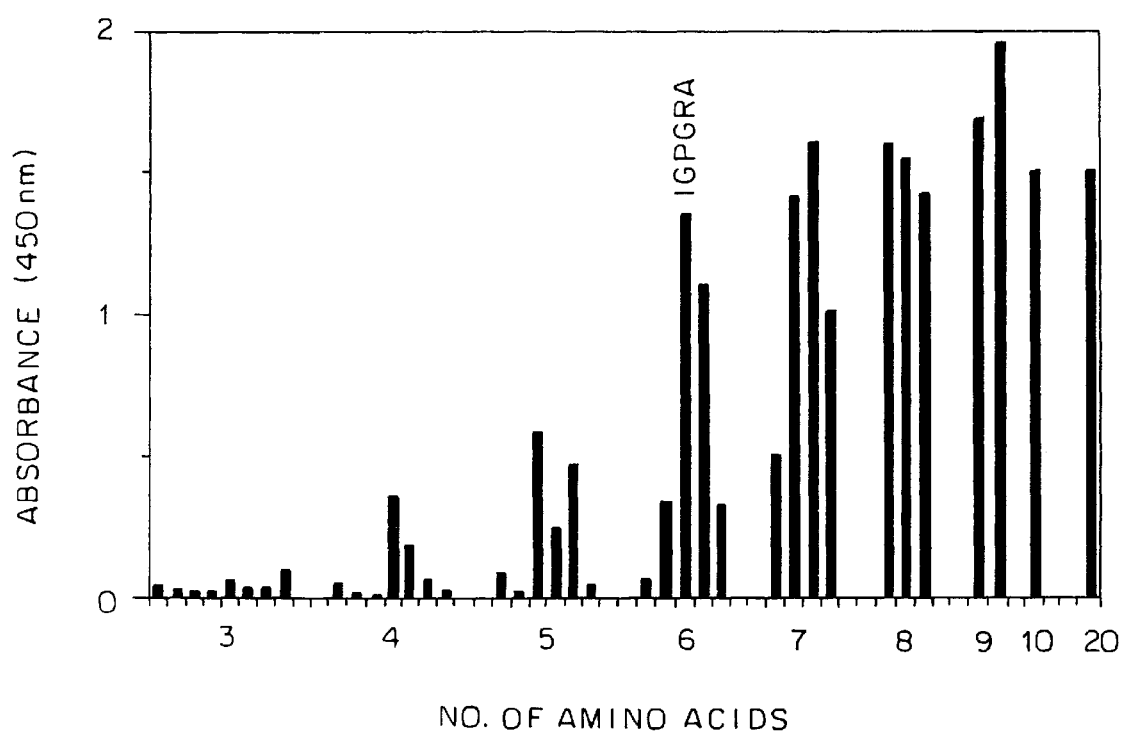
Figure 8:
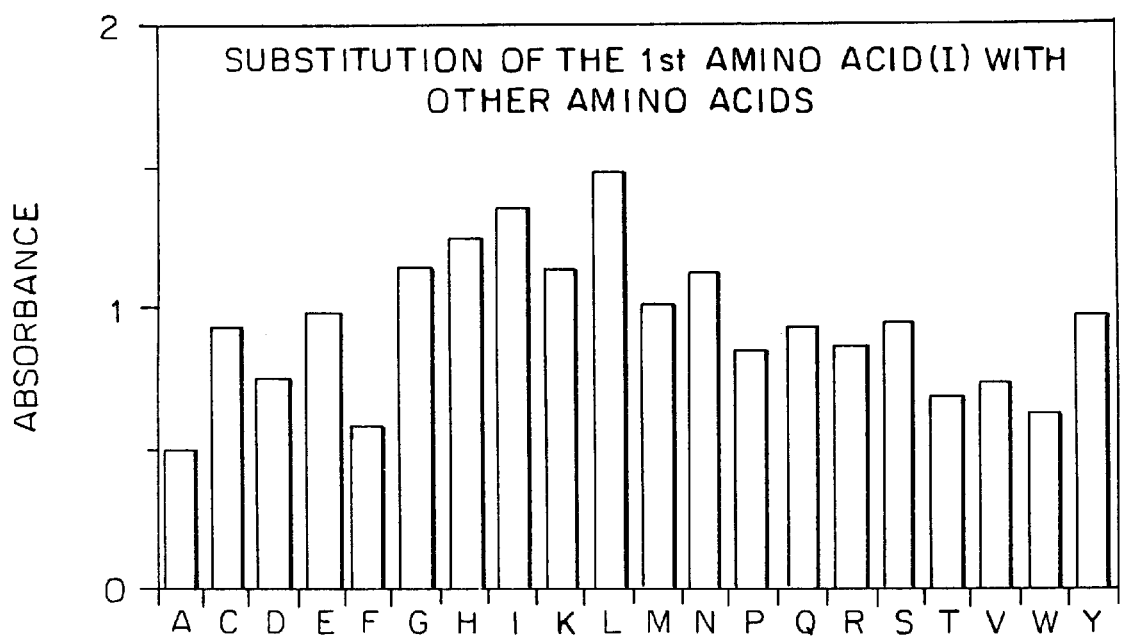
Figure 9:
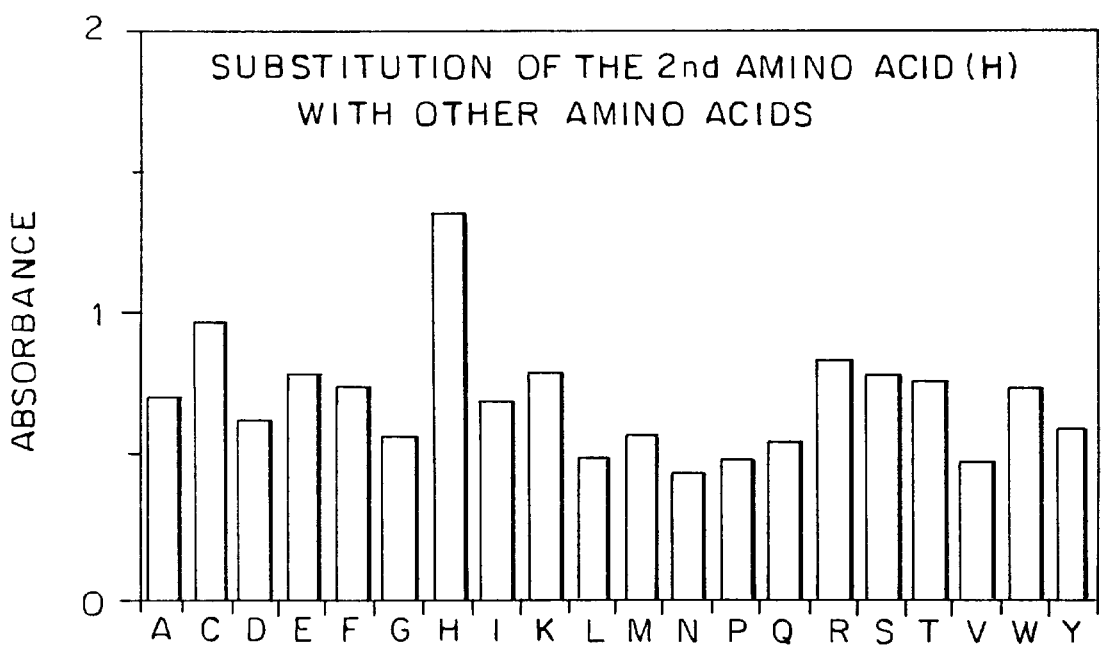
Figure 10:
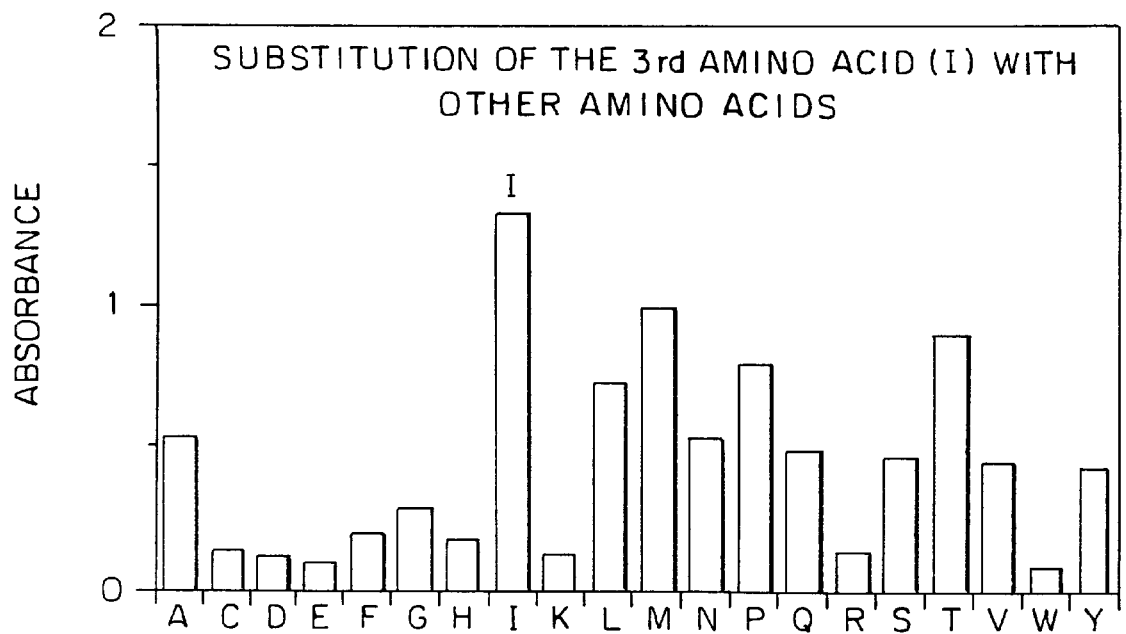
Figure 11:
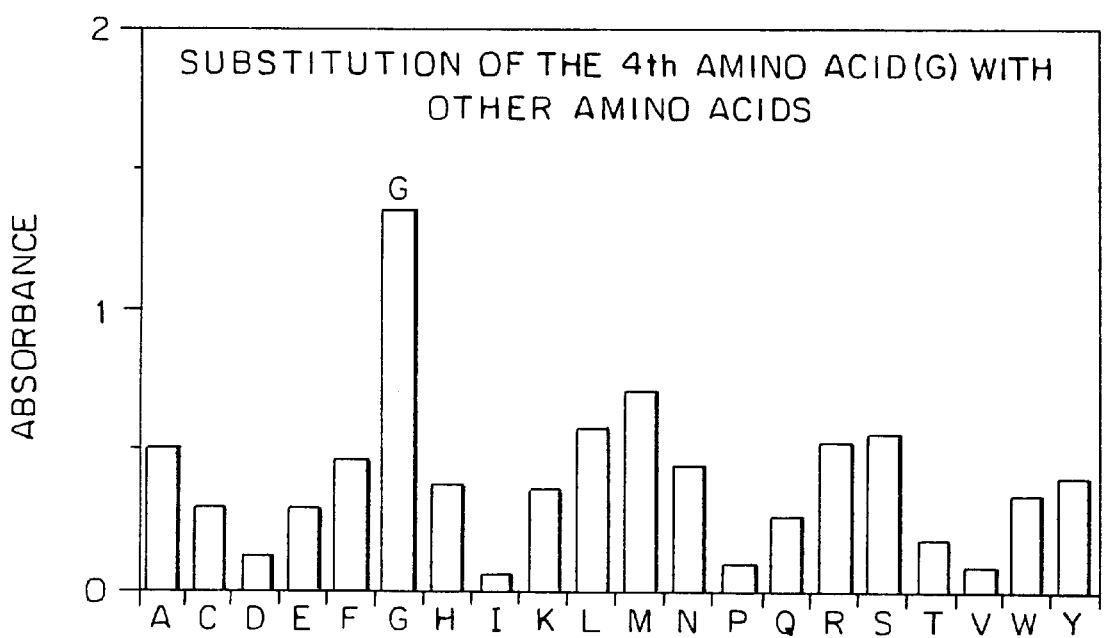
Figure 12:
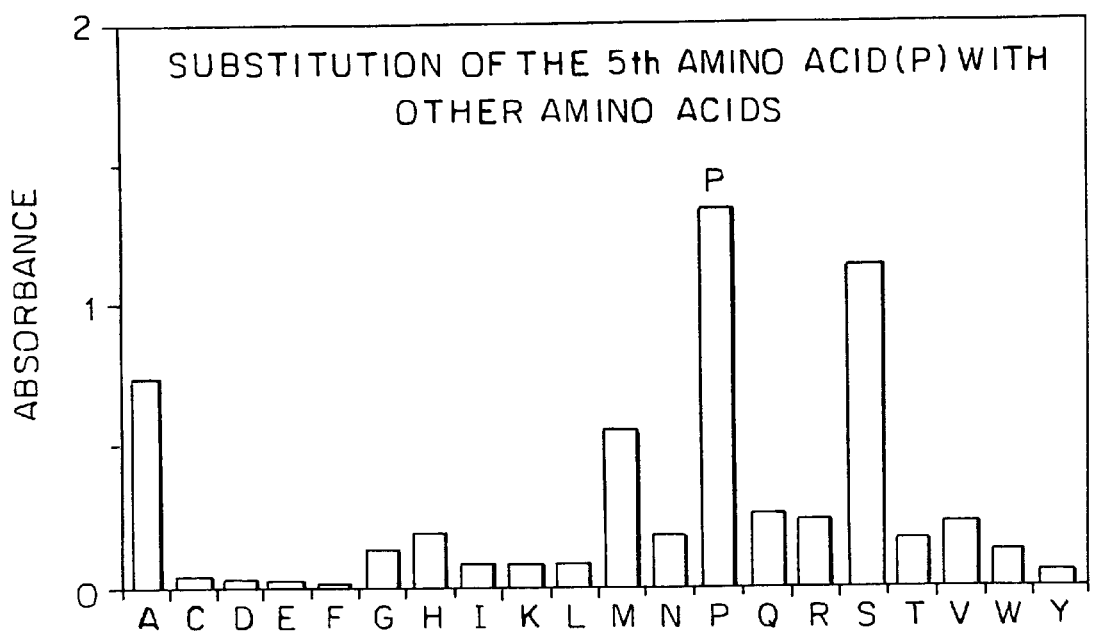
Figure 13:
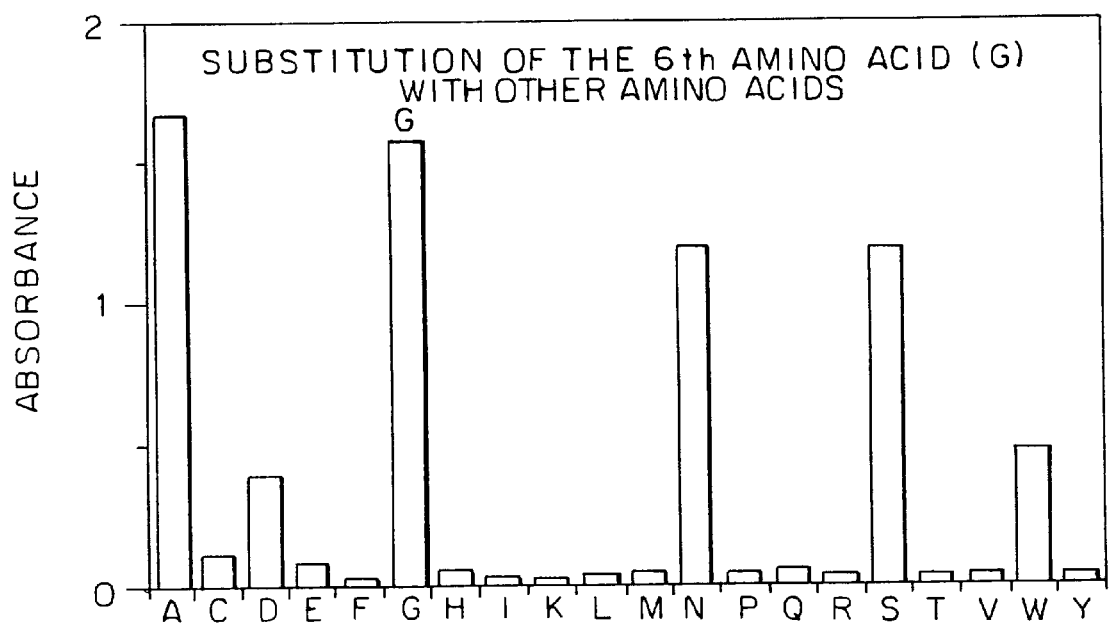
Figure 14:
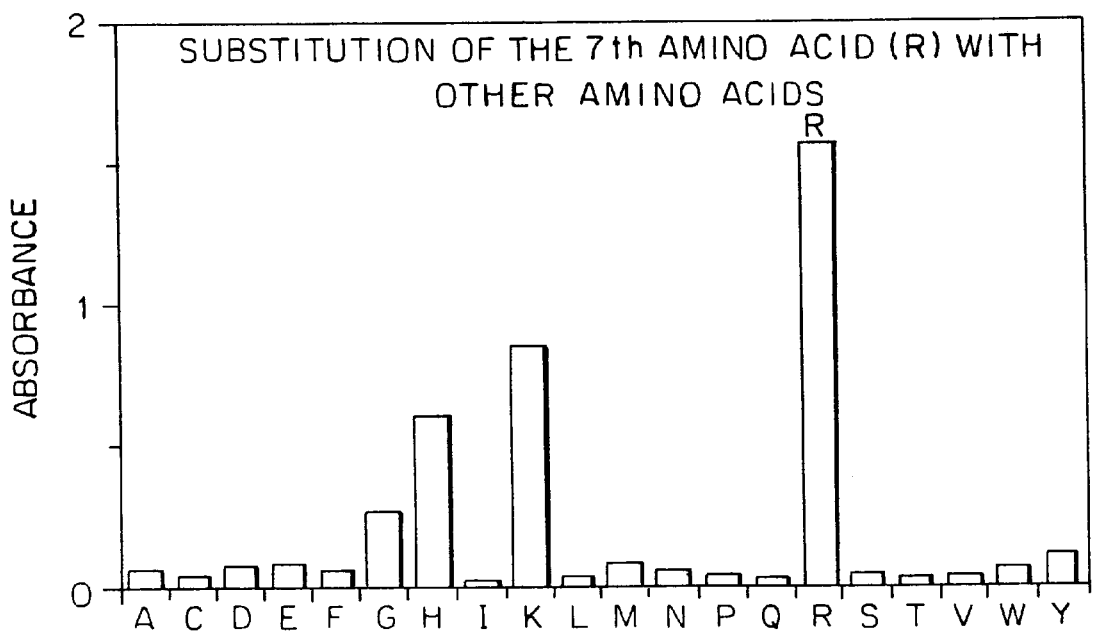
Figure 15:
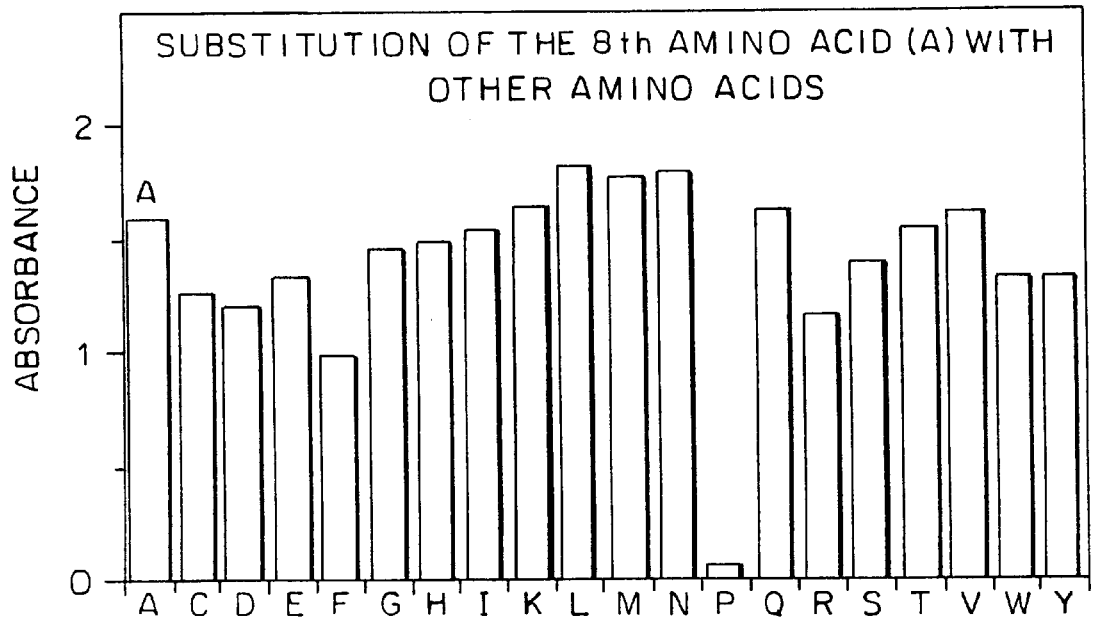
Figure 16:
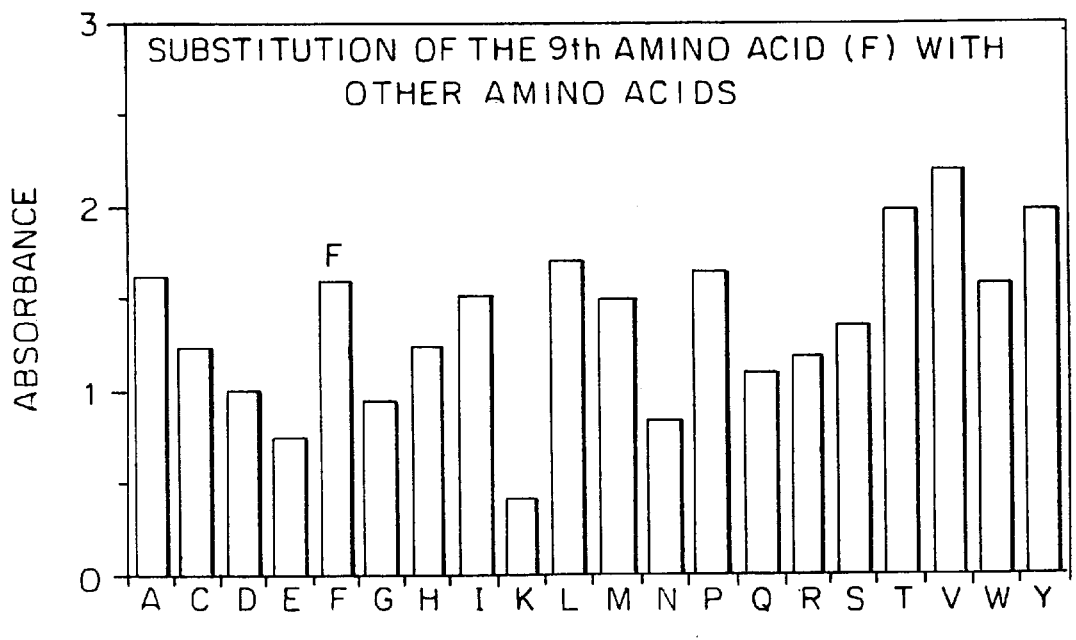
Figure 17:
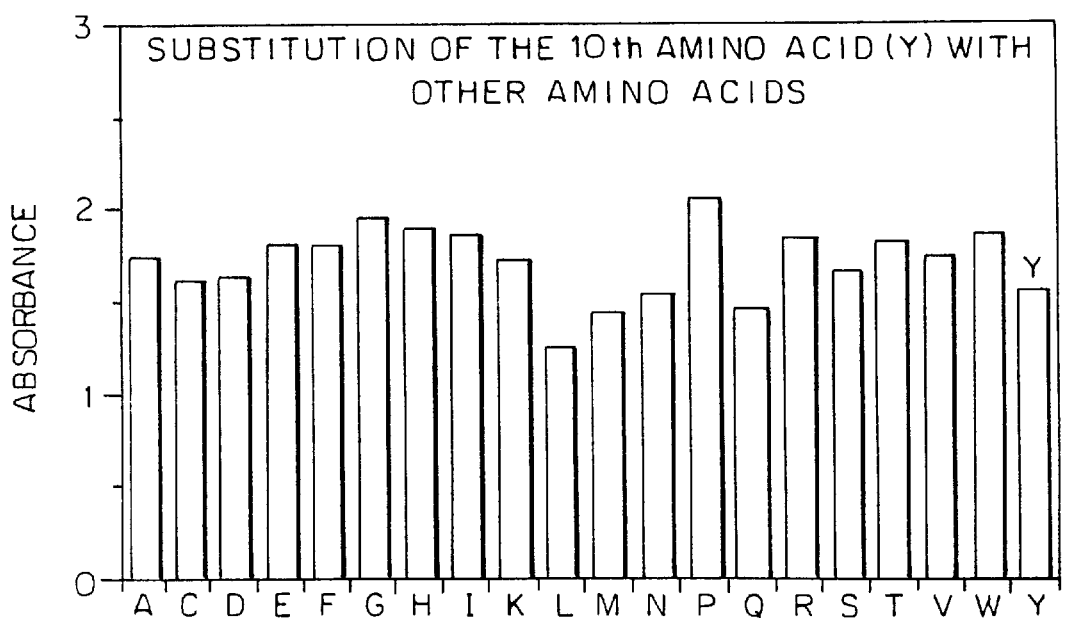

Then, based on the peptide IHIGPGRAFY derived from HIV-MN strain with which C25 antibody reacts, a group of overlapped peptides comprising 3 to 10 amino acids (a series of peptides which have an amino acid sequence shifted one by one from the N terminus) were synthesized on a solid phase as in (1). The reactivity between these peptide groups and C25 antibody was examined by EIA, and a possible portion as an epitope was assessed (FIG. 7).

As a result, C25 antibody had a low reactivity with shorter peptides of less than a pentapeptide but showed a sufficient reactivity with longer peptides of more than a hexapeptide. Among these overlapped hexapeptides, the peptide which showed the strongest reaction was Ile-Gly-Pro-Gly-Arg-Ala (residues 14–19 of SEQ ID NO: 1) and the peptide whose reactivity comes second was Gly-Pro-Gly-Arg-Ala-Phe (residues 15–20 of SEQ ID NO: 1). However, His-Ile-Gly-Pro-Gly-Arg (residues 13–18 of SEQ ID NO: 1) and Pro-Gly-Arg-Ala-Phe-Tyr (residues 16–21 of SEQ ID NO: 1) showed an extremely decreased reactivity, suggesting that the epitope recognized by C25 antibody is the six amino acid sequence, Ile-Gly-Pro-Gly-Arg-Ala (residues 14–19 of SEQ ID NO: 1), like the result shown in (1).

2-4) Amino Acid Substitution Analysis

In order to investigate a broadness of neutralization (neutralization spectrum) of C25 antibody to HIV variants, the reactivity with PND peptides prepared by serially replacing each amino acid with either one of other 19 amino acids was examined (FIGS. 8 to 17). By way of example, the decapeptide IHIGPGRAFY derived from HIV-MN strain was used herein for substitution.

When $Gly_1$, Pro and Arg in $Ile_1$-His-$Ile_2$-$Gly_1$-Pro-$Gly_2$-Arg-Ala-Phe-Tyr (residues 12–21 of SEQ ID NO: 1) were replaced with other amino acids, C25 antibody hardly bound to these peptides. C25 antibody reacted strongly with peptide wherein the 6th $Gly_2$ is replaced with Ala, and hence, it was found that $Gly_2$. can be replaced with Ala. Accordingly, the amino acids which most contribute to the binding were considered to be GPGR. $Ile_2$ located at the N terminal side of GPGR could be replaced with Ala, Leu, Met, Asn, Pro, Gln, Ser, Thr, Val and Tyr, whereas Ala located at the C terminal side of GPGR could be replaced with every amino acids other than Pro. This proved that the amino acids located at the both sides of GPGR are not crucial but contribute to the binding to some extent. Even after replacement of $Ile_1$, His, Phe and Tyr which are located biased more to the N and C termini, with other amino acids, the peptides maintained the reactivity with C25 antibody.

The results of the above experiments 2-3 and 2-4 proved that C25 antibody recognized the epitope formed by six amino acids comprising GPGR as a binding core and each one amino acid adjacent to both sides thereof as shown below.

In addition, the results of the amino acid substitution analysis in 2-4 revealed that C25 antibody could cope with the following many amino acid variances:

(1) Xa1-Gly-Pro-Gly-Arg-Ala (SEQ ID NO: 59)
   wherein Xa1 is Ala, Ile, Leu, Met, Asn, Pro, Gln, Ser, Thr, Val or Tyr;
(2) Ile-Gly-Pro-Gly-Arg-Xa2(SEQ ID NO: 60)
   wherein Xa2 is Ala, Cys, Asp, Glu, Gly, His, Ile, Lys, Leu, Met, Asn, Gln, Arg, Ser, Thr, Val, Trp or Tyr;
(3) Val-Gly-Pro-Gly-Arg-Thr (SEQ ID NO: 61);
(4) Val-Gly-Pro-Gly-Arg-Ser (SEQ ID NO: 62);
(5) Ile-Gly-Pro-Ala-Arg-Ala (SEQ ID NO: 63).

2-5) Reactivity of C25 Antibody with PND Peptides Derived from Viruses of Infected Individuals Then, the reactivity of C25 antibody with HIV actually occurring within the living body of HIV-infected individuals was examined by the following method.

First, peripheral blood lymphocytes (PBL) of HIV-infected individuals were suspended in 1×RSB buffer and thereto were added SDS (final concentration 1%), Proteinase K (final concentration 1 mg/ml), and the mixture was incubated at 37° C. for 2 hours. Then, phenol extraction and ethanol precipitation procedures were repeated to give DNAs (genomic DNAs) having a high molecular weight. Also, HIV particles were precipitated from serum of infected individuals and cDNAs were synthesized with a reverse transcriptase. Using these DNAs having a high molecular weight or cDNAs as a template, gp120/PND region of HIV in infected patients were amplified using the following primers A and B.

Primer A; (5') GCCGGATCCACACATGGAATTAGGCCAGTA(3')(SEQ ID NO: 69)
Primer B; (3') AGTCCTCCCCTGGGTCTTTAAACTGACGTCTCG(5') (SEQ ID NO: 70)

Amplification was carried out using Taq polymerase for 30 to 35 cycles.

The thus obtained amplified DNA fragments were cloned into pUC18 plasmid and the amplified DNA fragments were sequenced by a dideoxy method. Furthermore, the cloned DNA fragments were incorporated into pUEX2 expression vector and E. coli was transfected with this vector and subjected to heat induction at 42° C. for expression. The expressed protein in the form of a fused protein with β-galactosidase was purified from the inclusion in E. coli as follows. E. coli cells which undertook expression were destroyed with glass beads and then treated with lysozyme (final concentration 0.1 mg/ml) at 4° C. and the precipitates obtained from centrifugation were treated with Triton X-100 (final concentration 0.5%). The precipitates obtained from centrifugation were solubilized with 8M urea and then reacted with C25 antibody. The binding property was confirmed by the EIA method and the Western blotting method as described in Example 1 (1-5).

FIG. 18 shows an amino acid sequence of PND region of HIVs which occur most frequently in patients and the reactivity of C25 antibody therewith. C25 antibody bound with the consensus sequences derived from twenty five patients among thirty HIV-infected individuals examined herein. That is, the binding spectrum of C25 antibody was as broad as 83%. On the contrary, the strain-specific monoclonal antibodies, μ5.5 or α64, had a spectrum of only about 30%.

When viruses in an HIV-infected individual were examined for their amino acid sequence, they do not show a completely identical sequence but they infect patient as quasispecies of viruses having a somewhat different amino acid sequence. For driving away viruses from the living body of infected individuals by administration of an antibody, the antibody must react with most of HIVs present within the living body of patient. Tables 2 and 3 show the reactivity of C25 antibody with PND region peptides derived from HIVs isolated from a single patient.

TABLE 4

| HIV-infected individuals | Biding rate of neutralizing antibody (%) | |
|---|---|---|
| | C25 | μ5.5 |
| N156 | 100%(11/11) | 100%(11/11) |
| KMO | 92%(12/13) | 46%(6/13) |
| TI | 93%(14/15) | 20%(3/15) |
| TIW | 100%(12/12) | 0%(0/12) |
| YHI | 92%(11/12) | 0%(0/12) |
| HHA | 100%(35/35) | 60%(21/35) |
| NI229 | 75%(6/8) | 0%(0/8) |
| NI230 | 100%(8/8) | 50%(4/8) |
| NI334 | 100%(8/8) | 25%(2/8) |
| NI373 | 100%(10/10) | 0%(0/10) |
| NI252 | 100%(11/11) | 0%(0/11) |
| NI380 | 82%(9/11) | 46%(5/11) |
| NI382 | 100%(11/11) | 0%(0/11) |
| No. of applicable patients[1] | 8(11) | 1(1) |

Note
[1]Number of patients having an antibody binding rate of 100%
The number in the parenthesis shows number of patients having an antibody binding rate of more than 90%.

TABLE 2

| HIV clone | No. of analysis | Amino acid sequence of PND | SEQ ID NO: | C25 | μ5.5 |
|---|---|---|---|---|---|
| HIV-MN | — | YNKRKRIHIGPGRAFYTTKNIIG | residues 6-28 of SEQ ID NO:1 | | |
| TIW-01 | 7 | N-T---S-P----------GE--- | SEQ ID NO:71 | + | − |
| TIW-02 | 4 | N-T---S-P----------GEV-- | SEQ ID NO:72 | + | − |
| TIW-09 | 1 | N-T---G-P----------GE--- | SEQ ID NO:73 | + | − |
| Binding rate(%) | | | | 100% (12/12) | 0% (0/12) |

TABLE 3

| HIV clone | No. of analysis | Amino acid sequence of PND | SEQ ID NO: | C25 | μ5.5 |
|---|---|---|---|---|---|
| HIV-MN | — | YNKRKRIHIGPGRAFYTTKNIIG | residues 6-28 of SEQ ID NO:1 | | |
| NI230-1 | 3 | N-T---S-------------GE--- | SEQ ID NO:74 | + | + |
| NI230-4 | 1 | N-T---S-------------GE-M- | SEQ ID NO:75 | + | + |
| NI230-8 | 2 | N-T---G-Y------V---ER--- | SEQ ID NO:76 | + | − |
| NI230-7 | 1 | N-T---G-Y------V---GR--- | SEQ ID NO:77 | + | − |
| NI230-5 | 1 | N-T---G-Y------V---ER--- | SEQ IN NO:76 | + | − |
| Binding rate (%) | | | | 100% (8/8) | 50% (4/8) |

In case of the patient TIW, C25 antibody bound all the HIVs whereas μ5.5 bound none of HIVs (Table 2). In case the infected individual NI230, C25 antibody could bind all the HIVs whereas there remained some HIVs with which the antibody μ5.5 could not react (Table 3). Table 4 summarizes results obtained from such 13 HIV-infected individuals. C25 antibody showed a reactivity at a high rate in almost all the infected individuals, wherein 100% reactivity was shown in 8 individuals, and more than 90% reactivity was shown in as many as 11 individuals. On the contrary, the strain-specific μ5.5 antibody showed a low reactivity wherein more than 90% reactivity was shown in only one individual. These proved that C25 antibody could sufficiently cope with a high variability of HIVs and hence could actually clinically applicable.

EXAMPLE 3

Preparation of Chimeric C25 antibody (CC25)
3-1) Isolation of V Region Gene of C25 Antibody Isolation of a gene coding for mouse immunoglobulin variable (V) region was carried out as mentioned hereinbelow. A whole RNAs were extracted from C25 cells in accordance with the conventional procedure (Glober ed. "DNA cloning Vol. 1" IRL press (1985), and a single-stranded cDNA was synthesized using cDNA Synthesis System Plus (Amersham). Using this single-stranded cDNA as a template, a polymerase chain reaction (PCR) was carried out using DNA primers synthesized based on the nucleic acid base sequence of V region and J region as classified by Kabat et al. (Sequences of Proteins of Immunological Interest 4th ed., Public Health Service, NIH, Washington D.C., 1987). HindIII and BamHI sites were included in the V region primer and J region primer, respectively. PCR was conducted in accordance with the protocol of CETUS. That is, each 100 pmol of the primers were used and PCR reagents were a kit from CETUS. The PCR conditions were 94° C. for 1 minute, 55° C. for 1 minute and 72° C. for 1 minute, and PCR was conducted for 25 cycles. After PCR, the obtained DNA fragments were subcloned into HIncII site of pUC18 (manufactured by Takara Shuzo K. K.; the reagents used in this Example were those manufactured by Takara Shuzo K. K. or Toyobo K. K. unless otherwise mentioned).

3-2) Nucleic Acid Base Sequence of Mouse V Region Gene of C25 Antibody

Using Sequenase Ver. 2 kit manufactured by Toyobo K. K., the V region gene incorporated in pUC18 was sequenced. The thus obtained nucleic acid base sequences of C25 antibody are shown in FIGS. 19 (SEQ ID NO: 33) and 20 (SEQ ID NO: 35). Amino acid sequences deduced from the nucleic acid base sequences are also shown in FIGS. 19 (SEQ ID NO: 34) and 20 (SEQ ID NO: 36). The nucleic acid base sequence of C25 antibody showed a rearrangement specific to the V region gene and formed an open reading frame (ORF) which allows for expression.

3-3) Construction of Gene Expressing Chimeric C25 Antibody (CHC25, CLC25)

In order to confirm that the isolated V region gene of C25 antibody is actually a gene coding for V region responsible for anti-HIV activity, a mouse-human chimeric antibody was prepared. For expression of a chimeric antibody, expression vectors, AG-κ and AG-γ1, having a β-actin (AG) promoter were used. AG-κ contains a human κ chain constant region gene and a DHFR gene as a selection marker whereas AG-γ1 contains a human γ1 chain constant region gene and a neo gene as a selection marker. The V region of C25 antibody as prepared above was digested with HindIII and BamHI restriction enzymes and the obtained VH and VL fragments were incorporated into the HindIII-BamHI site of AG-γ1 and AG-κ, respectively (CHC25 and CLC25).

3-4) Expression of Chimeric C25 Antibody (CC25)

The chimeric C25 antibody gene constructed as mentioned above was tested for its antibody activity in a transient expression system using COS7 cell (ATCCCRL 1651). A mixture of CHC25 and CLC25 plasmid DNAs was introduced into COS7 cells using an electoporation device manufactured by Bio-Rad in accordance with the protocol of Bio-Rad, and the COS7 cells were cultured in DMEM medium containing 10% fetal calf serum (GIBCO). After three days, the culture supernatant was collected and the activity of antibodies present in the culture supernatant was measured by ELISA method using anti-human IgG or PND peptides derived from various HIVs. As a result, an expression product of the mixture of CHC25 and CLC25 plasmid DNAs could bind with the anti-human IgG. The reactivity with various PND peptides was compared with that of the original C25 antibody and thereby the expression product showed a reaction spectrum similar to that of the original C25 antibody. Furthermore, the neutralizing activity against HIV-MN strain was also tested, and as a result, the expression product was found to inhibit viral infection by 100% at a minimum effective concentration of 1 μg/ml like the mouse C25 antibody. Accordingly, it was proved that the C25 antibody V region gene isolated as mentioned above is exactly a gene coding for V region of an antibody having a neutralizing activity.

3-5) Preparation of a Cell Strain Producing Chimeric C25 Antibody at High Rate

For preparing a stable plasma cell line producing chimeric C25 antibody (CC25), the above-mentioned plasmid DNAs, CLC25 and CHC 25, were linearized with PvuI, and CHO-DG44 cells and P3-653 cells were transformed with a mixture of the linearized DNAs and lipofectin. As in the temporal expression of the chimeric antibody, a culture supernatant of Neo-resistant DHFR-resistant cells where the genes are introduced was collected, and the activity of antibodies present in the culture supernatant was measured by ELISA method using an anti-human IgG and various PND peptides. An expression product by cotranfection with CLC25 and CHC25 plasmid DNAs bound with various PND peptides, and hence, this transformed cell was cloned. Furthermore, an amplification procedure for DHFR gene was repeated by adding MTX at a concentration of 4 to $32 \times 10^{-7}$ M. As a result, a stable plasma cell line which is resistant to MTX and produces CC25 antibody at a level of 50 to 70 μg/ml.

EXAMPLE 4

Preparation of Humanized C25 Antibody (RC25)

4-1) Transplantation of CDRs of C25 Antibody V Region Gene by PCR Mutagenesis

In order to investigate an important region for antigen binding among VH and VL regions of the cloned C25 antibody, CDR (complementarity determining) regions of C25 antibody were transplanted into a human V region. This was carried out in accordance with the method for preparing a humanized antibody (Japanese Patent First Publication No. 4-141095). CDR region of C25 antibody VH region was transplanted into VH region having a framework (FR) region of human subgroup II (NEW: donated by Dr. Bendig of U.K. MRC Collaborative Centre) whereas CDR region of C25 antibody VL region was transplanted into VL region having FR region of human κ chain (REI: W. Palm and N. Hilscmann, Z.Physiol.Chem., 356, 167 (1975)). Specifically, this was conducted by PCR-mutagenesis wherein mutation is introduced by PCR (Saiki, R. G. et al., Science, 239, 487 (1988)) into the humanized antibody μ5.5 or 0.5β which the present inventors have previously prepared. FIGS. 21, 22 and 23 show the synthetic primers used for mutagenesis which are annealed to a PCR template, i.e. VH and VL regions of the humanized antibody.

The condition of PCR was 94° C. for 1 minute, 55° C. for 1 minute and 72° C. for 1 minute and 25 cycles were repeated.

In case of VH, using VH gene of the humanized antibody μ5.5 (Japanese Patent First Publication No. 4-152893) as a template and primers #1 and #2, the 5' site of the VH gene was amplified (FIG. 21). This was linked via the central BglII site to a gene fragment (FIG. 22) which is prepared by amplification with primers #3 and #4 using the VH gene of the humanized antibody 0.5β (Hum.Antibod.Hybridomas, 2, p124 (1991)) as a template. On the other hand, in case of VL, the 5' site of VL was amplified using primer #5 and M13-M4 primers and the 3' site of VL was amplified using primer #8 and M13-reverse primer, and the resulting amplified genes were linked together to form KpnI site, which site is self-annealed with synthetic DNAs #6 and #7 (FIG. 23).

Thus, V regions of the humanized C25 antibody (RHC25 and RLC25, respectively: cf. SEQ ID NO: 79 and SEQ ID NO: 81) were obtained. These humanized V region fragments were digested with HindIII and BamHI restriction enzymes as in preparation of the chimeric antibody (cf. Example 3) and the resulting VH and VL fragments were incorporated into the HindIII-BamHI site of AG-γ1 and AG-κ, respectively. Thus, expression vectors for humanized C25 antibody (RHC25 and RLC25, respectively) were prepared.

4-2) Expression of Humanized C25 Antibody (RC25)

The activity of antibodies obtained by the thus prepared humanized antibody gene was examined in a transient expression system of the above-mentioned COS7 cells. As in the transient expression of the chimeric antibody, the culture supernatant of cells where the gene was introduced was collected and the activity of antibodies present in the culture supernatant was measured by ELISA method using an anti-human IgG or PND peptides derived from various HIVs. As a result, expression products of a mixture of RHC25 and RLC25 plasmid DNAs bound various PND peptides. Furthermore, the expression products were examined for the neutralizing activity against HIV-MN strain, and as a result, it was found that they inhibit the viral infection by 100% at a minimum effective concentration of 1 μg/ml like C25 mouse antibody and the chimeric antibody. Accordingly, among the amino acid sequence of C25 antibody as shown in FIGS. 19 and 20, the transplanted CDR regions are an important region for exerting the anti-HIV activity, and hence, the gene coding for these regions is the most important gene for preparing a recombinant antibody.

4-3) Preparation of Cell Line Producing Humanized C25 Antibody at High Rate

In order to prepare a stable plasma cell line producing the humanized C25 antibody (RC25), the above-mentioned plasmid DNAs RLC25 and RHC25 were linearized with PvuI and the linearized DNAs, as a mixture with lipofectin, were used for transformation of CHO-DG44 cells and P3-653 cells. As in the case of the transient expression of the chimeric antibody, the culture supernatant of neo-resistant DHFR-resistant cells wherein the gene is introduced was collected and the activity of antibodies present in the culture supernatant was measured by ELISA method using an anti-human IgG and various PND peptides. An expression product by cotranfection with RLC25 and RHC25 plasmid DNAs bound with various PND peptides, and hence, this transformed cell was cloned. Furthermore, an amplification procedure for DHFR gene was repeated by adding MTX at a concentration of 4 to $32 \times 10^{-7}$ M. As a result, a stable plasma cell line which is resistant to MTX and produces RC25 antibody at a level of 80 to 100 μg/ml was prepared.

EXAMPLE 5

Effector Activity of Chimeric and Humanized C25 Antibodies 5-1) Antibody Dependent Complement-mediated Cytotoxicity (ACC)

C25 antibody, chimeric C25 antibody (CC25), humanized C25 antibody (RC25) and normal human IgG (NHG) were diluted in RPMI1640 containing 5% FCS to a final concentration of 0.1 to 50 μg/ml and each 50 μl was added to a 96-well plate. Then, H9 cells with continuous infection of HIV-MN ($2.5 \times 10^5$ cells; 100 μl) and fresh human serum (30 μl) were added and the plate was allowed to stand at 37° C. for 1 hour. After 1 hour, the cells were dyed with trypan blue and the numbers of living cells and of dead cells were counted.

As shown in FIG. 24, 10 μg/ml of CC25 antibody and RC25 antibody destroyed about 70% of the target cells whereas C25 antibody and NHG showed a low cytotoxicity. This proved that the chimeric and the humanized C25 antibodies had a strong ACC activity.

5-2) Antibody Dependent Cell-mediated Cytotoxicity (ADCC)

Cells with continuous infection of HIV-MN were established using CEM cells resistant to NK cells (CEM-NKR) and used as a target cell. The infected cells ($3 \times 10^6$ cells) were suspended in RPMI1640 containing 10% FCS (1 ml) and labelled with $^{51}$Cr for 90 minutes. The cells ($10^4$ cells) were inoculated on a 96-well plate and thereto were added each 0.1 to 10 μg/ml of C25 antibody, CC25 antibody, RC25 antibody and NHG. Then, normal human peripheral blood lymphocytes ($5 \times 10^5$ cells) were added and the plate was incubated for 4 hours. Percentage of destroyed cells was obtained in the usual manner.

As shown in FIG. 25, under condition of effector cells/target cells=50, 1 μg/ml of CC25 antibody and RC25 antibody destroyed about 50% of the target cells whereas C25 antibody showed as low cytotoxicity as that of NHG. This revealed that C25 antibody and NHG showed a low cytotoxicity activity and proved that the chimeric and humanized C25 antibodies had a strong ADCC activity.

EXAMPLE 6

Effectiveness of Humanized C25 Antibody (RC25) to Viruses Derived from Patients 6-1) Binding Property of RC25 Antibody with Viruses Derived from Patients Since it is known that HIV occurs as quasispecies of variant viruses in a single patient, in accordance with the procedures of Example 2 (2-5), a base sequence of PND region of viral RNA in plasma and of proviral DNA in peripheral blood mononuclear cells derived from anti-HIV antibody positive patients was analyzed with multiple clones per one specimen, and the binding property of RC25 antibody with recombinant PND proteins prepared based on the obtained sequence was examined. Table 5 shows the binding property of RC25 antibody with PNDs of peripheral blood mononuclear cells derived from various patients in comparison with HIV-IIIB type virus-specific chimeric antibody (Cβ1) and MN type virus-specific humanized antibody (Rμ5.5). As is clear from Table 5, RC25 antibody bound with the PND recombinant proteins derived from various patients at a high rate of 91 to 100%.

TABLE 5

| HIV-infected | Binding rate of neutralizing antibody | | |
|---|---|---|---|
| individuals | RC25 | R μ5.5 | Cβ1 |
| YHI | 91%(11/12) | 8%(1/12) | 0%(0/12) |
| ASA | 100%(7/7) | 0%(0/7) | 0%(0/7) |
| HHA | 100%(46/46) | 69%(32/46) | 0%(0/46) |
| MNI | 100%(24/24) | 91%(22/24) | 0%(0/24) |
| KMO | 92%(12/13) | 53%(7/13) | 0%(0/13) |
| MOK | 100%(24/24) | 100%(24/24) | 0%(0/24) |

6-2) Neutralizing activity of RC25 antibody to. viruses derived from patient plasma RC25 antibody (2 mg/ml; 5 μl) was reacted with the patient plasma (50 μl) used in the above 6-1 at room temperature for 30 minutes. Culture was started by adding a mixture of RC25 antibody and plasma to normal human peripheral blood mononuclear cell system (50 μl) wherein CD8-positive cells were removed with anti-CD8 antibody-bound magnetic beads (manufactured by Dinal) in ten times higher amount than that of the mononuclear cells in order to enhance production of viruses and, after activation with 10 μg/ml of phytohemaggulitin for three days, the mononuclear cells were cultured in a culture medium containing interleukin-2 for 4 days. After four days, the cells were washed with fresh medium and then culture was continued while collection of supernatant and culture exchange were conducted at an interval of 5 to 7 days. A concentration of HIV-1 p24 antigen in the collected culture supernatant was measured using a kit for detecting HIV antigen (manufactured by Dinabbott). In all the tested cases where viral infection from patient plasma to normal human peripheral blood mononuclear cells occurred, as shown in FIG. 26, HIV-IIIB type virus-specific chimeric antibody (Cβ1) and MN type virus-specific humanized antibody (Rμ5.5) used as a control antibody were ineffective, but the group in which R25 antibody was added showed less than detection limit of p24 antigen production, and thereby an apparent effect of RC25 antibody to inhibit infection was confirmed.

6-3) Neutralizing Activity of RC25 Antibody to Viruses Derived from Peripheral Blood Mononuclear Cells of Patients Mononuclear cells were prepared from the above-mentioned patient peripheral blood (20 to 40 ml), CD8-positive cells were removed by the above-mentioned procedure in order to enhance production of viruses, and then the cells were cultured in the presence of anti-CD3 monoclonal antibody (0.5 μg/ml) for 3 to 5 days to produce viruses. Culture was further continued in the presence of 60, 120 and 240 μg/ml of RC25 antibody while collection of supernatant and culture exchange were conducted at an interval of 5 to 7 days, and a concentration of HIV-1 p24 antigen in the culture supernatant was measured as mentioned hereinabove. In all the tested cases using peripheral blood mononuclear cells of patients showing more than 90% binding of RC25 antibody with the PND proteins prepared based on proviral DNA in peripheral blood mononuclear cells, RC25 antibody inhibited production of viral antigen in a concentration dependent manner as shown in FIGS. 27 to 30.

6-4) Neutralizing Activity of RC25 Antibody to Viruses Derived from Peripheral Blood Mononuclear Cells from Patients after Reconstitution of CD8

The above test procedures for confirming the effectiveness of the present invention, which mimic in vivo style of HIV infection by activating latent proviruses in infected cells of patients to induce viral infection, were conducted under quite severe conditions wherein CD8-positive cells were removed and viral activation was artificially introduced by the anti-CD3 antibody. Accordingly, RC25 antibody which was proved to be extremely effective in the test procedures is expected, if clinically applied to patients, to be much more effective than in the test procedures.

Thus, the same test procedures mentioned hereinabove were conducted with reconstitution of one tenth amount of the removed CD8-positive cells at the addition of the antibody. As a result, as shown in FIG. 31, an effective concentration of RC25 antibody was reduced to as low as 30 μg/ml, suggesting that RC25 antibody is quite effective in clinical application.

INDUSTRIAL APPLICABILITY OF THE INVENTION

HIV is a highly variable virus which infects to a single patient as quasispecies of variant viruses having a different amino acid sequences. In order to exert treating efficacy even to such quasispecies of variant viruses, it is essential to identify a conserved region among HIV strains and establish a neutralizing antibody which recognizes said conserved region. V3-PND region of HIV is an important site which induces a strong neutralizing antibody and a monoclonal antibody to PND-Tip region comprising the conserved sequence GPGR is believed to have a broad neutralization spectrum.

The present inventors have established a novel method for immunization which allows for efficient preparation of the neutralizing monoclonal antibody recognizing the region conserved among each strain, and have established C25 monoclonal antibody which neutralizes many HIV strains isolated from infected individuals. Furthermore, by humanization of said antibody, the antibody was reduced in antigenicity in humans and endowed with ability to destroy infected cells in Fc region dependent manner. Furthermore, contrary to the conventional HIV neutralizing antibodies which showed effectiveness only to a single virus isolated in laboratory, the antibody of the present invention was confirmed to be apparently effective to quasispecies of many variant viruses within the body of patient due to its broad neutralization spectrum. Accordingly, the antibody of the present invention can respond to diversity and variability of various HIVs and can be clinically applicable as a medicament for prevention, treatment or diagnosis of HIV.

What is claimed is:

1. A monoclonal antibody produced by the hybridoma deposited with the National Institute of Bioscience and Human-Technology, Agency of Industrial Science and Technology and having the accession number FERM BP-4561, or a fragment thereof which has an ability to neutralize HIV having an epitope, to which said monoclonal antibody binds, defined by a sequence of six amino acids selected from the group consisting of Xaa-Gly-Pro-Gly-Arg-Ala (SEQ ID NO: 59) wherein Xaa is Ala, Ile, Leu, Met, Asn, Pro, Gln, Ser, Thr, Val, or Tyr; Ile-Gly-Pro-Gly-Arg-Xaa (SEQ ID NO: 60), wherein Xaa is Ala, Cys, Asp, Glu, Gly, His, Ile, Lys, Leu, Met, Asn, Gln, Arg, Ser, Thr, Val, Trp, or Tyr; Val-Gly-Pro-Gly-Arg-Thr (SEQ ID NO: 61); Val-Gly-Pro-Gly-Arg-Ser (SEQ ID NO: 62); and Ile-Gly-Pro-Ala-Arg-Ala (SEQ ID NO: 63) within the principle neutralization domain (PND) in the third variable region (V3) of glycoprotein antigen having a molecular weight of about $1.2 \times 10^5$ daltons (gp120) on a human immunodeficiency virus (HIV) external envelope.

2. The monoclonal antibody or fragment thereof as set forth in claim 1, wherein an amino acid sequence of complementarity determining regions 1 to 3 (CDR1 to CDR3) of H chain variable region has the following sequences:

Asn Ser Trp Ile Gly (residues 9–13 of SEQ ID NO: 40) in CDR1;

Asp Ile Tyr Pro Gly Gly Gly Tyr Thr Asn Tyr Asn Glu Ile Phe Lys Gly (residues 69–85 of SEQ ID NO: 34) in CDR2; and Gly Ile Pro Gly Tyr Ala Met Asp Tyr (residues 7–15 of SEQ ID NO: 48) in CDR3.

3. The monoclonal antibody or fragment thereof as set forth in claim 2 wherein an amino acid sequence of H chain variable region is the amino acid sequence as shown in residues 20–137 of SEQ ID NO: 34.

4. The monoclonal antibody or fragment thereof as set forth in claim 1, wherein an amino acid sequence of complementarity determining regions 1 to 3 (CDR1 to CDR3) of L chain variable region has the following sequences:

Lys Ser Ser Gln Ser Leu Leu Asn Ser Gly Asp Gln Lys Asn Tyr Leu Thr (residues 7–23 of SEQ ID NO: 53) in CDR1;

Trp Ala Ser Thr Gly Glu Ser (residues 15–21 of SEQ ID NO: 54) in CDR2; and

Gln Asn Asp Tyr Ser Tyr Pro Trp Thr (residues 23–31 of SEQ ID NO: 57) in CDR3.

5. The monoclonal antibody or fragment thereof as set forth in claim 4 wherein an amino acid sequence of L chain variable region is the amino acid sequence as shown in residues 25–137 of SEQ ID NO: 36.

6. A process for preparing a monoclonal antibody produced by the hybridoma deposited with the National Institute of Bioscience and Human-Technology, Agency of Industrial Science and Technology and having the accession number PERM BP-4561, or a fragment thereof which has an ability to neutralize HIV having an epitope, to which the monoclonal antibody binds, defined by the amino acid sequence of Xa1-Gly-Pro-Xa2-Arg-Xa3 (SEQ ID NO: 58), wherein Xa1 is Ala, Ile, Leu, Met, Asn, Pro, Gln, Ser, Thr, Val, or Tyr; Xa2 is Gly or Ala; and Xa3 is Ala, Cys, Asp, Glu, Gly, His, Ile, Lys, Leu, Met, Asn, Gln, Arg, Ser, Thr, Val, Trp, or Tyr, within the principal neutralization domain (PND) in the third variable region (V3) of glycoprotein antigen having a molecular weight of about $1.2 \times 10^5$ daltons (gp120) on a human immunodeficiency virus (HIV) external envelope, said process comprising serially immunizing an animal with a plurality of peptides, each of said plurality of peptides comprising the Gly-Pro-Gly-Arg (residues 15–18 of SEQ ID NO: 1) sequence in common but having different amino acid sequences in the flanking regions, removing spleen cells from said animal, fusing the spleen cells with myeloma cells to produce hybridoma cell lines, and screening the resultant hybridoma cell lines for hybridoma cell lines which produce said monoclonal antibody.

7. An H chain of a recombinant anti-HIV antibody which has an ability to neutralize HIV having an epitope, to which said anti-HIV antibody binds, defined by an amino acid sequence of Xa1-Gly-Pro-Xa2-Arg-Xa3 (SEQ ID NO: 58), wherein Xa1 is Ala, Ile, Leu, Met, Asn, Pro, Gln, Ser, Thr, Val, or Tyr; Xa2 is Gly or Ala; and Xa3 is Ala, Cys, Asp, Glu, Gly, His, Ile, Lys, Leu, Met, Asn, Gln, Arg, Ser, Thr, Val, Trp, or Tyr, within the principal neutralization domain (PND) in the third variable region (V3) of glycoprotein antigen having a molecular weight of about $1.2 \times 10^5$ daltons (gp120) on a human immunodeficiency virus (HIV) external envelope, wherein either the complementarity determining regions 1 to 3 (CDR1 to CDR3) or the whole variable region are derived from a mouse antibody produced by the hybridoma deposited with the National Institute of Bioscience and Human-Technology, Agency of Industrial Science and Tecnology and having the accession number FERM BP-4561, and the rest of the H chain is derived from a human antibody.

8. The H chain of a recombinant anti-HIV antibody as set forth in claim 7, wherein said antibody has an ability to neutralize HIV having an epitope, to which said anti-HIV antibody binds, defined by a sequence of six amino acids selected from the group consisting of Xaa-Gly-Pro-Gly-Arg-Ala (SEQ ID NO: 59), wherein Xaa is Ala, Ile, Leu, Met, Asn, Pro, Gln, Ser, Thr, Val, or Tyr; Ile-Gly-Pro-Gly-Arg-Xaa (SEQ ID NO: 60), wherein Xaa is Ala, Cys, Asp, Glu, Gly, His, Ile, Lys, Leu, Met, Asn, Gln, Arg, Ser, Thr, Val, Trp, or Tyr; Val-Gly-Pro-Gly-Arg-Thr (SEQ ID NO: 61); Val-Gly-Pro-Gly-Arg-Ser (SEQ ID NO: 62); and Ile-Gly-Pro-Ala-Arg-Ala (SEQ ID NO: 63) within said PND.

9. The H chain of a recombinant anti-HIV antibody as set forth in claim 7, wherein an amino acid sequence of complementarity determining regions 1 to 3 (CDR1 to CDR3) of H chain variable region has the following sequences:

Asn Ser Trp Ile Gly (residues 9–13 of SEQ ID NO: 40) in CDR1;

Asp Ile Tyr Pro Gly Gly Gly Tyr Thr Asn Tyr Asn Glu Ile Phe Lys Gly (residues 69–85 of SEQ ID NO: 34) in CDR2; and Gly Ile Pro Gly Tyr Ala Met Asp Tyr (residues 7–15 of SEQ ID NO: 48) in CDR3.

10. The H chain of a recombinant anti-HIV antibody as set forth in claim 9, wherein said recombinant anti-HIV antibody is a chimeric antibody and an amino acid sequence of H chain variable region is the amino acid sequence of residues 20 to 137 of SEQ ID NO: 34.

11. The H chain of a recombinant anti-HIV antibody as set forth in claim 9, wherein said recombinant anti-HIV antibody is a humanized antibody and an amino acid sequence of H chain variable region is the amino acid sequence of SEQ ID NO: 80.

12. An L chain of a recombinant anti-HIV antibody which has an ability to neutralize HIV having an epitope, to which said anti-HIV antibody binds, defined by the amino acid sequence of Xa1-Gly-Pro-Xa2-Arg-Xa3 (SEQ ID NO: 58), wherein Xa1 is Ala, Ile, Leu, Met, Asn, Pro, Gln, Ser, Thr, Val, or Tyr; Xa2 is Gly or Ala; and Xa3 is Ala, Cys, Asp, Glu, Gly, His, Ile, Lys, Leu, Met, Asn, Gln, Arg, Ser, Thr, Val, Trp, or Tyr, within the principal neutralization domain (PND) in the third variable region (V3) of glycoprotein antigen having a molecular weight of about $1.2 \times 10^5$ daltons (gp120) on a human immunodeficiency virus (HIV) external envelope, wherein either the complementarity determining regions 1 to 3 (CDR1 to CDR3) or the whole variable region are derived from a mouse antibody produced by the hybridoma deposited with the National Institute of Bioscience and Human-Technology, Agency of Industrial Science and Technology and having the accession number FERM BP-4561, and the rest of the L chain is derived from a human antibody.

13. The L chain of a recombinant anti-HIV antibody as set forth in claim 12, wherein said antibody has an ability to neutralize HIV having an epitope, to which said anti-HIV antibody binds, defined by a sequence of six amino acids selected from the group consisting of Xaa-Gly-Pro-Gly-Arg-Ala (SEQ ID NO: 59), wherein Xaa is Ala, Ile, Leu, Met, Asn, Pro, Gln, Ser, Thr, Val, or Tyr; Ile-Gly-Pro-Gly-Arg-Xaa (SEQ ID NO: 60), wherein Xaa is Ala, Cys, Asp, Glu, Gly, His, Ile, Lys, Leu, Met, Asn, Gln, Arg, Ser, Thr, Val, Trp, or Tyr; Val-Gly-Pro-Gly-Arg-Thr (SEQ ID NO: 61); Val-Gly-Pro-Gly-Arg-Ser (SEQ ID NO: 62); and Ile-Gly-Pro-Ala-Arg-Ala (SEQ ID NO: 63) within said PND.

14. The L chain of a recombinant anti-HIV antibody as set forth in claim 12, wherein an amino acid sequence of complementarity determining regions 1 to 3 (CDR1 to CDR3) of L chain variable region has the following sequences:

Lys Ser Ser Gln Ser Leu Leu Asn Ser Gly Asp Gln Lys Asn Tyr Leu Thr (residues 7–23 of SEQ ID NO: 53) in CDR1;

Trp Ala Ser Thr Gly Glu Ser (residues 15–21 of SEQ ID NO: 54) in CDR2; and

Gln Asn Asp Tyr Ser Tyr Pro Trp Thr (residues 23–31 of SEQ ID NO: 57) in CDR3.

15. The L chain of a recombinant anti-HIV antibody as set forth in claim 14, wherein said recombinant anti-HIV antibody is a chimeric antibody and an amino acid sequence of L chain variable region is the amino acid sequence of residues 25 to 137 of SEQ ID NO: 37.

16. The L chain of a recombinant anti-HIV antibody as set forth in claim 14, wherein said recombinant anti-HIV antibody is a humanized antibody and an amino acid sequence of L chain variable region is the amino acid sequence of SEQ ID NO: 82.

17. A recombinant anti-HIV antibody which comprises the H chain of a recombinant anti-HIV antibody as set forth in claim 7 and the L chain of a recombinant anti-HIV antibody which has an ability to neutralize HIV which has an epitope, to which said anti-HIV antibody binds, defined by the amino acid sequence of Xa1-Gly-Pro-Xa2-Arg-Xa3 (SEQ ID NO: 58), wherein Xa1 is Ala, Ile, Leu, Met, Asn, Pro, Gln, Ser, Thr, Val, or Tyr; Xa2 is Gly or Ala; and Xa3 is Ala, Cys, Asp, Glu, Gly, His, Ile, Lys, Leu, Met, Asn, Gln, Arg, Ser, Thr, Val, Trp, or Tyr, within the principal neutralization domain (PND) in the third variable region (V3) of glycoprotein antigen having a molecular weight of about $1.2 \times 10^5$ daltons (gp120) on a human immunodeficiency virus (HIV) external envelope, wherein either the complementarity determining regions 1 to 3 (CDR1 to CDR3) or the whole variable region are derived from a mouse antibody produced by the hybridoma deposited with the National Institute of Bioscience and Human-Technology, Agency of Industrial Science and Technology and having the accession number FERM BP-4561, and the rest of the L chain is derived from a human antibody.

18. A process for preparing an anti-HIV antibody which comprises constructing an expression vector capable of expressing the recombinant anti-HIV antibody as set forth in claim 17, expressing said expression vector in an animal cell and collecting said antibody.

* * * * *